(12) United States Patent
Su et al.

(10) Patent No.: US 12,377,093 B2
(45) Date of Patent: *Aug. 5, 2025

(54) PYRUVATE KINASE ACTIVATORS FOR USE IN THERAPY

(71) Applicant: Agios Pharmaceuticals, Inc., Cambridge, MA (US)

(72) Inventors: Shin-San Michael Su, Boston, MA (US); Lenny Dang, Boston, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/368,709

(22) Filed: Sep. 15, 2023

(65) Prior Publication Data

US 2024/0277701 A1    Aug. 22, 2024

Related U.S. Application Data

(63) Continuation of application No. 17/221,423, filed on Apr. 2, 2021, now Pat. No. 11,793,806, which is a continuation of application No. 16/821,101, filed on Mar. 17, 2020, now abandoned, which is a continuation of application No. 15/965,088, filed on Apr. 27, 2018, now Pat. No. 10,632,114, which is a continuation of application No. 15/583,412, filed on May 1, 2017, now Pat. No. 9,980,961, which is a continuation of application No. 14/886,750, filed on Oct. 19, 2015, now Pat. No. 9,682,080, which is a continuation of application No. 14/115,289, filed as application No. PCT/US2012/036412 on May 3, 2012, now Pat. No. 9,193,701.

(60) Provisional application No. 61/482,171, filed on May 3, 2011.

(51) Int. Cl.

| | |
|---|---|
| *A61K 31/535* | (2006.01) |
| *A61K 31/496* | (2006.01) |
| *A61K 31/4965* | (2006.01) |
| *A61K 31/497* | (2006.01) |
| *A61P 7/06* | (2006.01) |
| *C07C 307/10* | (2006.01) |
| *C07D 205/04* | (2006.01) |
| *C07D 213/81* | (2006.01) |
| *C07D 215/14* | (2006.01) |
| *C07D 235/06* | (2006.01) |
| *C07D 241/04* | (2006.01) |
| *C07D 241/20* | (2006.01) |
| *C07D 271/12* | (2006.01) |
| *C07D 295/192* | (2006.01) |
| *C07D 333/24* | (2006.01) |
| *C07D 401/12* | (2006.01) |
| *C07D 405/12* | (2006.01) |
| *C07D 417/12* | (2006.01) |
| *A61K 31/415* | (2006.01) |
| *A61K 31/4406* | (2006.01) |
| *A61K 31/47* | (2006.01) |
| *C07C 13/04* | (2006.01) |
| *C07D 307/14* | (2006.01) |

(52) U.S. Cl.
CPC ........ *A61K 31/496* (2013.01); *A61K 31/4965* (2013.01); *A61K 31/497* (2013.01); *A61K 31/535* (2013.01); *A61P 7/06* (2018.01); *C07C 307/10* (2013.01); *C07D 205/04* (2013.01); *C07D 213/81* (2013.01); *C07D 215/14* (2013.01); *C07D 235/06* (2013.01); *C07D 241/04* (2013.01); *C07D 241/20* (2013.01); *C07D 271/12* (2013.01); *C07D 295/192* (2013.01); *C07D 333/24* (2013.01); *C07D 401/12* (2013.01); *C07D 405/12* (2013.01); *C07D 417/12* (2013.01); *A61K 31/415* (2013.01); *A61K 31/4406* (2013.01); *A61K 31/47* (2013.01); *C07C 13/04* (2013.01); *C07D 307/14* (2013.01)

(58) Field of Classification Search
CPC ............................. A61K 31/535; C07D 471/04
USPC ....................................... 514/234.2; 544/127
See application file for complete search history.

(56) References Cited

U.S. PATENT DOCUMENTS

| | | |
|---|---|---|
| 2,390,529 A | 12/1945 | Friedheim |
| 3,046,122 A | 7/1962 | Siis et al. |
| 3,097,210 A | 7/1963 | Bicking |
| 3,755,322 A | 8/1973 | Winter et al. |
| 3,867,383 A | 2/1975 | Winter |
| 3,998,828 A | 12/1976 | Wiedermann |
| 4,084,053 A | 4/1978 | Desai et al. |
| 4,235,871 A | 11/1980 | Papahadjopoulos et al. |
| 4,315,940 A | 2/1982 | Hitzel et al. |
| 4,474,599 A | 10/1984 | Rogers et al. |
| 4,501,728 A | 2/1985 | Geho et al. |

(Continued)

FOREIGN PATENT DOCUMENTS

| | | |
|---|---|---|
| CA | 2235621 A1 | 5/1997 |
| CN | 101296909 A | 10/2008 |

(Continued)

OTHER PUBLICATIONS

Engelman et al., "Allelic Dilution Obscures Detection of a Biologically Significant Resistance Mutation in EGFR-Amplified Lung Cancer," J Clin Invest. 116: 2695-2706 (2006).

(Continued)

*Primary Examiner* — Raymond J Henley, III
(74) *Attorney, Agent, or Firm* — GOODWIN PROCTER LLP

(57) ABSTRACT

Described herein are methods for using compounds that activate pyruvate kinase.

16 Claims, 58 Drawing Sheets

(56) References Cited

U.S. PATENT DOCUMENTS

| | | | |
|---|---|---|---|
| 4,591,548 A | 5/1986 | Delprato | |
| 4,593,102 A | 6/1986 | Shanklin, Jr. | |
| 4,775,762 A | 10/1988 | Knox et al. | |
| 4,837,028 A | 6/1989 | Allen | |
| 4,849,424 A | 7/1989 | Ikeda et al. | |
| 4,881,965 A | 11/1989 | Yamamoto et al. | |
| 4,889,553 A | 12/1989 | Rowson et al. | |
| 4,959,094 A | 9/1990 | Wegner et al. | |
| 5,019,369 A | 5/1991 | Presant et al. | |
| 5,021,421 A | 6/1991 | Hino et al. | |
| 5,122,530 A | 6/1992 | Tomioka et al. | |
| 5,180,732 A | 1/1993 | Tomioka et al. | |
| 5,220,028 A | 6/1993 | Iwasawa et al. | |
| 5,252,590 A | 10/1993 | Tomioka et al. | |
| 5,489,591 A | 2/1996 | Kobayashi et al. | |
| 5,556,866 A | 9/1996 | Aga et al. | |
| 5,807,876 A | 9/1998 | Armistead et al. | |
| 5,834,485 A | 11/1998 | Dyke et al. | |
| 5,843,485 A | 12/1998 | Fernandez et al. | |
| 5,962,490 A | 10/1999 | Chan et al. | |
| 5,965,559 A | 10/1999 | Faull et al. | |
| 5,965,569 A | 10/1999 | Camps Garcia et al. | |
| 5,984,882 A | 11/1999 | Rosenschein et al. | |
| 6,020,357 A | 2/2000 | Pinto et al. | |
| 6,106,849 A | 8/2000 | Malkan et al. | |
| 6,150,356 A | 11/2000 | Lloyd et al. | |
| 6,172,005 B1 | 1/2001 | Selby | |
| 6,262,113 B1 | 7/2001 | Widdowson et al. | |
| 6,265,588 B1 | 7/2001 | Mullner et al. | |
| 6,274,620 B1 | 8/2001 | Labrecque et al. | |
| 6,313,127 B1 | 11/2001 | Waterson et al. | |
| 6,399,358 B1 | 6/2002 | Williams et al. | |
| 6,492,368 B1 | 12/2002 | Dorsch et al. | |
| 6,511,977 B1 | 1/2003 | Lloyd et al. | |
| 6,723,730 B2 | 4/2004 | Bakthavatchalam et al. | |
| 6,818,631 B1 | 11/2004 | Nakagawa et al. | |
| 6,979,675 B2 | 12/2005 | Tidmarsh | |
| 7,173,025 B1 | 2/2007 | Stocker et al. | |
| 7,288,554 B2 | 10/2007 | Finkelstein et al. | |
| 7,524,848 B2 | 4/2009 | Powers et al. | |
| 7,572,913 B2 | 8/2009 | McKerracher et al. | |
| 7,615,553 B2 | 11/2009 | Van Emelen et al. | |
| 7,858,782 B2 | 12/2010 | Tao et al. | |
| 7,863,444 B2 | 1/2011 | Calderwood et al. | |
| 8,058,313 B2 | 11/2011 | Reddy et al. | |
| 8,133,900 B2 | 3/2012 | Hood et al. | |
| 8,465,673 B2 | 6/2013 | Yasuda et al. | |
| 8,642,660 B2 | 2/2014 | Goldfarb | |
| 8,742,119 B2 | 6/2014 | Salituro et al. | |
| 8,785,450 B2 | 7/2014 | Salituro et al. | |
| 8,889,667 B2 | 11/2014 | Salituro et al. | |
| 9,193,701 B2 | 11/2015 | Su | |
| 9,199,968 B2 | 12/2015 | Salituro et al. | |
| 9,404,081 B2 | 8/2016 | Su | |
| 9,682,080 B2 | 6/2017 | Su | |
| 9,980,961 B2 | 5/2018 | Su et al. | |
| 10,029,987 B2 | 7/2018 | Salituro et al. | |
| 10,632,114 B2 | 4/2020 | Su et al. | |
| 11,793,806 B2 * | 10/2023 | Su | A61P 7/06 |
| 2002/0188027 A1 | 12/2002 | Robinson et al. | |
| 2003/0082877 A1 | 5/2003 | Ootsuka et al. | |
| 2003/0095958 A1 | 5/2003 | Bhisetti et al. | |
| 2003/0106381 A1 | 6/2003 | Krouth et al. | |
| 2003/0109527 A1 | 6/2003 | Jin et al. | |
| 2003/0158232 A1 | 8/2003 | Cheng et al. | |
| 2003/0187001 A1 | 10/2003 | Calderwood et al. | |
| 2003/0207882 A1 | 11/2003 | Stocker et al. | |
| 2003/0213405 A1 | 11/2003 | Harada et al. | |
| 2004/0048283 A1 | 3/2004 | Pau et al. | |
| 2004/0067234 A1 | 4/2004 | Einat et al. | |
| 2004/0152648 A1 | 8/2004 | Ullrich et al. | |
| 2004/0198979 A1 | 10/2004 | Dhanak et al. | |
| 2004/0235755 A1 | 11/2004 | Eigenbrodt et al. | |
| 2004/0248221 A1 | 12/2004 | Stockwell | |
| 2005/0176675 A1 | 8/2005 | Gomy | |
| 2006/0084645 A1 | 4/2006 | Pal et al. | |
| 2006/0281122 A1 | 12/2006 | Bryant et al. | |
| 2007/0032418 A1 | 2/2007 | Shapiro et al. | |
| 2007/0127505 A1 | 6/2007 | Laurila et al. | |
| 2007/0244088 A1 | 10/2007 | Brickmann et al. | |
| 2007/0280918 A1 | 12/2007 | Schwartz et al. | |
| 2008/0004269 A1 | 1/2008 | Xu et al. | |
| 2008/0021116 A1 | 1/2008 | Ullrich et al. | |
| 2008/0044833 A1 | 2/2008 | Connors | |
| 2008/0051414 A1 | 2/2008 | Hurley et al. | |
| 2008/0214495 A1 | 9/2008 | Alstermark et al. | |
| 2008/0300208 A1 | 12/2008 | Einat et al. | |
| 2009/0048227 A1 | 2/2009 | Chakravarty et al. | |
| 2009/0054453 A1 | 2/2009 | Alcaraz et al. | |
| 2009/0093526 A1 | 4/2009 | Miller et al. | |
| 2009/0163508 A1 | 6/2009 | Kori et al. | |
| 2009/0163545 A1 | 6/2009 | Goldfarb | |
| 2009/0247499 A1 | 10/2009 | Fletcher et al. | |
| 2009/0263826 A1 | 10/2009 | Walk et al. | |
| 2009/0270454 A1 | 10/2009 | Weingarten et al. | |
| 2010/0105657 A1 | 4/2010 | Nordvall et al. | |
| 2010/0129350 A1 | 5/2010 | Zacharie et al. | |
| 2010/0144722 A1 | 6/2010 | Alexander et al. | |
| 2010/0179150 A1 | 7/2010 | Basarab et al. | |
| 2010/0273808 A1 | 10/2010 | Armitage et al. | |
| 2010/0331307 A1 | 12/2010 | Salituro et al. | |
| 2011/0046083 A1 | 2/2011 | Cantley et al. | |
| 2011/0073007 A1 | 3/2011 | Yasuda et al. | |
| 2011/0086088 A1 | 4/2011 | Berry | |
| 2011/0224252 A1 | 9/2011 | Dumeunier et al. | |
| 2011/0288065 A1 | 11/2011 | Fujihara et al. | |
| 2011/0312931 A1 | 12/2011 | Cioffi et al. | |
| 2012/0121515 A1 | 5/2012 | Dang et al. | |
| 2012/0122885 A1 | 5/2012 | Salituro et al. | |
| 2012/0129865 A1 | 5/2012 | Wang et al. | |
| 2012/0164143 A1 | 6/2012 | Teeling et al. | |
| 2012/0172349 A1 | 7/2012 | Salituro et al. | |
| 2012/0202818 A1 | 8/2012 | Tao et al. | |
| 2012/0238576 A1 | 9/2012 | Tao et al. | |
| 2012/0277233 A1 | 11/2012 | Tao et al. | |
| 2013/0035329 A1 | 2/2013 | Saunders et al. | |
| 2013/0109643 A1 | 5/2013 | Riggins et al. | |
| 2013/0183281 A1 | 7/2013 | Su et al. | |
| 2013/0184222 A1 | 7/2013 | Popovici-Muller et al. | |
| 2013/0190249 A1 | 7/2013 | Lemieux et al. | |
| 2013/0190287 A1 | 7/2013 | Cianchetta et al. | |
| 2014/0155408 A1 | 6/2014 | Su | |
| 2014/0187435 A1 | 7/2014 | Dang et al. | |
| 2014/0194402 A1 | 7/2014 | Su | |
| 2014/0249150 A1 | 9/2014 | Kung | |
| 2014/0323467 A1 | 10/2014 | Salituro et al. | |
| 2014/0323729 A1 | 10/2014 | Salituro et al. | |
| 2015/0018328 A1 | 1/2015 | Konteatis et al. | |
| 2015/0031627 A1 | 1/2015 | Lemieux et al. | |
| 2015/0044716 A1 | 2/2015 | Balss et al. | |
| 2015/0183760 A1 | 7/2015 | Salituro et al. | |
| 2016/0106742 A1 | 4/2016 | Su | |
| 2017/0166541 A1 | 6/2017 | Saunders et al. | |
| 2017/0183311 A1 | 6/2017 | Salituro et al. | |
| 2017/0290825 A1 | 10/2017 | Su | |
| 2019/0345109 A1 | 11/2019 | Salituro et al. | |
| 2020/0030322 A1 | 1/2020 | Agresta et al. | |

FOREIGN PATENT DOCUMENTS

| | | |
|---|---|---|
| CN | 102659765 A | 9/2012 |
| CN | 103097340 A | 5/2013 |
| DE | 3314663 A1 | 10/1983 |
| DE | 3512630 A1 | 10/1986 |
| DE | 3813886 A1 | 11/1989 |
| DE | 19841985 A1 | 3/2000 |
| EP | 0022958 A1 | 1/1981 |
| EP | 0189069 A2 | 7/1986 |
| EP | 0246749 A2 | 11/1987 |
| EP | 0384228 A1 | 8/1990 |
| EP | 0385237 A2 | 9/1990 |
| EP | 0628551 A1 | 12/1994 |
| EP | 0945446 A1 | 9/1999 |
| EP | 1586558 A2 | 10/2005 |

(56) References Cited

FOREIGN PATENT DOCUMENTS

| | | | |
|---|---|---|---|
| FR | 2735127 A1 | 12/1996 |
| GB | 1274436 A | 5/1972 |
| IN | 101575408 A | 11/2009 |
| IT | 1176770 B | 8/1987 |
| JP | S61129129 A | 6/1986 |
| JP | H04099768 A | 3/1992 |
| JP | H06-025177 A | 2/1994 |
| JP | H07165708 A | 6/1995 |
| JP | H9291034 A | 11/1997 |
| JP | H11158073 A | 6/1999 |
| JP | 2002193710 A | 7/2002 |
| JP | 2004107220 A | 4/2004 |
| JP | 2007238458 A | 9/2007 |
| JP | 2008514590 A | 5/2008 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2014509458 A | 4/2014 |
| JP | 2014509459 A | 4/2014 |
| WO | 8501289 A1 | 3/1985 |
| WO | 1992011761 A1 | 7/1992 |
| WO | 9313072 A1 | 7/1993 |
| WO | 1996030343 A1 | 10/1996 |
| WO | 9728128 A1 | 8/1997 |
| WO | 9728129 A1 | 8/1997 |
| WO | 9728141 A1 | 8/1997 |
| WO | 1997044322 A1 | 11/1997 |
| WO | 9803350 A1 | 1/1998 |
| WO | 199916751 A1 | 4/1999 |
| WO | 9932463 A1 | 7/1999 |
| WO | 1999048490 A1 | 9/1999 |
| WO | 990062506 A1 | 12/1999 |
| WO | 2000017202 A1 | 3/2000 |
| WO | 0053596 A2 | 9/2000 |
| WO | 0107440 A1 | 2/2001 |
| WO | 2001016097 A1 | 3/2001 |
| WO | 2001019788 A2 | 3/2001 |
| WO | 2001019798 A2 | 3/2001 |
| WO | 2001064642 A2 | 9/2001 |
| WO | 2001064643 A2 | 9/2001 |
| WO | 2002072077 A2 | 9/2002 |
| WO | 02095063 A1 | 11/2002 |
| WO | 2002/102313 A2 | 12/2002 |
| WO | 2002100822 A1 | 12/2002 |
| WO | 030016289 A1 | 2/2003 |
| WO | 0322277 A1 | 3/2003 |
| WO | 03037252 A2 | 5/2003 |
| WO | 03062235 A1 | 7/2003 |
| WO | 03076422 A1 | 9/2003 |
| WO | 2003073999 A2 | 9/2003 |
| WO | 03/093297 A2 | 11/2003 |
| WO | 2004004730 A2 | 1/2004 |
| WO | 2004009562 A1 | 1/2004 |
| WO | 2004014851 A2 | 2/2004 |
| WO | 2004037251 A1 | 5/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2004110375 A2 | 12/2004 |
| WO | 2005035507 A2 | 4/2005 |
| WO | 2005/065691 A1 | 7/2005 |
| WO | 2005060956 A1 | 7/2005 |
| WO | 2005072642 A1 | 8/2005 |
| WO | 2005117591 A2 | 12/2005 |
| WO | 2005120474 A2 | 12/2005 |
| WO | 2006004195 A1 | 1/2006 |
| WO | 2006016062 A1 | 2/2006 |
| WO | 2006033628 A1 | 3/2006 |
| WO | 2006034341 A2 | 3/2006 |
| WO | 2006038594 A1 | 4/2006 |
| WO | 2006043950 A1 | 4/2006 |
| WO | 2006/052190 A1 | 5/2006 |
| WO | 2006063294 A2 | 6/2006 |
| WO | 2006070198 A1 | 7/2006 |
| WO | 2006077821 A1 | 7/2006 |
| WO | 2006079791 A1 | 8/2006 |
| WO | 2006117762 A2 | 11/2006 |
| WO | 2006122546 A1 | 11/2006 |
| WO | 2007003934 A2 | 1/2007 |
| WO | 2007023186 A1 | 3/2007 |
| WO | 2007117465 A2 | 10/2007 |
| WO | 2007127505 A2 | 11/2007 |
| WO | 2008019139 A2 | 2/2008 |
| WO | 2008024284 A2 | 2/2008 |
| WO | 2008026658 A1 | 3/2008 |
| WO | 2008047198 A1 | 4/2008 |
| WO | 2008050168 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009012430 A1 | 1/2009 |
| WO | 2009013126 A1 | 1/2009 |
| WO | 2009016410 A2 | 2/2009 |
| WO | 2009025781 A1 | 2/2009 |
| WO | 2009053102 A1 | 4/2009 |
| WO | 2009086303 A2 | 7/2009 |
| WO | 2009/126863 A2 | 10/2009 |
| WO | 2009118567 A2 | 10/2009 |
| WO | 2009150248 A1 | 12/2009 |
| WO | 2010007756 A1 | 1/2010 |
| WO | 2010023445 A1 | 3/2010 |
| WO | 2010028099 A1 | 3/2010 |
| WO | 2010042867 A2 | 4/2010 |
| WO | 2010105243 A1 | 9/2010 |
| WO | 2010118063 A2 | 10/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 2011002816 A1 | 1/2011 |
| WO | 2011002817 A1 | 1/2011 |
| WO | 2011032169 A2 | 3/2011 |
| WO | 2011047432 A1 | 4/2011 |
| WO | 2011050210 A1 | 4/2011 |
| WO | 2011072174 A1 | 6/2011 |
| WO | 2011109441 A1 | 9/2011 |
| WO | 2011137089 A1 | 11/2011 |
| WO | 2012/009678 A1 | 1/2012 |
| WO | 2012069503 A1 | 5/2012 |
| WO | 2012074999 A1 | 6/2012 |
| WO | 2012092442 A1 | 7/2012 |
| WO | 2012151451 A1 | 11/2012 |
| WO | 2012151452 A1 | 11/2012 |
| WO | 2012160034 A1 | 11/2012 |
| WO | 2012171506 A1 | 12/2012 |
| WO | 2013102431 A1 | 7/2013 |
| WO | 2013107291 A1 | 7/2013 |
| WO | 2013107405 A1 | 7/2013 |
| WO | 2013/133367 A1 | 9/2013 |
| WO | 2014015422 A1 | 1/2014 |

OTHER PUBLICATIONS

EP 10825706—EP Search Report Written Opinion, Mar. 20, 2013.
Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).
EP 10751525.6—European Search Report, Dec. 14, 2012.
EP 10794667.5—European Search report, Oct. 9, 2013.
EP 10794667.5—European Search Report, Apr. 9, 2014.
EP 11811257.2—European Search Report, Apr. 23, 2014.
EP 12799802.9—European Search Report, Sep. 24, 2014.
EP 12800001.5—European Search Report, Oct. 10, 2014.
EP 11763425.3—European Search Report, Sep. 23, 2013.
EP 07836571.5—Extended European Search Report, Sep. 29, 2010.
EP 16152308.9—Extended European Search Report, Jul. 18, 2016.

(56) References Cited

OTHER PUBLICATIONS

Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p. 4.
Friedman et al., "Leptin and the regulation of body weight in mammals" Nature. vol. 395, 1996.
Furuya et al., Inactivation of the 3-phosphoglycerate dehydrogenase gene in mice: changes in gene expression and associated regulatory networks resulting from serine deficiency. Funct Integr Genomics (2008) 8:235-249.
Ge et al. "Anaplasma phagocytophilum inhibits human neutrophil apoptosis via upregulation of bfl-1, maintenance of mitochondrial membrane potential and prevention of caspase 3 activation." Cellular Microbiology, 2005, 7(1 ), 29-38.
Genetics Home Reference. "L2HGDH." accessed at <http://ghr.nlm.nih.gov/gene/L2HGDH> on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Gupta et al., "Dominant negative mutations affect oligomerisation of human pyruvate kinase M2 isozyme and promote cellular growth and polyploidy." J Biol Chem. (2010).
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
Holmes et al., 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Hua et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects," Database Biosis [Online], database accession No. PREV201500280858, vol. 124, No. 21, 56th Annual Meeting of the American Society-of-Hematology, San Francisco, CA, 2014.
Hulleman, et al., "Pyruvate kinase M2 and prednisolone resistance in acute lymphoblastic leukemia." Haematologica. Sep. 2009; 94(9): 1322-1324.
Inglese et al., "Quantitative high-throughput screening: A titration-based approach that efficiently identifies biological activities in large chemical libraries," Proc. Natl. Acad. Sci., 103 (31), 11473-11478 (2006).
PCT/US2010/059778—International Preliminary Report for related application, Jun. 21, 2012.
PCT/US2011/067752—International Preliminary Report for related application, Apr. 11, 2013.
PCT/US2007/017519—International Preliminary Report on patentability, Jul. 8, 2008.
PCT/CN2012/000841—International Preliminary Report on Patentability, Dec. 17, 2013.
PCT/CN2012/077096—International Preliminary Report on Patentability, Dec. 17, 2013.
PCT/US2008/009828—International Preliminary Report on Patentability, Feb. 16, 2010.
PCT/US2010/027253—International Preliminary Report on Patentability, Sep. 13, 2011.
PCT/US2010/040486—International Preliminary Report on Patentability, Jan. 12, 2012.
PCT/US2010/053623—International Preliminary Report on Patentability, Apr. 24, 2012.
PCT/US2010/053624—International Preliminary Report on Patentability, Apr. 7, 2011.
PCT/US2011/030692—International Preliminary Report on Patentability, Oct. 2, 2012.
PCT/US2009/060237—International Preliminary Report on Patentability, dated Apr. 12, 2011.
PCT/CN2013/070755—International Search Report & Written Opinion, Apr. 25, 2013.
PCT/US2010/030139—International Search Report & Written Opinion, Dec. 10, 2010.
PCT/US2010/040485—International Search Report & Written Opinion, Aug. 11, 2010.
PCT/US2007/017519—International Search Report and the Written Opinion, Jul. 8, 2008.
PCT/US2013/064601—International Search Report and Written Opinion, Feb. 24, 2014.
PCT/CN2013/080105—International Search Report and Written Opinion, Jul. 11, 2014.
PCT/CN2013/081170—International Search Report and Written Opinion, Apr. 30, 2014.
PCT/CN2014/081957—International Search Report and Written Opinion, Sep. 30, 2014.
PCT/CN2014/081958—International Search Report and Written Opinion, Sep. 29, 2014.
PCT/US2015/020349—International Search Report and Written Opinion, Jun. 15, 2015.
PCT/US2012/036412—International Search Report and Written Opinion, Jul. 6, 2012.
Lee, "Consolidation Effect of Phenylalanine-administration of Antitumor Activity of A 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Li et al., "Quantitative proteome analysis of multidrug resistance in human ovarian cancer cell line." J Cell Biochem.; 109(4):625-33 (2010).
Li et al., "Screening and identification of interactive proteins of SH2D4A." Yi Chuan.; 32(7):712-8 (2010). (Abstract Only).
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou. "IDH1: function follows form." SciBX, 2009, 1-2.
Luo et al. "Synthesis and Fungicidal Activity of N-Benzo[b][1,4]oxazin-6-yl-2,4-dimethylthiazole-5-carboxamides" Agrochemicals (2009) vol. 48, No. 1, pp. 19-22.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Marry et al. "Human Biochemistry," Moscow, Mir, 1993, chapter 18.
Mass, R. D., "The HER receptor family: a rich target for therapeutic development", Int. J. Radiation Oncology Bio. Phys.vol. 58(3): 932-940, 2004.
May et al, How many species are there on earth, Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Morshed et al. "Computational approach to the identification of novel Aurora-A inhibitors" Bioorganic & Medicinal Chemistry (2011) vol. 19, No. 2, pp. 907-916.
Oeda, "On some 2,5-Dialikl-piperazines," Bull. Chem. Soc., 13, 465-470 (1938).

(56) References Cited

OTHER PUBLICATIONS

Pan et al. "Research Status of Pyruvate Deficiency" Chinese Journal of Hematology (1999) vol. 20, No. 4, pp. 223.
Park, "Prevention of type 2 diabetes mellitus from the viewpoint of genetics." Diabetes Research and Clinical Practice 2004; 66S: S33-S35.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science vol. 321 (2008) pp. 1807-1812 and Supplemental Data.
Patel et al. "Synthesis of some new idolinone derivatives containing piperazine moiety" Bulgarian Chemical Communications, 2003 Bol 35 No. 4 pp. 242-244.
Paudler et al., "3,7-Disubstituted octahydro-1,5-diazocines. Their conversion into tetrahydro-1,5-diazocines and into ring-contracted products," J. Org. Chem., 32 (8), 2425-2430 (1967).
Petz et al. "Increased IgG Molecules Bound to the Surface of Red Blood Cells of Patients With Sickle Cell Anemia" Blood (1984) vol. 64, No. 1, pp. 301-304.
Pollard et al., "Some Amides of Piperazines," J. Am. Chem. Soc., 75 (2), 491 (1953).
Pollard et al, "Cancer. Puzzling patterns of predisposition." Science. Apr. 10, 2009, vol. 324, 1-5,15-16, 18-22,35-38 No 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
Proisy et al. "Rapid Synthesis of 3-Aminoisoquinoline-5-sulfonamides Using the Buchwald-Hartwig Reaction" Synthesis 2009, No. 4, pp. 0561-0566.
PUBCHEM CID 4078245 [online]; Sep. 13, 2005 [retrieved on Feb. 4, 2012]; retrieved from http://pubchem.ncbi.nim.nih.gov/; 2d-structure.
PUBCHEM CID 4854170 [online]; Sep. 17, 2005 [retrieved on Feb. 4, 2012]; retrieved from http://pubchem.ncbi.nim.nih.gov/; 2d-structure.
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Remington's, "Structure Activity Relationship and Drug Design," Pharmaceutical Sciences, pp. 420-425p. 420-425, 1980.
Rich, et. al., "Development of novel targeted therapies in the treatment of malignant glioma" Nature Rev. Drug Disc., Nature Publishing Group, vol. 3, pp. 430-446, 2004.
Rohle et al. "An Inhibitor of Mutant IDH1 Delays Growth and Promotes Differentiation of Glioma Cells" Science, vol. 340, No. 6132 pp. 626-630 (2013).
Root et al., "Genome-Scale Loss-of-Function Screening with a Lentiviral RNAi Library," Nat Methods 3: 715-719 (2006).
Ruan et al., "HSP60, a protein downregulated by IGFBP7 in colorectal carcinoma." J Exp Clin Cancer Res.;29:41 (2010).
Sabatine et al., "Metabolomic Identification of Novel Biomarkers of Myocardial Ischemia," Circulation 112: 3868-3875 (2005).
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1,4-diazepinen," Zeitschrift Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-I-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters 92004 volume 557, pp. 115-120.
Struys et al. "Mutations in the D-2-hydroxyglutarate dehydrogenase gene cause D-2-hydroxyglutaric aciduria" American Journal of Human Genetics, 2005. 76:358-360.
Struys, EA et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.
Supplemental EP Search Report & Written Opinion for EP 10 79 4667 dated Jan. 15, 2013.
Supplemental EP Search Report for European Application No. 10714131.9 dated Oct. 17, 2014.
Supplementary European Search Report for EP Application No. 10825707.2 dated Jun. 28, 2013.
Supplementary Search Report for EP10794668 Mailed Oct. 18, 2012.
Supplimentary European Search Report for EP 10751525 Mailed Dec. 14, 2012.
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes )," Ann. Rev. Biophys. Bioeng., 9, 467-508 (1980).
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
Takashi Yamaoka, Adenosine deaminase hyperkinasia, Nihon Rinsho (supplementary volume) series of Syndrome for each area 20 Blood Syndrome I, Aug. 12, 1998, p. 308-311.
Tawaka, et al., Caplus an 1998:794998.

(56) References Cited

OTHER PUBLICATIONS

The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Uozumi et al., "Catalytic asymmetric construction of morpholines and piperazines by palladium-catalyzed tandem allylic substitution reactions," J. Org. Chem., 58 (24), 6826-6832 (1993).
Van Schaftingen et al. "L-2-Hydroglutaric aciduria, a disorder of metabolite repair" J Inherit. Metab. Dis. (2009) vol. 32, pp. 135-142.
Vander Heiden et al., "Growth Factors Can Influence Cell Growth and Survival Through Effects on Glucose Metabolism," Mol Cell Bioi. 21: 5899-5912 (2001).
Vander Heiden et al., "Identification of Small Molecule Inhibitors of Pyruvate Kinase M2," Biochemical Pharmacology. 79(8): 1118-1124 (2010).
VanElemen et al, Caplus am 2003:737742.
Villen et al., "Large-Scale Phosphorylation Analysis of Mouse Liver," Proc Nat! Acad Sci USA 104: 1488-1493 (2007).
Villoutreix et al., Caplus an 2010:20993.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Wang et al. "A novel ligand N, N?- di(2-pyridyl)-2,4-diamino-6-phenyl-1,3,5-triazine (dpdapt) and its complexes: [Cu(dpdapt)CI2] and [Cu(dpdapt)(NO3)(H2O)] Â• NO3 Â• H2O" Polyhedron, 2006. Vol 25, Issue 1. pp 195-202.
Ward, Patrick S, "The Common Feature of Leukemia-Associated IDH1 and IDH2 Mutations Is a Neomorphic Enzyme Activity Converting [alpha]-Ketoglutarate to 2-Hydroxyglutarate" Cancer cell, vol. 17,Nr:3,pp. 225-234, 2010.
Watanabe et al., "IDH1 Mutations Are Early Events in the Development of Astrocytomas and Oligodendrogliomas". American Journal of Pathology, Apr. 2009 (published online Feb. 26, 2009), vol. 174, No. 4, pp. 1149-1153; Abstract, p. 1150, col. 1.
Web posting, Pyruvate kinase M2 isozyme (PKM2), SciBX 5(42), Published online Oct. 25, 2012, Abstract only.
Wong et al. "PKM2, a Central Point of Regulation in Cancer Metabolism" International Journal of Cell Biology (2013) vol. 2013, pp. 1-11.
Written Opinion for PCT/US2010/027253 mailed Aug. 19, 2010.
Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2008/009828, dated Dec. 5, 2008.
Written Opinion of the International Searching Authority for PCT/US2011/067752 dated Mar. 5, 2012.
Yamada and Noguchi, "Nutrient and Hormonal Regulation of Pyruvate Kinase Gene Expression," Biochem J. 337:1-11 (1999).
Yan et al., "IDH1 and IDH2 Mutations in Gliomas." The New England Journal of Medicine, 19 Feb. 18-22, 2009, vol. 360, No. 8, pp. 765-773.
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20), 3784-3786 (2008).
Ye et al., Pyruvate kinase M2 promotes de novo serine synthesis to sustain mTORC1 activity and cell proliferation, PNAS 109(18), 2012, pp. 6904-6909.
Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Imai et al. "Comparing antibody and small-molecule therapies for cancer", Nature Publishing Group. 2006; vol. 6.
Chung et al. "Discovery and Characterization of small molecule inhibitors of he BET family bromodomains", J. Med. Chem. 2011, 54, pp. 3827-3838.
Promacta Label, 2008 (revised Dec. 2011).
Hoelder et al. "Discovery of small molecule cancer drugs: Successes, challenges and opportunities", Molecular Oncology 6 (2012) pp. 155-176.
Reichert, "Trends in development and approval times for new therapeutics in the United States", Nature Reviews, vol. 2 (2003) p. 695.
"Pyruvate Kinase Deficiency Natural History Study," ClinicalTrials.gov, 2014, 1-7.
Yang et al. "Phase I Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers," Clinical Pharmacology in Drug Development, 2018, 00(0):1-14.
Yang et al. "Phase I Single (SAD) and Multiple Ascending Dose (MAD) Studies of the Safety, Tolerability, Pharmacokinetics (PK) and Pharmacodynamics (PD) of AG-348, a First-in-Class Allosteric Activator of Pyruvate Kinase-R, in Healthy Subjects," Blood, 2014, 124(21):1-3.
Pushkareva T.I. et al., "Hemolytic anemias", study guide, Blagoveshchensk, 2010, (56 pages w/translation).
Hemolytic anemia—treatment in Moscow, https://www.krasotaimedicina.ru/diseases/hematologic/hemolytic-anemia##h2_27, Apr. 23, 2009, 3 pages w/translation.
PCT/US2012/036413—International Search Report and Written Opinion, Jul. 6, 2012.
PCT/US2014/046202—International Search Report and Written Opinion, Sep. 30, 2014.
PCT/US2014/049469—International Search Report and Written Opinion, Jan. 22, 2015.
PCT/US2015/020346—International Search Report and Written Opinion, Jun. 18, 2015.
PCT/US2011/065633—International Search Report, Apr. 4, 2012 for related Application.
PCT/US2011/067752—International Search Report, Mar. 5, 2012.
PCT/US2011/066595—International Search Report, for related application.
PCT/US2012/060099—International Search Report, Jan. 8, 2013.
PCT/CN2013/079184—International Search Report, Jan. 12, 2015.
PCT/CN2013/079200—International Search Report, Jan. 12, 2015.
PCT/CN2014/082869—International Search Report, Sep. 30, 2014.
PCT/US2014/046204—International Search Report, Oct. 1, 2014.
PCT/CN2012/000841—International Search Report, Sep. 27, 2012.
PCT/CN2012/077096—International Search Report, Oct. 4, 2012.
PCT/CN2013/000009—International Search Report, Apr. 18, 2013.
PCT/CN2013/000068—International Search Report, Apr. 25, 2013.
PCT/US2010/040486—International Search Report, Sep. 1, 2010.
PCT/US2008/009828—International Search Report, Dec. 5, 2008.
PCT/US2011/030692—International Search Report, Jul. 27, 2011.
PCT/US2010/027253—International Search Report, Aug. 19, 2010.
PCT/US2010/033610—International Search Report, Jul. 22, 2010.
PCT/US2010/059778—International Search Report, Mar. 17, 2011.
PCT/US2010/053623—International Search Report, Jan. 18, 2011.
PCT/US2010/053624—International Search Report, Apr. 7, 2011.
PCT/US2011/065633—International Search Report, Jun. 18, 2013.
PCT/US2011/044254—International Search Report, May 10, 2011.
PCT/US2013/064601—International Search Report, Feb. 24, 2014.
PCT/US2009/060237—International Search Report, Jun. 16, 2010.
PCT/US2011/033852—International Search Report, Aug. 3, 2011.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.

(56) References Cited

OTHER PUBLICATIONS

Jennings et al, Expression and mutagenesis of mammalian cytosolic NADP+-specific isocitrate dehydrogenase, Biochemistry (1997)vol. 36, pp. 13743-13747.
Jiang et al., "Evaluation of thieno[3,2-b]pyrrole[3,2-d]pyridazinones as activators of the tumor cell specific M2 isoform of pyruvate kinase." Bioorg. Med. Chem. Lett., 20 (11), 3387-3393 (2010).
Joshi et al., "Age-related faecal calprotectin, lactoferrin and tumour M2-PK concentrations in healthy volunteers." Ann Clin Biochem.; 47(Pt 3):259-63 (2010).
Jurica et al., "The Allosteric Regulation of Pyruvate Kinase by Fructose-1,6-Bisphosphate," Structure 6: 195-210 (1998).
Kaila et al. "A convenient one-pot synthesis of trisubstituted 1,3,5-triazines through intermediary amidinothioureas" Tetrahedron Letters (2010) vol. 51, pp. 1486-1489.
Kao et al., "A Small-Molecule Inhibitor of the Ribonucleolytic Activity of Human Angiogenin That Possesses Antitumor Activity," Proc. Nat!. Acad. Sci. USA, 99(15): 10066-10071 (2002).
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kharalkar et al., "Identification of Novel Allosteric Regulators of Human-Erythrocyte Pyruvate Kinase," Chem Biodivers. 4: 2603-2617 (2007).
Kim et al "Ser95, Asn97, and Thr78 are important for the catalytic function of porcine NADP-dependent isocitrate dehydrogenase" Protein Science (2005) 14: pp. 140-147.
Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al., "In vivo factors influencing tumour M2-pyruvate kinase level in human pancreatic cancer cell lines." Tumour Biol. ;31(2):69-77 (2010).
Kumiko Tsujino et al., "CBA-Pk-1slc/Pk-1slcmutant mouse in Newborn period does not exhibit hemolytic anemia," Japanese Society of Animal Models for Human Diseases, 1998, vol. 14, p. 24.
Kung et al. "Small Molecule Activation of PKM2 in Cancer Cells Induces Serine Auxotrophy" Chemistry & Biology, 19, 1187-1198, Sep. 21, 2012.
Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Lee et al. "Combinatorial Solid-Phase Synthesis of 6-Aryl-1,3,4-triazines via Suzuki Coupling" Aust. J. Chem. (2011) vol. 64, pp. 540-544.
Shih et al. "The Role of Mutations in Epigenetic Regulators in Myeloid Malignancies" Nature Reviews Cancer (2012) vol. 12, No. 9, pp. 599-612.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Stewart et al., "Piperazines. I. Derivatives of Piperazine-1-Carboxylic and -1,4-Dicarboxylic Acid,", J. Org. Chern., 18 (1), 1478-1483 (1953).
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry Number 134538-28-6, entered STN on Jun. 28, 1991, Chemical Abstracts Index Name "1H-Pyrano[3,4-c]pyridine-5-carbonitrile, 3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry Number 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry Number 134538-30-0, entered STN on Jun. 28, 1991, Chemical Abstracts Index Name "1H-Pyrano[3,4-c]pyridine-5-carbonitrile, 6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry Number 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available though Key Organics (under the BIONET brand) Jan. 1994.
STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available though Key Organics (under the BIONET brand) Jan. 1994.
STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available though Key Organics (under the BIONET brand) Jan. 1994.
STN File CA, Registry No. 321433-68-5, entered STN on Feb. 12, 2001, Chemical Abstracts Index Name "1H-Pyrrole-2-sulfonamide, 1-[3-chloro-5-(trifluoromethyl)-2-pyridinyl]-N-propyl" Available though Key Organics (under the BIONET brand) Jan. 1994.
STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available though Key Organics (under the BIONET brand) Jan. 1994.
STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyl" Available though Key Organics (under the BIONET brand) Feb. 1993.
STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available though Key Organics (under the BIONET brand) Feb. 1993.
STN File CA, Registry No. 338397-96-9, entered STN on May 25, 2001, Chemical Abstracts Index Name "1H-Pyrrole-2-sulfonic acid, 1-[3-chloro-5-(trifluoromethyl)-2-pyridinyl]-4-chlorophenyl ester" Available though Key Organics (under the BIONET brand) Feb. 1993.
STN File CA, Registry No. 338406-58-9, entered STN on May 25, 2001, Chemical Abstracts Index Name "1H-Pyrrole-2-sulfonamide,

(56) References Cited

OTHER PUBLICATIONS

1-[3-chloro-5-(trifluoromethyl)-2-pyridinyl]-N-[2-(trifluoromethyl)phenyl]" Available though Key Organics (under the BIONET brand) Mar. 1993.
STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available though Key Organics (under the BIONET brand) Mar. 1993.
STN File CA, Registry No. 338406-72-7, entered STN on May 25, 2001, Chemical Abstracts Index Name "1H-Pyrrole-2-sulfonamide, N-[(4-chlorophenyl)methyl]-1-[3-chloro-5-(trifluoromethyl)-2-pyridinyl]" Available though Key Organics (under the BIONET brand) Mar. 1993.
STN File CA, Registry No. 338407-11-7, entered STN on May 25, 2001, Chemical Abstracts Index Name "1H=Pyrrole-2-sulfonamide, 1-[3-chloro-5-(trifluoromethyl)-2-pyridinyl]-N-[3-chloro-4-[[5-(trifluoromethyl)-2-pyridinyl]oxy]phenyl]" Available though Key Organics (under the BIONET brand) Mar. 1993.
STN File CA, Registry No. 338407-13-9, entered STN on May 25, 2001, Chemical Abstracts Index Name "Benzoic acid, 3-[[[1-[3-chloro-5-(trifluoromethyl)-2-pyridinyl]-1H-pyrrol-2-yl]sulfonyl]amino]" Available though Key Organics (under the BIONET brand) Mar. 1993.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 OF 3 (Cas No. 1032450-21-7), Database: ASINEX Ltd., Entered STN: Jul. 3, 2008 (Jul. 3, 2008).
STN Registry. L23 Answer 1 OF 3 (Cas No. 1038821-72-5),Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-I-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-I-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-I-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4[[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-I-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
Aghili et al. "Hydroxyglutaric aciduria and malignant brain tumor: a case report and literature review", Journal of Neuroncology, 2008. 91:233-236.
Anastasiou et al. "Pyruvate kinase M2 activators promote tetramer formation and suppress tumorigenesis," Nature Chemical Biology, 2012, 8(10):839-847.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Avdeenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.
Balss, "Analysis of the IDH1 codon 132 mutation in brain tumors", Acata Neuropathol (2008) vol. 116, pp. 597-602.
Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970 (Jan. 1, 1970), pp. 850-853.
Behun et al., "The Chemistry of Pyrazine and Its Derivatives. IV. The Alkylation and Arylation of Methylpyrazine," J Org. Chern., 26 (9),3379-3382 (1961).

(56) References Cited

OTHER PUBLICATIONS

Benesch et al., "The clinicopathological and prognostic relevance of pyruvate kinase M2 and pAkt expression in breast cancer." Anticancer Res.;30(5):1689-94 (2010).
Benner et al, "Evolution, language and analogy in functional genomics", Trends in Genetics (2001) vol. 17, pp. 414-418.
Berger, et. al., "Treatment of Pancreatic Cancer: Challenge of the Facts" World J. Surg., Societe Internationale de Chirurgie, vol. 27, pp. 1075-1083, 2003.
Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p.R132 (IDH1 (R132)) occur frequently in high-grade 18-22 gliomas but not in other solid tumors." Hum Mutal., Jan. 2009, vol. 30, No. 1, pp. 7-11.
Bonuccelli et al., "The reverse Warburg effect: Glycolysis inhibitors prevent the tumor promoting effects of caveolin-1 deficient cancer associated fibroblasts." Cell Cycle.;9(10) (2010).
Boxer, et al., "Evaluation of Substituted N, N?-Diarylsulfonamides as Activators of the Tumor Cell Specific M2 Isoform of Pyruvate Kinase", J Med Chem. Feb. 11, 2010; 53(3): 1048.
Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).
Braun et al. "Triazine-based polymers: 4. MALDI-MS of triazine-based polyamines" Polymer (1996) vol. 37, No. 5, pp. 777-783.
Budinger et al., "Cellular Energy Utilization and Supply During Hypoxia in Embryonic Cardiac Myocytes," Am J Physiol. 270: L44-53 (1996).
Buschow et al., "MHC class II-associated proteins in B-cell exosomes and potential functional implications for exosome biogenesis." Immunol Cell Biol. (2010).
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Textbook of Medicine, edited by Bennet, J.C., and Plum F., 20th edition, vol. 1, 1004-1010, 1996.
Chabner, et al., "Chemotherapy and the war on cancer", Nature Rev. Cancer, Nature Publishing Group, vol. 5, pp. 65-72, 2005.
Chan et al., "Synthesis and characterization of poly(amide sulfonamide)s (PASAs)," J Polymer. Sci., 33 (15), 2525-2531 (1995).
Chan et al. "Multi-domain hydrogen-bond forming metal chelates: X-ray crystal structuresof dicyclopalladated 2,3-bis [6-(2-amino-4-phenylamino-1 ,3,5-triazinyl)]pyrazine(H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitorsshow activity against Mycobacterium tuberculosis" Bioorganic & Medicinal Chemistry Letters (2012) vol. 22, pp. 3349-3353.
Charache et al. "Effect of 2,3-Diphosphoglycerate on Oxygen Affinity of Blood in Sickle Cell Anemia" Journal of Clinical Investigation (1970) vol. 49, pp. 806-812.
Charles et al. "AG-348 activation of pyruvate in vivo enhances red cell glycolosis in mice," Database Biosis [Online], database accession No. PREV201500280942, vol. 124, No. 21, 56th Annual Meeting of the American Society of Hematology, San Francisco, CA, 2014.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Christofk et al., "Pyruvate Kinase M2 is a Phosphotyrosine-Binding Protein," Nature 452: 181-186 (2008).
Christofk et al. , "The M2 Splice Isoform of Pyruvate Kinase is Important for Cancer Metabolism and Tumour Growth," Nature 452: 230-233 (2008).
Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.
Cocco et al. "Synthesis of Triflouromethylated Pyridinecarbonitriles" Journal of Heterocyclic Chemistry, 1995. vol. 32 pp. 543-545.
Cohen et al., "The development and therapeutic potential of protein kinase inhibitors", Current Opinion in Chemical Biology, 3,459-465, 1999.
Cohen-Solal et al. "A new sickle cell disease phenotype associating Hb S trait, severe pyruvate kinase deficiency (PK Conakry), and an a2 globin gene varient (Hb Conakry)," British Journal of Haematology, 1998, 103:950-956.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
Crawford et al., Caplus an 2010:1218943.
Cuzick, et al., "Overview of the main outcomes in breast-cancer prevention trials" The Lancet, The Lancet Publishing Group, vol. 361, pp. 296-300, 2003.
Dang et al., "Cancer-associated IDH1 mutations produce 2-hydroxyglutarate." Nature, 10 29-32 Dec. 2009, vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Database Chemcats, Chemical Abstracts Service, Columbus, OH, US "Bionet Screening Compounds" Key Organics Ltd., Camelford, Cornwall (2001).
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Denhem et al. "Blood diseases in the elderly," Moscow, Medicine, 1989, chapter 15.
Dermer et al., "Another Anniversary for the War on Cancer", Bio/Technology, 1994, 12:320.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Dombrauckas, et al., Structural Basis for Tumor Pyruvate Kinasa M2 Allosteric Regulation and Catalysis, Biochemistry, vol. 44, p. 9717-9429 (2005).
Dong et al. "PKM2 and cancer: The function of PKM2 beyond glycolisis," Oncology Letters, 2016, 11:1980-1986.
Dong et al. "PKM2 and cancer: The function of PKM2 beyond glycolosis (Review)," Oncology Letters, 2016, 11:1980-1986.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).
Zacks Equity Research Jun. 10, 2014 (Year: 2014).
Tuntland et al. "Implementation of pharmacokinetic and pharmacodynamics strategies in early research phases of drug discovery and development at Novartis Institute of Biomedical Research," Frontiers in Pharmacology Jul. 28, 2014, p. 1-16 (Year: 2014).
FDA Guidance, "Exposure-Response Relationships—Study Design, Data Analysis, and Regulatory Applications," Apr. 2003. ( Year: 2003).

(56) References Cited

OTHER PUBLICATIONS

Kou et al., "Clinical Enzymology Assay", Jilin Medical College, Dec. 31, 1989, pp. 100-103.
Wang et al., "Diagnosis and Treatment of Practical Hematological Diseases", Military Medical Science Press, Jul. 31, 2008, p. 115-117.
Pu et al., "Handbook of Bone Marrow Pathology Diagnosis for Hematologic disease", Science Press, Jun. 30, 2003, pp. 94-95.
Li et al., "Outline of Medical Genetics", People's Medical Publishing House, Jun. 30, 1989, pp. 105-112.

\* cited by examiner

FIG. 1A

| Structure | % Act. R510Q | % Act. R532W | % Act. T384W | % Act. WT | PKR WT AC50 (μM) | PKR R510Q AC50 (μM) | PKR R532W AC50 (μM) | PKR T384W AC50 (μM) | PKR G332S AC50 (μM) | PKR G364D AC50 (μM) | PKR G37E AC50 (μM) | PKR R479H AC50 (μM) |
|---|---|---|---|---|---|---|---|---|---|---|---|---|
| [structure] | B | B | B | B | | | | | | | | |
| [structure] | B | B | B | B | | | | | | | | |
| [structure] | B | B | B | B | | | | | | | | |
| [structure] | B | B | B | B | | CC | BB | BB | | CC | | AA |
| [structure] | B | B | B | B | | | | | | | | |
| [structure] | B | B | B | B | AA | BB | AA | AA | BB | BB | CC | AA |
| [structure] | B | B | B | B | | | | | | | | |
| [structure] | B | B | B | B | | AA | AA | AA | | BB | | AA |
| [structure] | B | B | B | B | | | | | | | | |
| [structure] | B | B | B | B | | | | | | | | |
| [structure] | B | B | B | B | | BB | AA | AA | AA | BB | | AA |
| [structure] | B | B | B | B | AA | AA | AA | AA | CC | BB | | AA |
| [structure] | A | A | A | B | | | | | | | | |
| [structure] | B | B | B | B | | | | | | | | |
| [structure] | B | B | B | B | AA | AA | AA | AA | | | | |

FIG. 1B
| Structure | | | | | | | | | | | | |
|---|---|---|---|---|---|---|---|---|---|---|---|---|
|  | B | B | B | B | | | | | | | | |
|  | B | B | B | B | | | | | | | | |
|  | B | B | B | B | AA | AA | AA | AA | | | | |
|  | B | B | B | B | AA | AA | AA | AA | | | | |
|  | B | B | B | B | | | | | | | | |
|  | B | B | B | B | AA | BB | AA | AA | | | | |
|  | B | B | B | B | BB | CC | AA | BB | | | | |
|  | B | B | B | B | AA | AA | | | BB | | AA | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | A | | | | | | | | |
| 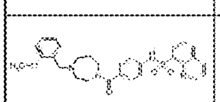 | A | B | A | B | | | | | | | | |
|  | B | B | B | B | | CC | | BB | AA | | | BB |

FIG. 1C

| Structure | | | | | | | | | | | | |
|---|---|---|---|---|---|---|---|---|---|---|---|---|
| (structure 1) | B | B | B | A | AA | BB | AA | AA | AA | BB | | AA |
| (structure 2) | B | B | B | B | | | | | | | | |
| (structure 3) | B | B | A | A | | | | | | | | |
| (structure 4) | B | B | B | B | | | | | | | | |
| (structure 5) | A | A | A | A | | | | | | | | |
| (structure 6) | B | B | B | B | | | | AA | BB | | AA |
| (structure 7) | B | A | A | A | CC | CC | | | CC | | CC |
| (structure 8) | B | B | A | B | | | | | | | | |
| (structure 9) | B | A | A | A | | | | | | | | |
| (structure 10) | B | B | B | B | | | | | | | | |
| (structure 11) | B | B | A | A | | | | | | | | |
| (structure 12) | A | B | A | B | | | | | | | | |
| (structure 13) | A | B | B | B | | | | | | | | |
| (structure 14) | B | B | B | B | | | | | | | | |
| (structure 15) | B | A | B | B | | | | | | | | |

FIG. 1D

| Structure | | | | | | | | | | | | | |
|---|---|---|---|---|---|---|---|---|---|---|---|---|---|
| | B | A | B | A | | | | | | | | | |
| | B | B | A | A | | | | | | | | | |
| | B | A | B | A | | | | | | | | | |
| | B | A | A | A | | | | | | | | | |
| | B | A | B | A | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | A | B | | | | | | | | | |
| | A | A | A | A | | | | | | | | | |
| | B | B | B | B | | | | | | | | | |
| | B | B | A | A | | | | | | | | | |
| | B | B | B | B | | | | | | | | | |
| | A | B | A | A | | | | | | | | | |

FIG. 1E

| Structure | | | | | | | | | | | | |
|---|---|---|---|---|---|---|---|---|---|---|---|---|
| | B | B | B | B | | | | | | | | |
| | B | B | B | B | | | | | | | | |
| | B | B | B | B | | | | | | | | |
| | B | A | A | A | | | | | | | | |
| | B | B | B | B | | | | | | | | |
| | B | B | B | B | | | | | | | | |
| 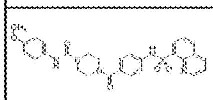 | A | B | B | A | | | | | | | | |
| | B | B | B | B | | | | | | | | |
| | B | B | B | B | | | | | | | | |
| | B | B | B | B | | | | | | | | |
| | B | B | B | B | | | | | | | | |
| | B | B | B | B | | | | | | | | |
| | B | A | A | A | | | | | | | | |
| | B | A | A | A | | | | | | | | |
| | B | A | A | A | | | | | | | | |

FIG. 1F

| Structure | | | | | | | | | | | |
|---|---|---|---|---|---|---|---|---|---|---|---|
| (structure 1) | B | A | A | A | | | | | | | |
| (structure 2) | B | A | A | A | | CC | BB | BB | BB | CC | | BB |
| (structure 3) | B | A | A | A | | | | | | | | |
| (structure 4) | B | A | A | A | | CC | AA | BB | CC | CC | CC | BB |
| (structure 5) | B | B | B | B | | | | | | | | |
| (structure 6) | B | B | B | B | | | | | | | | |
| (structure 7) | B | B | B | B | | | | | | | | |
| (structure 8) | B | B | B | B | | | | | | | | |
| (structure 9) | B | B | B | B | | | | | | | | |
| (structure 10) | A | B | B | B | | | | | | | | |
| (structure 11) | B | B | B | B | | | | | | | | |
| (structure 12) | A | B | B | B | | | | | | | | |
| (structure 13) | B | A | A | A | | | | | | | | |
| (structure 14) | B | A | B | B | | | | | | | | |
| (structure 15) | A | B | B | B | | | | | | | | |

FIG. 1G
| Structure | | | | | | | | | | | |
|---|---|---|---|---|---|---|---|---|---|---|---|
|  | B | B | B | B | | | | | | | |
|  | B | B | B | B | | | | | | | |
|  | A | A | B | B | | | | | | | |
|  | B | A | B | B | | | | | | | |
|  | A | B | B | B | | | | | | | |
|  | A | B | B | A | | | | | | | |
|  | B | B | B | B | | | | | | | |
|  | B | B | B | B | | | | | | | |
|  | A | B | A | A | AA | BB | AA | AA | | | |
|  | B | B | B | A | | | | | | | |
|  | B | B | B | B | | | | | | | |
|  | B | C | B | B | | | | | | | |
|  | B | B | B | B | | CC | CC | | | | |
|  | B | B | B | B | | | | | | | |
|  | B | B | B | B | | | | | | | |

FIG. 1H

| Structure | | | | | | | | | | | | | |
|---|---|---|---|---|---|---|---|---|---|---|---|---|---|
| [structure] | B | B | B | B | CC | | CC | | | | | | |
| [structure] | B | B | B | B | | | | | | | | | |
| [structure] | B | B | B | B | | | | | | | | | |
| [structure] | A | B | B | B | | | | | | | | | |
| [structure] | B | B | B | B | | | | | | | | | |
| [structure] | B | B | B | B | | | | | | | | | |
| [structure] | B | B | B | B | | | | | | | | | |
| [structure] | B | B | A | B | | | | | | | | | |
| [structure] | B | B | B | B | | | | | | | | | |
| [structure] | B | B | B | B | | | | | | | | | |
| [structure] | B | B | B | B | | | | | | | | | |
| [structure] | A | A | B | A | | | | | | | | | |
| [structure] | A | A | A | B | | | | | | | | | |
| [structure] | A | B | B | A | | | | | | | | | |
| [structure] | A | B | B | B | | | | | | | | | |

FIG. 1I

| Structure | 1 | 2 | 3 | 4 | 5 | 6 | 7 | 8 | 9 | 10 | 11 | 12 |
|---|---|---|---|---|---|---|---|---|---|---|---|---|
| | B | B | B | B | | | | | | | | |
| | B | B | B | B | | | | | | | | |
| | B | B | A | B | | | | | | | | |
| | A | A | B | A | | | | | | | | |
| | A | B | B | A | | | | | | | | |
| | A | B | B | B | | | | | | | | |
| | B | B | B | A | | | | | | | | |
| | B | B | B | B | | | | | | | | |
| | B | B | A | B | | | | | | | | |
| | B | B | B | B | | | | | | | | |
| | B | A | B | B | | | | | | | | |
| | B | B | B | B | | | | | | | | |
| | B | B | B | B | CC | CC | BB | | | | | |
| | B | B | B | B | BB | CC | BB | BB | | | | |
| | B | B | B | B | | | | | | | | |

FIG. 1J
| Structure | | | | | | | | | | | |
|---|---|---|---|---|---|---|---|---|---|---|---|
|  | A | A | B | A | | | | | | | |
| 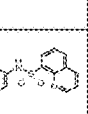 | A | B | B | B | | | | | | | |
| 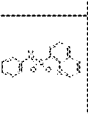 | B | A | B | A | | | | | | | |
| 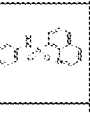 | A | B | B | B | | | | | | | |
|  | B | A | B | A | | | | | | | |
|  | B | B | B | B | | | | | | | |
|  | B | B | B | B | AA | AA | AA | | BB | | AA |
|  | B | B | B | B | | | | | | | |
|  | B | B | B | B | CC | CC | CC | CC | | | |
| 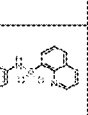 | B | B | B | B | BB | CC | BB | BB | | | |
| 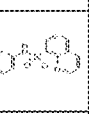 | B | B | B | B | AA | AA | AA | AA | | | |
|  | B | B | B | B | AA | AA | AA | AA | | | |
|  | B | B | B | B | AA | AA | AA | | | | |
|  | B | B | B | B | AA | CC | | | | | |
|  | B | B | B | B | | | | | | | |

FIG. 1K
| Structure | | | | | | | | | | | | |
|---|---|---|---|---|---|---|---|---|---|---|---|---|
|  | B | B | B | B | | | | | | | | |
|  | A | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | A | B | B | B | | | | | | | | |
|  | B | B | B | B | | | | | | | | |
|  | B | B | B | A | | | | | | | | |
|  | B | B | B | B | | | | | | | | |
|  | B | B | A | A | | | | | | | | |
|  | B | B | A | A | | | | | | | | |
|  | A | B | A | A | | | | | | | | |
|  | B | B | A | A | | | | | | | | |
|  | B | B | B | B | CC | CC | CC | CC | | | | |

FIG. 1L

| Structure | | | | | | | | | | | | |
|---|---|---|---|---|---|---|---|---|---|---|---|---|
| [structure] | B | B | B | B | | | | | | | | |
| [structure] | B | B | B | B | CC | CC | BB | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | CC | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |
| [structure] | B | B | B | B | | | | | | | | |

FIG. 1M
| Structure | | | | | | | | | | | | | |
|---|---|---|---|---|---|---|---|---|---|---|---|---|---|
|  | B | B | B | B | | | | | | | | | |
|  | A | B | B | B | | | | | | | | | |
|  | B | A | B | A | | | | | | | | | |
|  | B | B | B | B | | | | | | | | | |
|  | B | B | A | A | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | A | B | B | B | | | | | | | | | |
|  | B | B | B | B | | | | | | | | | |
|  | B | B | B | B | CC | | | | | | | | |
|  | B | B | B | B | | | | | | | | | |

FIG. 1N
| Structure | | | | | | | | | | | | |
|---|---|---|---|---|---|---|---|---|---|---|---|---|
| 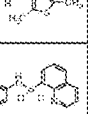 | B | B | B | B | | | | | | | | |
| 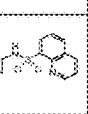 | B | B | B | B | | | | | | | | |
| | A | B | B | B | | | | | | | | |
| | B | B | B | B | BB | CC | CC | CC | | | | |
| | B | A | B | B | | | | | | | | |
| | B | B | B | B | AA | BB | AA | | | | | |
| | A | A | B | A | | | | | | | | |
| | B | B | B | B | AA | CC | AA | AA | | | | |
| | B | B | B | B | BB | CC | AA | BB | | | | |
| | B | B | B | B | | | | | | | | |
| | B | A | A | A | | | | | | | | |
| | B | B | B | B | AA | BB | AA | AA | | | | |
| | B | B | B | B | BB | CC | BB | BB | | | | |
| | B | B | B | B | CC | CC | BB | BB | | | | |
| | B | B | B | B | | | | | | | | |

FIG. 10

| Structure | | | | | | | | | | | | |
|---|---|---|---|---|---|---|---|---|---|---|---|
| (structure) | B | B | B | B | | CC | | | | | | |
| (structure) | B | B | B | B | CC | CC | BB | | | | | |
| (structure) | B | B | B | B | | | | | | | | |
| (structure) | B | B | B | B | | | | | | | | |
| (structure) | B | B | B | B | AA | AA | AA | | | | | |
| (structure) | B | B | B | B | AA | AA | | | | | | |
| (structure) | B | B | B | B | AA | AA | AA | AA | | | | |
| (structure) | B | B | C | B | AA | AA | | | | | | |
| (structure) | B | B | B | B | AA | CC | | | | | | |
| (structure) | B | B | B | B | AA | AA | | AA | | | | |
| (structure) | B | B | B | B | AA | BB | AA | AA | | | | |
| (structure) | B | B | B | B | | CC | AA | | | | | |
| (structure) | B | B | B | B | | | | | | | | |
| (structure) | B | B | A | B | AA | BB | AA | AA | | | | |
| (structure) | B | B | B | B | | | | | | | | |

FIG. 1P
| Structure | | | | | | | | | | | | |
|---|---|---|---|---|---|---|---|---|---|---|---|---|
|  | B | B | B | B | AA | CC | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | A | B | | | | | | | | |
|  | B | B | B | B | | | | | | | | |
|  | B | B | A | A | | | | | | | | |
|  | B | B | B | B | AA | CC | AA | AA | | | | |
|  | B | B | B | B | | | | | | | | |
|  | B | B | B | B | | | | | | | | |
|  | B | B | B | B | | | | | | | | |
| 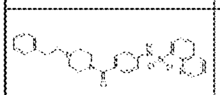 | A | A | B | B | | | | | | | | |
|  | B | B | B | B | | | | | | | | |

FIG. 1Q
| | | | | | | | | | | | | | |
|---|---|---|---|---|---|---|---|---|---|---|---|---|---|
|  | B | A | B | B | | | | | | | | | |
|  | B | A | A | B | | | | | | | | | |
|  | B | A | A | B | | | | | | | | | |
|  | B | B | B | B | | | | | | | | | |
|  | B | B | A | B | | | | | | | | | |
|  | A | A | A | B | | | | | | | | | |
|  | A | A | A | B | | | | | | | | | |
|  | B | A | B | B | | | | | | | | | |
|  | A | A | B | B | | | | | | | | | |
|  | A | A | A | B | | | | | | | | | |
|  | B | B | B | B | | | | | | | | | |
|  | B | B | A | B | | | | | | | | | |
|  | B | B | A | B | | | | | | | | | |
|  | B | B | B | B | | | | | | | | | |
|  | B | B | B | B | | | | | | | | | |

FIG. 1R
| Structure | | | | | | | | | | | | |
|---|---|---|---|---|---|---|---|---|---|---|---|---|
|  | B | B | B | B | | | | | | | | |
|  | B | B | B | B | | | | | | | | |
|  | B | A | B | B | BB | | | | | | | |
|  | B | B | B | B | | | | | | | | |
|  | B | B | B | B | | | | | | | | |
|  | B | A | B | B | | | | | | | | |
|  | B | A | A | B | | | | | | | | |
|  | B | A | B | B | | | | | | | | |
|  | B | B | B | B | | | | | | | | |
|  | B | A | B | B | | | | | | | | |
|  | B | B | B | B | | | | | | | | |
|  | B | B | B | B | | | | | | | | |
|  | B | B | B | B | | | | | | | | |
|  | B | A | B | B | | | | | | | | |
|  | B | A | B | B | | | | | | | | |

FIG. 1S

| Structure | | | | | | | | | | | | |
|---|---|---|---|---|---|---|---|---|---|---|---|---|
| (structure 1) | B | B | B | B | | | | | | | | |
| (structure 2) | B | A | B | B | | | | | | | | |
| (structure 3) | B | A | B | A | | | | | | | | |
| (structure 4) | B | B | B | B | | | | | | | | |
| (structure 5) | B | B | B | B | | | | | | | | |
| (structure 6) | B | B | B | B | | | | | | | | |
| (structure 7) | B | B | B | B | AA | BB | AA | AA | | | | |
| (structure 8) | B | B | B | B | | | | | | | | |
| (structure 9) | B | A | B | B | | | | | | | | |
| (structure 10) | B | A | B | B | | | | | | | | |
| (structure 11) | B | A | B | B | | | | | | | | |
| (structure 12) | B | A | B | B | | | | | | | | |
| (structure 13) | B | A | B | B | | | | | | | | |
| (structure 14) | B | A | B | B | | | | | | | | |
| (structure 15) | B | B | B | B | | | | | | | | |

FIG. 1T

| Structure | | | | |
|---|---|---|---|---|
| [structure] | B | B | B | B |
| [structure] | B | B | B | B |
| [structure] | B | B | A | B |
| [structure] | B | B | B | B |
| [structure] | B | B | A | B |
| [structure] | B | B | A | B |
| [structure] | B | B | B | B |
| [structure] | B | B | B | B |
| [structure] | A | A | B | B |
| [structure] | B | A | B | A |
| [structure] | A | B | B | B |
| [structure] | B | B | B | B |
| [structure] | B | A | B | B |
| [structure] | B | B | B | B |
| [structure] | B | B | B | B |

FIG. 1U

| Structure | | | | | | | | | | | | |
|---|---|---|---|---|---|---|---|---|---|---|---|---|
| | B | B | B | B | | | | | | | | |
| | B | B | B | B | | | | | | | | |
| | B | B | B | B | CC | | | | | | | |
| | B | B | B | B | | | | | | | | |
| | B | B | B | B | | | | | | | | |
| | A | A | A | A | | | | | | | | |
| | A | A | A | A | | | | | | | | |
| | B | B | B | B | | | | | | | | |
| | B | A | A | A | | | | | | | | |
| | B | A | A | A | | | | | | | | |
| | B | B | A | B | | | | | | | | |
| | B | A | A | A | | | | | | | | |
| | B | B | B | B | | | | | | | | |
| | B | A | A | A | | | | | | | | |
| | B | A | A | A | | | | | | | | |

FIG. 1V

| Structure | | | | |
|---|---|---|---|---|
| | B | A | A | A |
| | B | A | A | B |
| | A | A | B | A |
| | B | A | A | B |
| | B | B | B | A |
| | A | A | A | A |
| | B | B | A | A |
| | A | A | A | A |
| | A | A | A | A |
| | B | B | B | B |
| | A | A | A | A |
| | B | B | B | A |
| | B | A | B | B |
| | B | A | B | B |
| | B | A | B | B |

FIG. 1W

| Structure | | | | |
|---|---|---|---|---|
| (structure) | B | A | B | B |
| (structure) | B | A | A | B |
| (structure) | B | A | B | B |
| (structure) | B | B | A | B |
| (structure) | B | A | A | B |
| (structure) | A | A | A | B |
| (structure) | B | B | B | B |
| (structure) | B | B | B | B |
| (structure) | B | B | B | B |
| (structure) | B | A | A | A |
| (structure) | B | A | A | B |
| (structure) | B | A | B | B |
| (structure) | B | A | B | B |
| (structure) | B | A | B | B |
| (structure) | B | B | B | B |

FIG. 1X
| Structure | | | | | | | | | | | | |
|---|---|---|---|---|---|---|---|---|---|---|---|---|
|  | B | A | B | B | | | | | | | | |
|  | A | A | A | B | | | | | | | | |
|  | B | A | B | B | AA | BB | AA | AA | | | | |
|  | B | A | B | B | | | | | | | | |
|  | B | B | B | B | | | | | | | | |
|  | B | B | B | B | | | | | | | | |
|  | A | A | A | B | | | | | | | | |
|  | B | B | A | B | | | | | | | | |
|  | B | B | B | B | | | | | | | | |
|  | B | B | B | B | | | | | | | | |
|  | B | B | B | B | | | | | | | | |
|  | B | B | B | B | AA | AA | | | | | | |
|  | B | A | A | A | | | | | | | | |
|  | B | B | B | B | | | | | | | | |
|  | B | B | B | B | AA | BB | AA | | | | | |

FIG. 1Y
| | | | | | | | | | | | |
|---|---|---|---|---|---|---|---|---|---|---|---|
|  | B | B | A | B | | | | | | | |
|  | B | A | A | B | | | | | | | |
|  | B | A | A | A | | | | | | | |
|  | B | B | B | B | | | | | | | |
|  | B | B | A | B | | | | | | | |
|  | B | B | B | B | | | | | | | |
|  | B | B | B | B | | | | | | | |
|  | B | B | B | B | | | | | | | |
|  | B | B | B | B | | | | | | | |
|  | B | B | B | B | | | | | | | |
|  | B | B | B | B | | | | | | | |
|  | B | B | A | B | | | | | | | |
|  | B | B | B | B | AA | CC | AA | AA | | BB | | AA |
|  | B | B | B | B | | | | | | | |
|  | B | A | B | B | | | | | | | |

FIG. 1Z

| Structure | | | | | | | | | | | | | |
|---|---|---|---|---|---|---|---|---|---|---|---|---|---|
| | B | A | B | B | | | | | | | | | |
| | B | A | B | B | | | | | | | | | |
| | B | A | B | B | | | | | | | | | |
| | B | B | B | B | | | | | | | | | |
| | B | B | B | B | AA | BB | AA | AA | | | | | |
| | B | A | B | B | | | | | | | | | |
| | B | A | B | B | | | | | | | | | |
| | B | B | B | B | | | | | | | | | |
| | B | A | B | B | | | | | | | | | |
| | B | A | A | A | | | | | | | | | |
| | A | B | B | A | | | | | | | | | |
| | B | B | A | B | | | | | | | | | |
| | A | A | A | B | | | | | | | | | |
| | B | B | A | B | | | | | | | | | |
| | B | A | B | B | | | | | | | | | |

FIG. 1AA

| Structure | | | | | | | | | | | | | |
|---|---|---|---|---|---|---|---|---|---|---|---|---|---|
| | B | A | B | B | | | | | | | | | |
| | B | A | B | B | | | | | | | | | |
| | B | B | A | B | | | | | | | | | |
| | B | B | B | B | | | | | | | | | |
| | B | A | A | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |

FIG. 1BB
| | | | | | | | | | | | | |
|---|---|---|---|---|---|---|---|---|---|---|---|---|
| 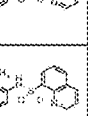 | B | B | B | B | | | | | | | | |
| 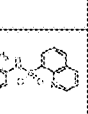 | B | B | B | B | | | | | | | | |
| 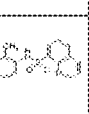 | B | B | B | B | | | | | | | | |
| 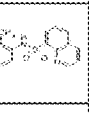 | B | B | B | B | | | | | | | | |
| 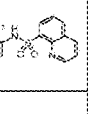 | B | B | B | B | | | | | | | | |
| 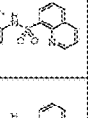 | B | B | B | B | | | | | | | | |
| 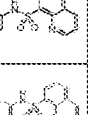 | B | A | B | B | AA | CC | AA | AA | | | | |
| 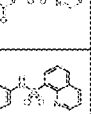 | B | A | A | B | BB | CC | BB | BB | | | | |
| 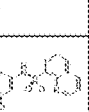 | B | B | B | B | CC | CC | CC | CC | | | | |
| 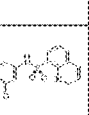 | B | B | A | B | | | | | | | | |
| 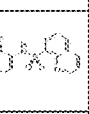 | B | A | A | B | | | | | | | | |
| 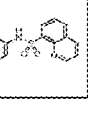 | A | A | A | B | | | | | | | | |
|  | B | A | B | B | | | | | | | | |
|  | B | A | B | B | | | | | | | | |
|  | B | B | B | B | | | | | | | | |

FIG. 10C
| | | | | | | | | | | | | |
|---|---|---|---|---|---|---|---|---|---|---|---|---|
|  | A | B | B | B | | | | | | | | |
|  | B | B | B | A | | | | | | | | |
|  | B | A | A | A | | | | | | | | |
|  | A | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | A | A | B | B | | | | | | | | |
|  | B | B | B | B | | | | | | | | |

FIG. 1DD
| Structure | | | | | | | | | | | | |
|---|---|---|---|---|---|---|---|---|---|---|---|---|
| 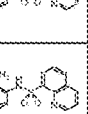 | A | A | B | B | | | | | | | | |
|  | B | B | B | B | | | | | | | | |
| 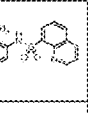 | B | B | B | B | | | | | | | | |
| 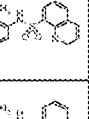 | B | B | B | B | | | | | | | | |
|  | B | B | B | B | | | | | | | | |
| 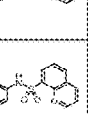 | B | A | B | B | | | | | | | | |
| 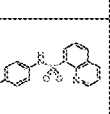 | B | B | B | B | | | | | | | | |
|  | B | B | B | B | | | | | | | | |
| 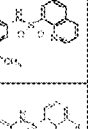 | B | B | B | B | | | | | | | | |
| 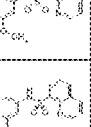 | B | B | B | B | | | | | | | | |
| 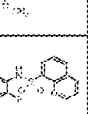 | B | B | B | B | | | | | | | | |
|  | B | B | B | B | AA | BB | | | CC | AA | | |
|  | B | B | B | B | | | | | | | | |
|  | B | B | B | B | BB | CC | BB | | | | | |
|  | B | B | B | B | | | | | | | | |

FIG. 1EE

| Structure | | | | |
|---|---|---|---|---|
| | B | B | B | B |
| | B | B | B | A |
| | B | B | A | B |
| | B | A | B | B |
| | A | A | A | A |
| | A | B | B | B |
| | A | A | B | B |
| | B | B | B | B |
| | B | B | B | B |
| | B | A | B | B |
| | B | B | B | B |
| | B | A | B | B |
| | B | A | A | A |
| | A | B | B | B |
| | B | A | B | B |

FIG. 1FF

| Structure | | | | | | | | | | | | | |
|---|---|---|---|---|---|---|---|---|---|---|---|---|---|
| | B | B | B | B | | | | | | | | | |
| | B | B | A | B | | | | | | | | | |
| | B | B | B | B | | | | | | | | | |
| | B | B | B | B | | | | | | | | | |
| | B | B | B | B | | | | | | | | | |
| | B | A | A | B | | | | | | | | | |
| | A | A | B | B | | | | | | | | | |
| | B | A | B | B | | | | | | | | | |
| | B | A | B | B | | | | | | | | | |
| | B | B | B | B | | | | | | | | | |
| | B | B | B | A | | | | | | | | | |
| | B | B | A | B | | | | | | | | | |
| | B | A | B | B | | | | | | | | | |
| | B | A | A | A | | | | | | | | | |
| | B | A | B | A | | | | | | | | | |

FIG. 1GG

| Structure | | | | | | | | | | | | |
|---|---|---|---|---|---|---|---|---|---|---|---|---|
| [structure] | B | A | A | B | | | | | | | | |
| [structure] | A | A | B | B | | | | | | | | |
| [structure] | B | A | B | A | | | | | | | | |
| [structure] | A | A | B | A | | | | | | | | |
| [structure] | B | B | A | B | | | | | | | | |
| [structure] | B | B | B | B | | | | | | | | |
| [structure] | A | A | B | B | | | | | | | | |
| [structure] | B | B | B | B | | | | | | | | |
| [structure] | A | A | A | A | | | | | | | | |
| [structure] | B | B | B | A | | | | | | | | |
| [structure] | A | A | B | B | | | | | | | | |
| [structure] | B | A | B | B | | | | | | | | |
| [structure] | B | B | B | B | | | | | | | | |
| [structure] | B | B | B | B | | | | | | | | |
| [structure] | B | A | B | B | | | | | | | | |

FIG. 1HH
| Structure | | | | | | | | | | | | | |
|---|---|---|---|---|---|---|---|---|---|---|---|---|---|
|  | B | A | A | B | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | B | A | A | A | | | | | | | | | |
|  | B | A | A | A | | | | | | | | | |
|  | B | A | B | B | | | | | | | | | |
|  | B | B | A | A | | | | | | | | | |
|  | B | B | B | B | | | | | | | | | |
|  | B | B | B | B | | | | | | | | | |
|  | B | B | B | B | | | | | | | | | |
|  | B | B | B | B | AA | BB | AA | AA | | BB | | AA | |
|  | A | A | B | B | | | | | | | | | |

FIG. 1II

| Structure | | | | | | | | | | | | |
|---|---|---|---|---|---|---|---|---|---|---|---|---|
| | A | B | B | B | | | | | | | | |
| | A | B | B | B | | | | | | | | |
| | B | B | B | B | | | | | | | | |
| | B | A | B | B | | | | | | | | |
| | A | B | A | B | | | | | | | | |
| | B | B | B | B | | | | | | | | |
| | A | A | A | B | | | | | | | | |
| | B | A | B | B | | | | | | | | |
| | A | A | B | B | | | | | | | | |
| | A | B | B | B | | | | | | | | |
| | B | A | B | B | | | | | | | | |
| | B | A | B | B | | | | | | | | |
| | B | B | B | B | AA | AA | AA | AA | | | | |
| | B | B | B | B | | | | | | | | |
| | B | B | B | B | | | | | | | | |

FIG. 1JJ
| Structure | | | | | | | | | | | | |
|---|---|---|---|---|---|---|---|---|---|---|---|---|
|  | B | B | B | B | | | | | | | | |
|  | B | B | B | B | | | | | | | | |
|  | B | B | B | B | AA | BB | AA | AA | | | | |
|  | B | B | B | B | | | | | | | | |
|  | B | B | B | B | | | | | | | | |
|  | B | B | B | B | | | | | | | | |
|  | A | B | B | B | | | | | | | | |
|  | B | B | B | B | | | | | | | | |
|  | B | B | B | B | | | | | | | | |
|  | B | B | B | B | | | | | | | | |
|  | A | A | B | A | | | | | | | | |
|  | B | A | B | B | | | | | | | | |
|  | A | B | B | B | | | | | | | | |
|  | B | B | B | B | | | | | | | | |
|  | A | A | B | B | | | | | | | | |

FIG. 1KK
| Structure | | | | | | | | | | | | |
|---|---|---|---|---|---|---|---|---|---|---|---|---|
|  | A | B | B | B | | | | | | | | |
|  | A | B | B | B | | | | | | | | |
|  | B | B | B | B | AA | BB | AA | | | | | |
|  | B | B | B | B | BB | CC | BB | | | | | |
|  | B | B | B | B | | | | | | | | |
|  | B | B | B | B | | | | | | | | |
|  | B | A | A | A | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | A | A | B | B | | | | | | | | |
|  | A | A | B | B | | | | | | | | |
|  | B | A | B | B | | | | | | | | |
|  | B | B | B | B | | | | | | | | |

FIG. 1LL.
| Structure | | | | | | | | | | | | |
|---|---|---|---|---|---|---|---|---|---|---|---|---|
| 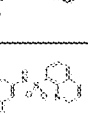 | A | A | B | B | | | | | | | | |
| 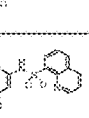 | A | A | B | B | | | | | | | | |
| 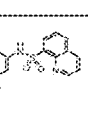 | A | A | B | B | | | | | | | | |
| 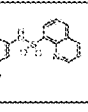 | B | A | B | B | | | | | | | | |
| 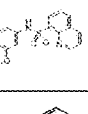 | B | B | B | B | | | | | | | | |
| 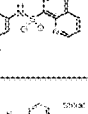 | B | B | B | B | | | | | | | | |
| 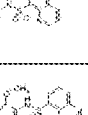 | B | B | B | B | | | | | | | | |
| 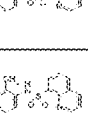 | B | B | B | B | | | | | | | | |
|  | B | B | B | B | | | | | | | | |
| 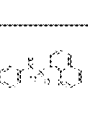 | B | B | B | B | | | | | | | | |
|  | B | B | B | B | | | | | | | | |
|  | B | B | B | B | CC | | CC | CC | | | | |
|  | B | B | B | B | | | | | | | | |
|  | B | B | B | B | AA | BB | AA | | | | | |
|  | B | B | B | B | | | | | | | | |

FIG. 1MM

| Structure | | | | | | | | | | | | |
|---|---|---|---|---|---|---|---|---|---|---|---|---|
| (structure) | B | B | B | B | | | | | | | | |
| (structure) | B | B | B | B | | | | | | | | |
| (structure) | B | B | B | B | | | | | | | | |
| (structure) | B | B | B | B | AA | | | BB | | | | |
| (structure) | B | B | B | B | | | | | | | | |
| (structure) | B | B | B | B | | | | | | | | |
| (structure) | B | B | B | B | | | | | | | | |
| (structure) | B | B | B | B | AA | AA | AA | AA | | | | |
| (structure) | B | B | B | B | AA | CC | AA | BB | BB | BB | CC | AA |
| (structure) | B | B | B | B | | | | | | | | |
| (structure) | B | B | A | A | | | | | | | | |
| (structure) | B | B | B | B | | | | | | | | |
| (structure) | A | A | B | A | | | | | | | | |
| (structure) | A | A | A | B | | | | | | | | |
| (structure) | B | A | B | A | | | | | | | | |

FIG. 1NN

| Structure | | | | |
|---|---|---|---|---|
| (structure) | A | A | B | A |
| (structure) | A | A | A | B |
| (structure) | A | B | A | B |
| (structure) | A | B | A | B |
| (structure) | A | A | A | B |
| (structure) | A | A | B | A |
| (structure) | B | A | B | B |
| (structure) | A | A | A | A |
| (structure) | B | B | B | B |
| (structure) | B | B | B | B |
| (structure) | B | B | B | B |
| (structure) | B | B | B | B |
| (structure) | B | B | B | B |
| (structure) | B | B | B | B |
| (structure) | B | B | B | B |

FIG. 10O
| Structure | | | | | | | | | | | | | |
|---|---|---|---|---|---|---|---|---|---|---|---|---|---|
|  | B | B | B | B | | | | | | | | | |
|  | B | B | B | B | | | | | | | | | |
|  | B | B | B | B | | | | | | | | | |
|  | B | B | A | B | | | | | | | | | |
|  | B | B | A | B | | | | | | | | | |
|  | A | B | A | B | | | | | | | | | |
|  | A | B | B | B | | | | | | | | | |
|  | B | B | B | B | | | | | | | | | |
|  | B | B | B | B | | | | | | | | | |
|  | B | B | B | B | | | | | | | | | |
|  | A | B | A | B | | | | | | | | | |
|  | A | B | A | B | | | | | | | | | |
|  | A | A | A | A | | | | | | | | | |
|  | B | B | B | B | | | | | | | | | |
|  | B | A | B | A | | | | | | | | | |

FIG. 1PP

| Structure | | | | | | | | | | | | |
|---|---|---|---|---|---|---|---|---|---|---|---|---|
| | B | B | A | B | | | | | | | | |
| | B | B | A | B | | | | | | | | |
| 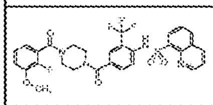 | A | B | A | A | | | | | | | | |
| | B | B | A | B | | | | | | | | |
| | B | B | B | B | | | | | | | | |
| | B | B | B | B | | | | | | | | |
| | B | B | B | B | | | | | | | | |
| | B | B | B | B | | | | | | | | |
| | B | B | B | B | | | | | | | | |
| | B | B | B | B | | | | | | | | |
| | B | B | A | B | | | | | | | | |
| | B | B | B | B | | | | | | | | |
| | B | B | B | B | | | | | | | | |
| | B | B | B | B | CC | CC | BB | CC | | | | |
| | B | A | B | B | | | | | | | | |

FIG. 1QQ

| Structure | | | | | | | | | | | | |
|---|---|---|---|---|---|---|---|---|---|---|---|---|
| | B | B | B | B | AA | AA | AA | AA | | | | |
| | B | B | B | A | | | | | | | | |
| | B | B | A | B | | | | | | | | |
| | B | B | A | B | | | | | | | | |
| 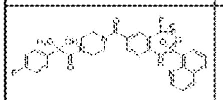 | A | B | B | B | | | | | | | | |
| | B | A | B | B | | | | | | | | |
| | B | A | B | B | | | | | | | | |
| | B | B | B | B | | | | | | | | |
| | B | B | B | B | | | | | | | | |
| | B | B | A | A | | | | | | | | |
| | B | B | B | B | | | | | | | | |
| | B | A | B | B | | | | | | | | |
| | B | B | B | B | | | | | | | | |
| | B | B | B | B | | | | | | | | |
| | B | B | B | B | CC | | CC | | | | | |

FIG. 1RR
| Structure | | | | | | | | | | | | | |
|---|---|---|---|---|---|---|---|---|---|---|---|---|---|
| 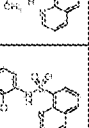 | B | B | B | B | | | | | | | | | |
| 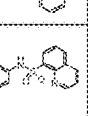 | B | B | B | B | | | | | | | | | |
| 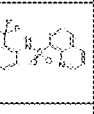 | B | B | B | B | | | | | | | | | |
|  | B | B | B | B | BB | CC | BB | BB | | | | | |
|  | B | B | B | B | | | | | | | | | |
| 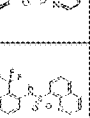 | B | B | B | B | | | | | | | | | |
| 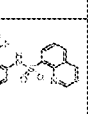 | B | B | B | B | | | | | | | | | |
| 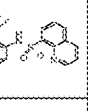 | B | B | B | B | | | | | | | | | |
| 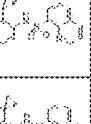 | B | B | B | B | | | | | | | | | |
|  | B | B | B | B | | | | | | | | | |
| 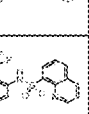 | B | A | A | A | | | | | | | | | |
|  | A | A | B | A | | | | | | | | | |
|  | A | A | B | B | | | | | | | | | |
|  | B | B | B | B | | | | | | | | | |
|  | B | B | B | B | | | | | | | | | |

FIG. 18S
| Structure | | | | | | | | | | | | | |
|---|---|---|---|---|---|---|---|---|---|---|---|---|---|
|  | A | A | B | B | | | | | | | | | |
|  | B | B | B | B | | | | | | | | | |
|  | B | B | B | B | | | | | | | | | |
|  | B | B | B | B | | | | | | | | | |
|  | B | B | B | B | | | | | | | | | |
|  | A | B | B | B | | | | | | | | | |
|  | A | A | B | B | | | | | | | | | |
|  | B | B | B | B | | | | | | | | | |
|  | A | A | B | B | | | | | | | | | |
|  | B | B | B | A | | | | | | | | | |
|  | B | B | B | B | | | | | | | | | |
|  | B | B | B | B | | | | | | | | | |
|  | A | B | B | A | | | | | | | | | |
|  | A | B | B | B | | | | | | | | | |
|  | B | A | B | B | | | | | | | | | |

FIG. 1TT

| Structure | | | | | | | | | | | | | |
|---|---|---|---|---|---|---|---|---|---|---|---|---|---|
| | B | B | B | B | | | | | | | | | |
| | B | A | B | B | | | | | | | | | |
| | B | A | B | A | | | | | | | | | |
| | B | B | B | B | | | | | | | | | |
| | B | A | B | A | | | | | | | | | |
| | B | A | B | B | | | | | | | | | |
| | B | A | B | B | | | | | | | | | |
| | B | B | B | B | | | | | | | | | |
| | B | B | B | B | | | | | | | | | |
| | B | B | B | B | | | | | | | | | |
| | B | B | B | B | | | | | | | | | |
| | B | B | A | A | | | | | | | | | |
| | B | B | B | B | | | | | | | | | |
| | B | B | B | B | | | | | | | | | |
| | B | B | B | B | | | | | | | | | |

FIG. 1UU
| Structure | | | | | | | | | | | | |
|---|---|---|---|---|---|---|---|---|---|---|---|---|
| 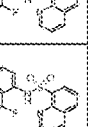 | B | B | B | B | | | | | | | | |
| 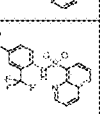 | B | B | B | B | | | | | | | | |
| | B | B | B | B | | | | | | | | |
| | B | B | B | B | | | | | | | | |
| | B | B | B | B | | | | | | | | |
| | B | B | B | B | | | | | | | | |
| | A | B | A | B | | | | | | | | |
| | A | A | A | A | | | | | | | | |
| | B | A | A | B | | | | | | | | |
| | B | B | B | B | | | | | | | | |
| | B | A | B | B | | | | | | | | |
| | B | A | A | B | | | | | | | | |
| | B | A | A | A | | | | | | | | |
| | A | B | B | B | | | | | | | | |
| | B | B | B | B | | | | | | | | |

FIG. 1VV
| Structure | | | | | | | | | | | | |
|---|---|---|---|---|---|---|---|---|---|---|---|---|
| 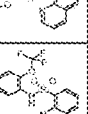 | A | A | B | A | | | | | | | | |
| 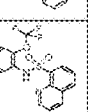 | B | B | B | B | | | | | | | | |
| 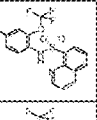 | A | B | A | A | | | | | | | | |
| 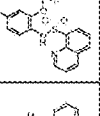 | B | B | B | B | | | | | | | | |
|  | B | B | B | B | | | | | | | | |
| 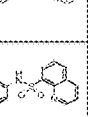 | B | A | B | B | | | | | | | | |
| 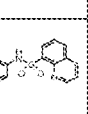 | B | B | B | B | | | | | | | | |
|  | B | B | B | B | AA | AA | | | | | | |
| 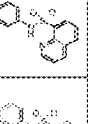 | B | B | B | B | | | | | | | | |
| 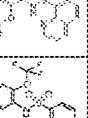 | B | B | B | B | | | | | | | | |
| 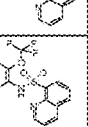 | B | A | A | B | | | | | | | | |

FIG. 1WW
| Structure | | | | | | | | | | | | | |
|---|---|---|---|---|---|---|---|---|---|---|---|---|---|
|  | A | B | A | A | | | | | | | | | |
|  | B | A | B | A | | | | | | | | | |
|  | B | A | A | A | | | | | | | | | |
|  | B | B | B | A | | | | | | | | | |
|  | B | B | B | A | | | | | | | | | |
|  | A | A | A | A | | | | | | | | | |
|  | B | B | B | B | | | | | | | | | |
|  | A | B | B | B | | | | | | | | | |
|  | B | B | A | B | | | | | | | | | |
|  | B | A | B | B | | | | | | | | | |
|  | A | A | A | A | | | | | | | | | |
|  | B | B | B | B | AA | CC | AA | | | | | | |
|  | B | B | B | B | | | | | | | | | |
|  | B | B | B | B | | | | | | | | | |
|  | B | B | B | B | | | | | | | | | |

FIG. 1XX
| Structure | | | | | | | | | | | | |
|---|---|---|---|---|---|---|---|---|---|---|---|---|
|  | B | B | B | B | | | | | | | | |
|  | B | B | B | B | | | | | | | | |
|  | B | B | B | B | | | | | | | | |
|  | B | B | B | B | | | | | | | | |
|  | B | B | B | B | CC | | | | | | | |
|  | A | B | A | A | | | | | | | | |
|  | A | B | B | A | | | | | | | | |
|  | A | B | B | B | | | | | | | | |
|  | B | B | B | B | | | | | | | | |
|  | B | B | B | B | | | | | | | | |
|  | B | B | B | B | | | | | | | | |
|  | B | B | A | A | | | | | | | | |
|  | B | A | A | A | | | | | | | | |
|  | B | B | B | B | | | | | | | | |
|  | B | B | A | B | | | | | | | | |

FIG. 1YY
| Structure | | | | | | | | | | | | |
|---|---|---|---|---|---|---|---|---|---|---|---|---|
|  | B | B | A | B | | | | | | | | |
|  | B | B | A | B | | | | | | | | |
|  | B | B | A | B | | | | | | | | |
|  | B | B | B | B | | | | | | | | |
|  | A | A | B | A | | | | | | | | |
|  | A | A | A | B | | | | | | | | |
|  | B | A | A | B | | | | | | | | |
|  | B | B | B | B | | | | | | | | |
|  | B | B | B | B | | | | | | | | |
|  | B | A | A | B | | | | | | | | |
|  | B | A | B | B | | | | | | | | |
|  | A | A | B | B | | | | | | | | |
|  | B | A | A | B | | | | | | | | |
|  | B | B | B | B | | | | | | | | |
|  | A | A | A | B | | | | | | | | |

FIG. 1ZZ
| Structure | | | | | | | | | | | | |
|---|---|---|---|---|---|---|---|---|---|---|---|---|
|  | B | B | B | B | | | | | | | | |
|  | B | B | B | A | | | | | | | | |
|  | B | A | B | B | | | | | | | | |
|  | B | B | B | B | | | | | | | | |
| 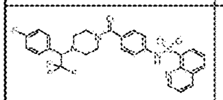 | A | B | A | B | | | | | | | | |
|  | B | B | A | B | | | | | | | | |
|  | B | B | A | A | | | | | | | | |
|  | B | A | B | B | | | | | | | | |
|  | B | B | B | B | | | | | | | | |
|  | B | B | B | B | | | | | | | | |
|  | B | B | B | B | | | | | | | | |
|  | B | B | B | B | | | | | | | | |
|  | B | A | A | B | | | | | | | | |
|  | B | B | B | B | | | | | | | | |
|  | B | B | B | B | | | | | | | | |

FIG. 1AAA
| Structure | | | | | | | | | | | | | |
|---|---|---|---|---|---|---|---|---|---|---|---|---|---|
|  | B | B | B | B | | | | | | | | | |
|  | B | B | B | B | | | | | | | | | |
|  | B | B | B | B | | | | | | | | | |
|  | B | B | B | B | BB | CC | | | | | | | |
|  | B | B | B | B | | | | | | | | | |
|  | B | B | B | B | | | | | | | | | |
|  | A | A | A | A | | | | | | | | | |
|  | A | A | B | B | | | | | | | | | |
|  | A | A | B | B | | | | | | | | | |
|  | B | B | B | B | | | | | | | | | |
|  | B | B | B | B | | | | | | | | | |
|  | B | A | A | B | | | | | | | | | |
|  | B | B | B | B | | | | | | | | | |
|  | B | B | B | B | | | | | | | | | |
|  | B | B | B | B | | | | | | | | | |

FIG. 1BBB
| Structure | | | | | | | | | | |
|---|---|---|---|---|---|---|---|---|---|---|
|  | B | B | B | B | | | | | | |
|  | B | B | B | B | | | | | | |
|  | A | A | A | A | | | | | | |
|  | B | B | B | B | | | | | | |
|  | B | A | B | B | | | | | | |
|  | B | B | A | A | | | | | | |
|  | B | B | A | A | | | | | | |
|  | B | B | A | B | AA | CC | AA | BB | | |
|  | B | B | B | B | AA | AA | AA | AA | AA | AA |
|  | B | B | B | B | | | | | | |
|  | B | B | B | B | | | | | | |
|  | B | B | B | B | AA | AA | AA | AA | | |
|  | B | B | B | B | | | | | | |
|  | B | B | B | B | | | | | | |
|  | B | B | B | B | | | | | | |

FIG. 10CC
| Structure | | | | | | | | | | | | | |
|---|---|---|---|---|---|---|---|---|---|---|---|---|---|
|  | B | B | B | B | | | | | | | | | |
|  | A | B | B | B | | | | | | | | | |
|  | B | B | B | B | | | | | | | | | |
|  | A | B | A | A | | | | | | | | | |
|  | B | A | A | A | | | | | | | | | |
|  | B | B | B | B | | | | | | | | | |
|  | A | A | A | A | | | | | | | | | |
|  | A | A | A | A | | | | | | | | | |
|  | A | A | A | A | | | | | | | | | |
|  | A | A | A | B | | | | | | | | | |
|  | A | A | A | A | | | | | | | | | |
|  | A | A | A | A | | | | | | | | | |
|  | A | A | A | A | | | | | | | | | |
|  | A | A | A | A | | | | | | | | | |
|  | B | B | B | B | | | | | | | | | |

FIG. 1DDD
| Structure | | | | | | | | | | | | |
|---|---|---|---|---|---|---|---|---|---|---|---|---|
|  | A | B | B | B | | AA | | | | | | |
|  | B | B | B | A | | | | | | | | |
|  | B | B | B | B | | | | | | | | |
|  | A | A | B | B | | | | | | | | |
|  | A | A | A | A | | | | | | | | |
|  | B | A | A | B | CC | CC | CC | | | | | |
|  | A | A | A | A | | | | | | | | |
|  | B | A | A | A | | | | | | | | |
|  | B | A | A | A | CC | CC | BB | | | | | |
|  | B | B | B | B | | | | | | | | |
|  | A | B | A | A | CC | CC | CC | | | | | |
|  | B | A | A | A | | | | | | | | |
|  | B | B | A | B | | | | | | | | |
|  | B | B | B | B | | | | | | | | |
|  | B | A | A | A | AA | AA | AA | AA | | | | |

FIG. 1EEEE
| Structure | | | | | | | | | | | | |
|---|---|---|---|---|---|---|---|---|---|---|---|---|
|  | A | A | B | B | | | | | | | | |
|  | B | A | B | B | | | | | | | | |
|  | A | A | B | A | | | | | | | | |
|  | B | A | B | B | | | | | | | | |
|  | A | A | B | B | | | | | | | | |
|  | B | A | B | B | BB | CC | BB | BB | BB | BB | CC | BB |
|  | B | A | B | B | | | | | | | | |
|  | B | A | B | B | | | | | | | | |
|  | A | A | B | B | | | | | | | | |
|  | B | B | B | B | BB | CC | BB | | | | | |
|  | A | B | B | A | | | | | | | | |
|  | B | A | B | B | | | | | | | | |
|  | B | B | B | A | | | | | | | | |
|  | B | B | B | B | | | | | | | | |
|  | B | B | B | B | | | | | | | | |

FIG. 1FFF
| Structure | | | | | | | | | | | | |
|---|---|---|---|---|---|---|---|---|---|---|---|---|
| 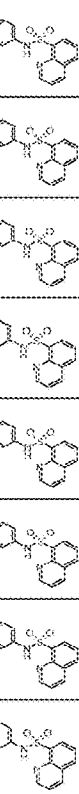 | B | B | B | B | | | | | | | | |
| 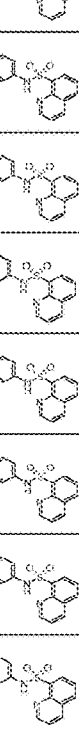 | B | B | B | B | BB | CC | BB | BB | | | | |
| 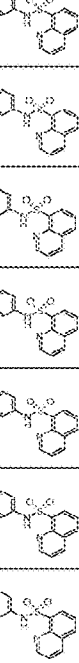 | A | B | B | B | AA | BB | AA | BB | AA | CC | | AA |
|  | B | B | B | B | | CC | BB | BB | BB | CC | CC | BB |
| 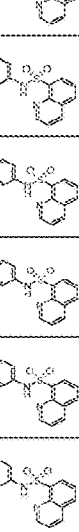 | A | A | B | B | AA | AA | AA | AA | | AA | | AA |
| 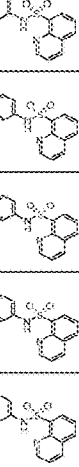 | A | A | A | A | | | | | | | | |
| 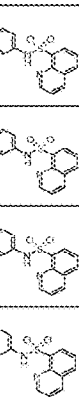 | A | A | A | A | | | | | | | | |
| 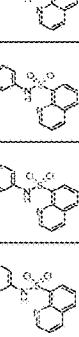 | A | A | A | A | | | | | | | | |
| 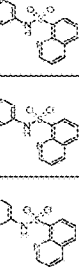 | A | A | A | A | AA | BB | AA | AA | | | | |
| 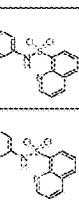 | A | A | B | B | | | | | | | | |

PYRUVATE KINASE ACTIVATORS FOR USE IN THERAPY

This application is a continuation of Ser. No. 17/221,423, filed on Apr. 2, 2021, which is a continuation of U.S. Ser. No. 16/821,101, filed Mar. 17, 2020, which is a continuation of U.S. Ser. No. 15/965,088, filed Apr. 27, 2018 and published as U.S. Pat. No. 10,632,114, which is a continuation of U.S. Ser. No. 15/583,412, filed May 1, 2017 and published as U.S. Pat. No. 9,980,961, which is a continuation of U.S. Ser. No. 14/886,750, filed Oct. 19, 2015 and published as U.S. Pat. No. 9,682,080, which is a continuation of U.S. Ser. No. 14/115,289, filed Feb. 11, 2014 and published as U.S. Pat. No. 9,193,701, which is a national stage application under 35 U.S.C. § 371 of International Application No. PCT/US2012/036412, filed May 3, 2012, and published as International Publication No. WO 2012/151451 on Nov. 8, 2012, which claims priority from U.S. Ser. No. 61/482,171, filed May 3, 2011, the contents of each of which is incorporated herein by reference in its entirety.

Pyruvate kinase deficiency (PKD) is one of the most common enzyme defects in erythrocytes in human due to autosomal recessive mutations of the PKLR gene (Zanella, A., et al., *Br J Haematol* 2005,130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature. Immature erythocytes have nuclei but during early erythropoiesis prior to becoming circulating reticulocytes they extrude nuclei as well as other organelles such as mitochondria, endoplasmic reticulum, and golgi apparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide (NAD$^+$) and to make ATP, an essential energy source largely used to drive ATPase-dependent K$^+$/Na$^+$ and Ca$^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate NAD$^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for Mg$^{2+}$ and K$^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation Thr$^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet* 2009, 75 (2), 157-62; Fermo, E. et al., *Br J Haematol* 2005,129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR.

The pattern of mutation prevalence seems to be unevenly distributed toward specific ethnic backgrounds. For instance, the most frequent codon substitutions reported for North American and European patients appear to be Arg$^{486}$>Trp and Arg$^{510}$>Gln, while mutations Arg$^{479}$>His, Arg[490]>Trp and Asp[331]>Gly were more frequently found in Asian patients (Kedar, P., et al., *Clin Genet* 2009, 75 (2), 157-62).

The present invention provides a method for increasing lifetime of the red blood cells (RBCs) in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention further provides a method for regulating 2,3-diphosphoglycerate levels in blood in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention also provides a method for treating hereditary non-spherocytic hemolytic anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating sickle cell anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976,39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2, 3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In one embodiment, provided is a pharmaceutical composition comprising a compound or a pharmaceutically acceptable salt of formula (I):

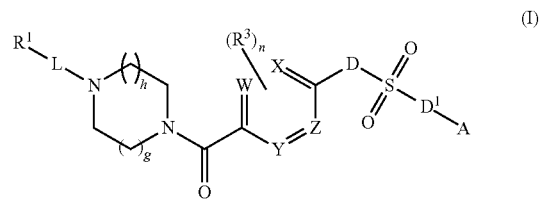

wherein:
W, X, Y and Z are each independently selected from CH or N;
D and $D^1$ are independently selected from a bond or $NR^b$;

A is optionally substituted aryl or optionally substituted heteroaryl;
L is a bond, —C(O)—, —(CR'R')$_m$—, —OC(O)—, —(CR'R')$_m$—OC(O)—, —(CR'R')$_m$—C(O)—, —NR$^b$C(S)—, or —NR$^b$C(O)— (wherein the point of the attachment to R$^1$ is on the left-hand side);
R$^1$ is selected from alkyl, cycloalkyl, aryl, heteroaryl, and heterocyclyl; each of which is substituted with 0-5 occurrences of R$^d$;
each R$^3$ is independently selected from halo, haloalkyl, alkyl, hydroxyl and —OR$^a$, or two adjacent R$^3$ taken together with the carbon atoms to which they are attached form an optionally substituted heterocyclyl; each R$^a$ is independently selected from alkyl, acyl, hydroxyalkyl and haloalkyl;
each R$^b$ is independently selected from hydrogen and alkyl;
each R$^c$ is independently selected from hydrogen, halo, alkyl, alkoxy and halo alkoxy or two R$^c$ taken together with the carbon atoms to which they are attached form an optionally substituted cycloalkyl;
each R$^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two R$^d$ taken together with the carbon atoms to which they are attached form an optionally substituted heterocyclyl;
n is 0, 1, or 2;
m is 1, 2 or 3;
h is 0, 1, 2; and
g is 0, 1 or 2.

BRIEF DESCRIPTION OF THE FIGURES

FIG. 1A-1FFF represents a table of exemplary compounds.

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that activate wild type PKR and/or various mutant PKRs such as those described herein.

In one embodiment, provided is a compound of formula (I) or a pharmaceutically acceptable salt thereof, or a pharmaceutical composition comprising a compound of formula (I) or a pharmaceutically acceptable salt thereof:

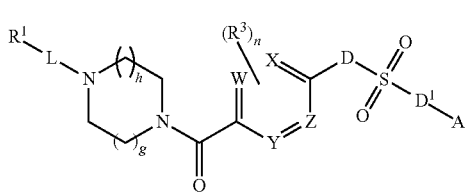

(I)

wherein:
W, X, Y and Z are each independently selected from CH or N;
D and D$^1$ are independently selected from a bond or NR$^b$;
A is optionally substituted bicyclic heteroaryl;
L is a bond, —C(O)—, —(CR'R')$_m$—, —OC(O)—, —(CR'R')$_m$—OC(O)—, —(CR'R')$_m$—C(O)—, —NR$^b$C(S)—, or —NR$^b$C(O)—;
R$^1$ is selected from alkyl, cycloalkyl, aryl, heteroaryl, and heterocyclyl; each of which is substituted with 0-5 occurrences of R$^d$;
each R$^3$ is independently selected from halo, haloalkyl, alkyl, hydroxyl and —OR$^a$ or two adjacent R$^3$ taken together with the carbon atoms to which they are attached form an optionally substituted cyclyl; each R$^a$ is independently selected from alkyl, acyl, hydroxyalkyl and haloalkyl;
each R$^b$ is independently selected from hydrogen and alkyl;

wherein:
W, X, Y and Z are each independently selected from CH or N;
D and D$^1$ are independently selected from a bond or NR$^b$;
A is optionally substituted aryl or optionally substituted heteroaryl;
L is a bond, —C(O)—, —(CR'R')$_m$—, —OC(O)—, —(CR'R')$_m$—OC(O)—, —(CR'R')$_m$—C(O)—, —NR$^b$C(S)—, or —NR$^b$C(O)— (wherein the point of the attachment to R$^1$ is on the left-hand side);
R$^1$ is selected from alkyl, cycloalkyl, aryl, heteroaryl, and heterocyclyl; each of which is substituted with 0-5 occurrences of R$^d$;
each R$^3$ is independently selected from halo, haloalkyl, alkyl, hydroxyl and —OR$^a$, or two adjacent R$^3$ taken together with the carbon atoms to which they are attached form an optionally substituted heterocyclyl;
each R$^a$ is independently selected from alkyl, acyl, hydroxyalkyl and haloalkyl;
each R$^b$ is independently selected from hydrogen and alkyl;
each R$^c$ is independently selected from hydrogen, halo, alkyl, alkoxy and halo alkoxy or two R$^c$ taken together with the carbon atoms to which they are attached form an optionally substituted cycloalkyl;
each R$^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two R$^d$ taken together with the carbon atoms to which they are attached form an optionally substituted heterocyclyl;
n is 0, 1, or 2;
m is 1, 2 or 3;
h is 0, 1, 2; and
g is 0, 1 or 2.
In certain embodiments, provided is a compound of formula (I) or a pharmaceutically acceptable salt thereof:

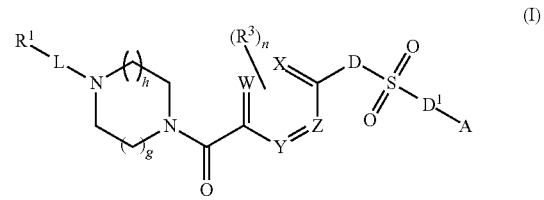

(I)

wherein:
W, X, Y and Z are each independently selected from CH or N;
D and D$^1$ are independently selected from a bond or NR$^b$;
A is optionally substituted bicyclic heteroaryl;
L is a bond, —C(O)—, —(CR'R')$_m$—, —OC(O)—, —(CR'R')$_m$—OC(O)—, —(CR'R')$_m$—C(O)—, —NR$^b$C(S)—, or —NR$^b$C(O)—;
R$^1$ is selected from alkyl, cycloalkyl, aryl, heteroaryl, and heterocyclyl; each of which is substituted with 0-5 occurrences of R$^d$;
each R$^3$ is independently selected from halo, haloalkyl, alkyl, hydroxyl and —OR$^a$ or two adjacent R$^3$ taken together with the carbon atoms to which they are attached form an optionally substituted cyclyl; each R$^a$ is independently selected from alkyl, acyl, hydroxyalkyl and haloalkyl;
each R$^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^a R^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In some embodiments, h is 1. In some embodiments, h is 2.

In some embodiments, g is 1. In some embodiments, g is 2.

In some embodiments, both h and g are 1. In some embodiments, h is 1 and g is 2. In some embodiments, g is 1 and h is 2.

In some embodiments, W, X, Y and Z are CH. In some embodiments, at least one of W, X, Y and Z is N. In some embodiments, at least two of W, X, Y and Z are N. In some embodiments, at least three of W, X, Y and Z are N.

In some embodiments, W, X, Y, Z and the carbons to which they are attached form a pyridyl ring. In some embodiments, W, X, Y, Z and the carbon atoms to which they are attached form a pyrimidyl ring. In some embodiments, W, X, Y, Z and the carbon atoms to which they are attached form a pyridazinyl ring.

In some embodiments, W, X and Y are CH and Z is N.

In some embodiments, X, Y and Z are CH and W is N.

In some embodiments, D is $NR^b$ and $D^1$ is a bond. In some embodiments, D is a bond and $D^1$ is $NR^b$. In some embodiments, both D and $D^1$ are $NR^b$. In some embodiments, $R^b$ is alkyl (e.g., methyl or ethyl). In some embodiments, $R^b$ is hydrogen (H).

In some embodiments, A is a 9-10 membered bicyclic heteroaryl (e.g., quinazolinyl, quinoxalinyl, cinnolinyl, isoquinolyl, indolyl, benzoxazolyl, pyrrolopyridyl, pyrrolopyrimidyl, benzimidazolyl, benzthiazolyl, or benzoxazolyl). In some embodiments, A is a N-containing 9-10 membered bicyclic heteroaryl. In some embodiments, A is optionally substituted quinazolinyl (e.g., 8-quinazolinyl or 4-quinazolinyl), optionally substituted quinoxalinyl (e.g., 5-quinoxalinyl), optionally substituted quinolinyl (e.g., 4-quinolinyl or 8-quinolinyl), optionally substituted cinnolinyl (e.g., 8-cinnolinyl), optionally substituted isoquinolinyl, optionally substituted indolyl (7-indolyl), optionally substituted benzoxazolyl (e.g., 7-benzoxazolyl), optionally substituted pyrrolopyridyl (e.g., 4-pyrrolopyridyl), optionally substituted pyrrolopyrimidyl (e.g., 4-pyrrolopyrimidyl), optionally substituted benzimidazolyl (e.g., 7-benzimidazolyl), optionally substituted benzthiazolyl (e.g., 4-benzthiazolyl, 2-methyl-4-benzthiazolyl or 7-benzthiazolyl), or optionally substituted benzoxazolyl (e.g., 4-benzoxazolyl).

In some embodiments, A is optionally substituted with halo. In some embodiments, A is

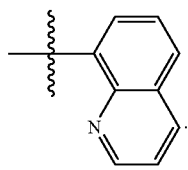

In some embodiments, A is

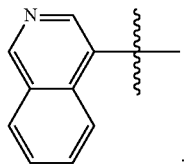 [SMILES: *c1cncc2ccccc12]

In some embodiments, A is optionally substituted

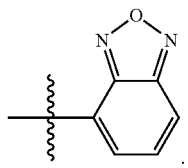

In some embodiments, A is

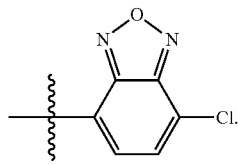 [SMILES: *c1ccc(Cl)c2nonc12]

In some embodiments, L is a bond.

In some embodiments, L is —(CR'R')$_m$— and m is 1. In some aspects of these embodiments, each $R^c$ is hydrogen. In some aspects of these embodiments, one $R^c$ is alkyl (e.g., methyl or ethyl) and the other $R^c$ is hydrogen. In some aspects of these embodiments, one $R^c$ is halo (e.g., fluoro) and one $R^c$ is hydrogen. In some aspects of these embodiments, both $R^c$ are halo (e.g., fluoro). In some aspects of these embodiments, one $R^c$ is alkoxy (e.g., methoxy or ethoxy) and one $R^c$ is hydrogen. In some aspects of these embodiments, both $R^c$ are alkoxy (e.g., methoxy or ethoxy). In some aspects of these embodiments, two $R^c$ taken together with the carbon to which they are attached form a cycloalkyl (e.g., cyclopropyl).

In some embodiments, L is —(CR'R')$_m$— and m is 2. In some aspects of these embodiments, each $R^c$ is hydrogen. In some aspects of these embodiments, 1 $R^c$ is alkyl (e.g., methyl or ethyl) and each of the other $R^c$ are hydrogen. In some aspects of these embodiments, two $R^c$s taken together with the carbon to which they are attached form a cycloalkyl (e.g., cyclopropyl) and each of the other two $R^c$s are hydrogen.

In some embodiments, L is —(CR'R')$_m$— and m is 3. In some aspects of these embodiments each $R^c$ is hydrogen.

In some embodiments, L is —C(O)—.

In some embodiments, L is —O—C(O)—.

In some embodiments, L is $NR^b$C(O)— and $R^b$ is H. In some embodiments, L is $NR^b$C(S)— and $R^b$ is H.

In some embodiments, L is —(CR'R')$_m$—C(O)— and m is 1. In some aspects of these embodiments, each $R^c$ is hydrogen. In some aspects of these embodiments, one $R^c$ is alkyl (e.g., methyl or ethyl) and one $R^c$ is hydrogen. In some aspects of these embodiments, both $R^c$ are alkyl (e.g., methyl or ethyl).

In some embodiments, L is —(CR'R')$_m$—C(O)— and m is 2. In some aspects of these embodiments, each $R^c$ is hydrogen.

In some embodiments, L is —(CR'R')$_m$—C(O)— and m is 3. In some aspects of these embodiments, each $R^c$ is hydrogen.

In some embodiments, $R^1$ is alkyl substituted with 0-5 occurrences of $R^d$ (e.g., methyl, ethyl, n-propyl, i-propyl, or n-butyl). In some embodiments, $R^1$ is methyl, ethyl, n-propyl, i-propyl, or n-butyl. In some embodiments, $R^1$ is ethyl or propyl (n-propyl or i-propyl). In some aspects of these embodiments, L is a bond, —CH$_2$—, —C(O)—, or —O(CO)—. In some aspects of these embodiments, L is —O(CO)—.

In some embodiments, $R^1$ is alkyl substituted with 1 occurrence of $R^d$ (e.g., methyl, ethyl, n-propyl, i-propyl, or n-butyl). In some embodiments, $R^1$ is methyl, ethyl, or n-propyl substituted with 1 occurrence of $R^d$. In some aspects of these embodiments, $R^d$ is halo (e.g., fluorine or chlorine). In some aspects of these embodiments, $R^d$ is —C(O)OR$^a$. In some aspects of these embodiments, $R^a$ is alkyl (e.g., methyl or ethyl). In some aspects of these embodiments, L is —NHC(O)—.

In some embodiments, $R^1$ is alkyl substituted with 2 occurrences of $R^d$ (e.g., methyl, ethyl, n-propyl, i-propyl, or n-butyl). In some embodiments, $R^1$ is methyl, ethyl, or n-propyl substituted with 2 occurrences of $R^d$. In some embodiments, $R^1$ is n-propyl substituted with 2 occurrences of $R^d$. In some aspects of these embodiments, 1 $R^d$ is cyano and the other $R^d$ is —NR$^a$R$^b$. In some aspects of these embodiments, $R^a$ and $R^b$ are hydrogen. In some aspects of these embodiments, L is —CH$_2$—.

In some embodiments, $R^1$ is heteroaryl substituted with 0-5 occurrences of $R^d$ (e.g., S-containing monocyclic heteroaryl, N-containing monocyclic heteroaryl or N-containing bicyclic heteroaryl). In some embodiments, $R^1$ is a 5-8 membered monocyclic heteroaryl substituted with 0-5 occurrences of $R^d$ (e.g., thiophenyl, pyridyl, pyrimidyl or pyrazyl). In some embodiments, $R^1$ is pyridyl substituted with 0-5 occurrences of $R^d$ (e.g., 2-pyridyl, 3-pyridyl or 4-pyridyl), pyrimidyl substituted with 0-5 occurrences of $R^d$ (e.g., 2-pyrimidyl or 5-pyrimidyl) or pyrazinyl substituted with 0-5 occurrences of $R^d$ (e.g., 2-pyrazinyl). In some embodiments, $R^1$ is thiazolyl substituted with 0-5 occurrences of $R^d$ (e.g., 2-thiazolyl or 5-thiazolyl). In some embodiments, $R^1$ is pyrimidyl substituted with 0-5 occurrences of $R^d$ (e.g., 2-pyrimidyl). In some embodiments, $R^1$ is thiadiazolyl substituted with 0-5 occurrences of $R^d$ (e.g., 4-thiadiazolyl). In some embodiments, $R^1$ is pyrrolyl substituted with 0-5 occurrences of $R^d$ (e.g., 2-pyrrolyl). In some aspects of these embodiments, L is a bond, —CH$_2$—, —C(O)—, or —O(CO)—. In some embodiments, $R^1$ is pyridyl (e.g., 2-pyridyl, 3-pyridyl or 4-pyridyl).

In some embodiments, $R^1$ is pyridyl (e.g., 2-pyridyl, 3-pyridyl or 4-pyridyl) substituted with 1 occurrence of $R^d$. In some aspects of these embodiments, $R^d$ is —OC(O)R$^a$. In some aspects of these embodiments, $R^d$ is —OR$^a$. In some aspects of these embodiments, $R^d$ is —C(O)OR$^a$. In some aspects of these embodiments, $R^d$ is alkyl (e.g., methyl or ethyl). In some aspects of these embodiments, $R^d$ is haloalkyl (e.g., trifluoromethyl). In some aspects of these embodiments, $R^d$ is halo (e.g., fluorine or chlorine). In some aspects of these embodiments, $R^a$ is alkyl (e.g., methyl or ethyl). In some aspects of these embodiments, L is —CH$_2$—. In some embodiments, $R^1$ is pyridyl (e.g., 2-pyridyl, 3-pyridyl or 4-pyridyl) substituted with 2 occurrences of $R^d$. In some aspects of these embodiments, one $R^d$ is —C(O)OR$^a$ and the other $R^d$ is —OR$^a$. In some aspects of these embodiments, $R^a$ is alkyl (e.g., methyl or ethyl). In some aspects of these embodiments, both $R^d$ are halo (e.g., fluoro or chloro). In some aspects of these embodiments, L is —CH$_2$—.

In some embodiments, $R^1$ is pyrimidyl (e.g., 2-pyrimidyl or 5-pyrimidyl). In some aspects of these embodiments, L is a bond.

In some embodiments, $R^1$ is pyrimidyl (e.g., 2-pyrimidyl or 5-pyrimidyl) substituted with 1 occurrence of $R^d$. In some aspects of these embodiments, $R^d$ is halo (e.g., fluoro or chloro).

In some embodiments, $R^1$ is pyrazinyl (e.g., 2-pyrazinyl). In some aspects of these embodiments, L is a bond.

In some embodiments, $R^1$ is thiazolyl (e.g., 2-thiazolyl, 4-thiazolyl, or 5-thiazolyl). In some aspects of these embodiments, L is —C(O)—.

In some embodiments, $R^1$ is thiazolyl (e.g., 2-thiazolyl, 4-thiazolyl, or 5-thiazolyl) substituted with 1 occurrences of $R^d$. In some aspects of these embodiments, $R^d$ is alkyl (e.g, methyl or ethyl). In some aspects of these embodiments, L is —C(O)—.

In some embodiments, $R^1$ is thiophenyl substituted with 0-5 occurrences of $R^d$ (e.g., 2-thiophenyl). In some embodiments, $R^1$ is thiophenyl.

In some embodiments, $R^1$ is thiadiazolyl (e.g., 4-thiadiazolyl).

In some embodiments, $R^1$ is pyrrolyl (e.g., 2-pyrrolyl).

In some embodiments, $R^1$ is cycloalkyl substituted with 0-5 occurrences of $R^d$ (e.g., cyclopropyl, cyclopentyl or cyclohexyl). In some embodiments, $R^1$ is cyclopropyl. In some embodiments, $R^1$ is cyclohexyl. In some embodiments, $R^1$ is cyclopentyl. In some aspect of these embodiments, L is —CH$_2$—C(O)—. In some embodiment, $R^1$ is aryl substituted with 0-5 occurrences of $R^d$. In some aspects of these embodiments, L is a bond, —CH$_2$—, —C(O)—, or —O(CO)—.

In some embodiments $R^1$ is aryl (e.g., phenyl). In some embodiments, $R^1$ is phenyl. In some aspects of these embodiments, L is a bond, —CH$_2$—, —C(O)—, or —O(CO)—.

In some embodiments, $R^1$ is phenyl substituted with 1 occurrence of $R^d$. In some aspects of these embodiments, $R^d$ is ortho substituted. In some aspects of these embodiments, $R^d$ is meta substituted. In some aspects of these embodiments, $R^d$ is para substituted. In some aspects of these embodiments, $R^d$ is halo (e.g., fluorine, bromine or chlorine). In some aspects of these embodiments, $R^d$ is alkyl (e.g., methyl, ethyl, isopropyl, t-butyl, n-butyl or n-pentyl). In some aspects of these embodiments, $R^d$ is haloalkyl (e.g., trifluoromethyl). In some aspects of these embodiments, $R^d$ is —OR$^a$. In some aspects of these embodiments, $R^d$ is —C(O)R$^a$. In some aspects of these embodiments, $R^d$ is —SR$^a$. In some aspects of these embodiments, $R^d$ is —C(O)OR$^a$. In some aspects of these embodiments, $R^d$ is cyano. In some aspects of these embodiments, $R^d$ is —NR$^a$R$^b$. In some aspects of these embodiments, $R^d$ is haloalkoxy (e.g., difluoromethoxy or trifluoromethoxy). In some aspects of these embodiments, $R^d$ is hydroxyl. In some aspects of these embodiments, $R^d$ is —OC(O)R$^a$. In some aspects of these embodiments, $R^d$ is alkynyl (e.g., 1-hexynyl). In some aspects of these embodiments, $R^d$ is haloalkyl (e.g., trifluoromethyl). In some aspects of these embodiments, $R^a$ is alkyl (e.g., methyl, ethyl, n-propyl, isopropyl, n-butyl, isobutyl, t-butyl or n-pentyl). In some aspects of these embodiments, $R^a$ is hydroxyalkyl (e.g., 2-hydroxyethyl). In some aspects of these embodiments, $R^a$ and $R^b$ are alkyl (e.g., methyl or ethyl). In some aspects of these embodiments, $R^a$ is acyl (e.g., acetyl) and $R^b$ is hydrogen. In some aspects of these embodiments, L is a bond, —$CH_2$—, —C(O)—, or —O(CO)—.

In some embodiments, $R^1$ is phenyl substituted with 2 occurrences of $R^d$. In some aspects of these embodiments, both $R^d$ are halo (e.g., fluorine or chlorine). In some aspects of these embodiments, both $R^d$ are alkyl (e.g., methyl or ethyl). In some aspects of these embodiments, 1 $R^d$ is alkyl (e.g., methyl or ethyl) and the other is —$OR^a$. In some aspects of these embodiments, 1 $R^d$ is halo (e.g., fluorine or chlorine) and the other $R^d$ is —$OR^a$. In some aspects of these embodiments, both $R^d$ are —$OR^a$. In some aspects of these embodiments, 1 $R^d$ is halo (e.g., fluorine or chlorine) and the other $R^d$ is hydroxyl. In some aspects of these embodiments, 1 $R^d$ is halo (e.g., fluorine or chlorine) and the other is haloalkyl (e.g., trifluoromethyl). In some aspects of these embodiments, 1 $R^d$ is —$OR^a$ and the other $R^d$ is —C(O)$OR^a$. In some aspects of these embodiments, 1 $R^d$ is —$OR^a$ and the other $R^d$ is hydroxyl. In some aspects of these embodiments, 1 $R^d$ is alkyl (e.g., methyl or ethyl) and the other $R^d$ is hydroxyl. In some aspects of these embodiments, both $R^d$ are hydroxyl. In some aspects of these embodiments, 1 $R^d$ is halo (e.g., fluorine) and the other $R^d$ is haloalkyl (e.g., trifluoromethyl). In some aspects of these embodiments, both $R^d$ are hydroxyl. In some aspects of these embodiments, one $R^d$ is haloalkyl (e.g., trifluoromethyl) and the other $R^d$ is alkyl (e.g., methyl). In some aspects of these embodiments, two $R^d$, together with the carbon atoms to which they are attached, form an optionally substituted heterocyclyl. In some aspects of these embodiments, two $R^d$, together with the carbon atoms to which they are attached, form an optionally substituted 5-7 membered heterocyclyl. In some aspects of these embodiments, two $R^d$, together with the phenyl ring to which they are attached, form the following structure:

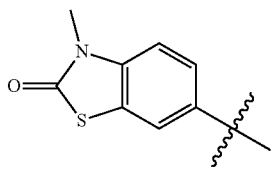

In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 3 occurrences of $R^d$. In some aspects of these embodiments, 3 $R^d$ are halo (e.g., fluorine or chlorine). In some aspects of these embodiments, 2 $R^d$ are halo (e.g., fluorine or chlorine) and 1 $R^d$ is hydroxyl. In some aspects of these embodiments, 1 $R^d$ is halo (e.g., fluorine or chlorine), 1 $R^d$ is alkyl (e.g., methyl) and 1 $R^d$ is hydroxyl. In some aspects of these embodiments, 3 $R^d$ are alkyl (e.g., methyl or ethyl). In some aspects of these embodiments, 2 $R^d$ are alkyl (e.g., methyl or ethyl) and 1 $R^d$ is hydroxyl. In some aspects of these embodiments, 2 $R^d$ are halo (e.g., fluorine or chlorine) and 1 $R^d$ is —$OR^a$. In some aspects of these embodiments, $R^a$ is alkyl (e.g., methyl or ethyl). In some aspects of these embodiments, 1 $R^d$ is hydroxyl and 2 $R^d$ are —$OR^a$. In some aspects of these embodiments, $R^a$ is alkyl (e.g., methyl or ethyl). In some aspects of these embodiments, 3 $R^d$ are —$OR^a$. In some aspects of these embodiments, 3 $R^d$ are halo (e.g., fluorine or chlorine). In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 4 occurrences of $R^d$. In some aspects of these embodiments, 1 $R^d$ is hydroxyl, 1 $R^d$ is alkyl (e.g., methyl or ethyl) and 2 $R^d$ are —$OR^a$. In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is heterocyclyl substituted with 0-5 occurrences of $R^d$.

In some embodiments, $R^1$ is tetrahydrofuranyl substituted with 0-5 occurrences of $R^d$ (e.g., 2-tetrahydrofuranyl or 3-tetrahydrofuranyl). In some aspects of these embodiments, $R^1$ is tetrahydrofuranyl (e.g., 2-tetrahydrofuranyl or 3-tetrahydrofuranyl). In some aspects of these embodiments, L is —C(O)—.

In some embodiments, $R^1$ is azetidinyl substituted with 0-5 occurrences of $R^d$ (e.g., 3-azetidinyl). In some embodiments, $R^1$ is azetidinyl (e.g., 3-azetidinyl). In some embodiments, $R^1$ is azetidinyl (e.g., 3-azetidinyl) substituted with 1 occurrence of $R^d$. In some aspects of these embodiments, $R^d$ is alkyl (e.g., methyl or ethyl). In some aspects of these embodiments, L is —C(O)—.

In some embodiments, $R^1$ is 10-14 membered bicyclic aryl substituted with 0-5 occurrences of $R^d$. In some embodiments, $R^d$ is naphthyl substituted with 0-5 occurrences of $R^d$.

In some embodiments, $R^d$ is naphthyl.

In some embodiments, L is a bond, —$(CR^cR^c)_m$—, —$NR^bC(O)$—, —$(CR^cR^c)_mC(O)$—, —C(O)—, or —O(CO)—.

In some embodiments, L is a bond and $R^1$ is alkyl, aryl or heteroaryl substituted with 0-5 occurrences of $R^d$. In some aspects of these embodiments, alkyl, aryl or heteroaryl of $R^1$ is as described in any one of the embodiments and aspects above.

In some embodiments, L is —(CR'R')$_m$— and $R^1$ is cycloalkyl, aryl, heteroaryl or heterocyclyl substituted with 0-5 occurrences of $R^d$. In some aspects of these embodiments, cycloalkyl, aryl, heteroaryl or heterocyclyl of $R^1$ is as described in any one of the embodiments and aspects above.

In some embodiments, L is —$NR^bC(O)$— and $R^b$ is hydrogen; and $R^1$ is aryl substituted with 0-5 occurrences of $R^d$. In some aspects of these embodiments, aryl of $R^1$ is as described in any one of the embodiments and aspects above.

In some embodiments, L is —(CR'R')$_m$—C(O)— and $R^1$ is cycloalkyl, aryl or heteroaryl substituted with 0-5 occurrences of $R^d$. In some aspects of these embodiments, cycloalkyl, aryl, or heteroaryl of $R^1$ is as described in any one of the embodiments and aspects above.

In some embodiments, L is —C(O)— and $R^1$ is aryl, alkyl, or heteroaryl substituted with 0-5 occurrences of $R^d$. In some aspects of these embodiments, aryl, alkyl, or heteroaryl of $R^1$ is as described in any one of the embodiments and aspects above.

In some embodiments, L is —OC(O)— and $R^1$ is alkyl, aryl or heterocyclyl substituted with 0-5 occurrences of $R^d$. In some aspects of these embodiments, alkyl, aryl, or heterocyclyl of $R^1$ is as described in any one of the embodiments and aspects above.

In some embodiments, L is —(CR'R')$_m$—OC(O)— and $R^1$ is heterocyclyl or cycloalkyl substituted with 0-5 occurrences of $R^d$. In some aspects of these embodiments, heterocyclyl or cycloalkyl of $R^1$ is as described in any one of the embodiments and aspects above.

In some embodiments, n is 0. In some embodiments, n is 1.

In some embodiments, $R^3$ is alkyl (e.g., methyl or ethyl). In some embodiments, $R^3$ is —$OR^a$. In some aspects of these embodiments, $R^a$ is alkyl (e.g., methyl or ethyl). In some embodiments, $R^3$ is halo (e.g., fluorine or chlorine). In some embodiments, $R^3$ is hydroxyl. In some embodiments, $R^3$ is haloalkyl (e.g., trifluoromethyl).

In some embodiments, n is 2.

In some embodiments, two adjacent $R^3$ taken together with the carbon atoms to which they are attached form a heterocyclyl ring. In some embodiments, both $R^3$ are —$OR^a$. In some embodiments, two adjacent $R^3$ taken together with the carbon atoms to which they are attached form

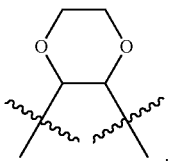 [SMILES: *C1OCCOC1*]

In certain embodiments, a compound is of formula (II) or a pharmaceutical acceptable salt thereof:

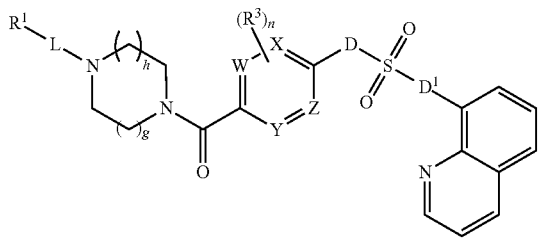

(II)

wherein L, $R^1$, $R^3$, $R^a$, $R^b$, $R^c$, $R^d$, Y, Z, m, h and g are as defined above in formula (I) or any one of the embodiments or aspects described herein.

In certain embodiments, A is aryl (e.g., phenyl or naphthyl) optionally substituted with 1 or 2 occurrences of $R^2$, wherein each $R^2$ is independently selected from halo, haloalkyl, aryl, heteroaryl, alkyl, —$OR^a$, —$COOR^c$, or —$CONR^cR^c$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspect of these embodiments, D and $D^1$ are N. In some aspect of these embodiments, at least one of W, X, Y and Z is N. In some aspect of these embodiments, one of W, Y and Z is N; h is 1 and g is 1.

In certain embodiments, A is heteroaryl (e.g., N-containing monocyclic heteroaryl or N-containing bicyclic heteroaryl); and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is a 5-8 membered monocyclic heteroaryl (e.g., pyridyl, pyrimidyl, or pyrazyl); and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is a 5-8 membered N-containing monocyclic heteroaryl; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is optionally substituted pyridyl (e.g., 2-pyridyl, 3-pyridyl or 4-pyridyl), optionally substituted pyrimidyl (e.g., 2-pyrimidyl or 5-pyrimidyl), or optionally substituted pyrazyl (e.g., 2-pyrazyl); and L, $R^1$, $R^3$, $R^a$, $R^b$, $R^c$, $R^d$, Y, Z, m, h and g are as defined above in formula (I) or any one of the embodiments or aspects described herein.

In some embodiments, A is substituted with 1 occurrence of $R^2$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspects of these embodiments, $R^2$ is alkyl (e.g., methyl or ethyl). In some aspects of these embodiments, $R^2$ is halo. In some aspects of these embodiments, $R^2$ is fluorine (F). In some aspects of these embodiments, $R^2$ is bromine (Br). In some aspects of these embodiments, $R^2$ is chlorine (Cl). In some aspects of these embodiments, $R^2$ is —$OR^a$. In some aspects of these embodiments, $R^a$ is alkyl (e.g., methyl).

In some embodiments, A is substituted with 2 occurrences of $R^2$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspects of these embodiments, both $R^2$ are halo (e.g., fluorine or fluorine and chlorine). In some aspects of these embodiments, both $R^2$ are alkyl (e.g., methyl). In some aspects of these embodiments, both $R^2$ are —$OR^a$. In some aspects of these embodiments, one $R^2$ is halo and the other is —$OR^a$. In some aspects of these embodiments, one $R^2$ is bromine (BR) and the other is —$OR^a$. In some aspects of these embodiments, one $R^2$ is chlorine (Cl) and the other is —$OR^a$. In some aspects of these embodiments, one $R^2$ is fluorine (F) and the other is —$OR^a$. In some aspects of these embodiments, $R^a$ is alkyl (e.g., methyl or ethyl). In some aspects of these embodiments, both $R^2$ are —$OR^a$. In some aspects of these embodiments, two —$OR^a$ taken together with the carbon atoms to which they are attached form a heterocyclyl. In some embodiments, A is

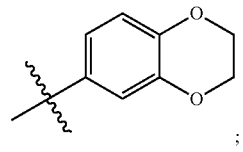

and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

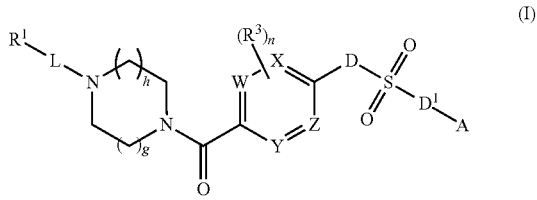

(I)

wherein:
W, X, Y and Z are each independently selected from CH or N;
D and $D^1$ are independently selected from a bond or $NR^b$;
A is optionally substituted aryl or optionally substituted heteroaryl;
L is a bond, —C(O)—, —(CR'R')$_m$—, —OC(O)—, or —C(O)$NR^b$—;
$R^1$ is independently selected from alkyl, cycloalkyl, aryl, heteroaryl, and heterocyclyl; each of which are substituted with 0-3 occurrences of $R^d$;
each $R^3$ is independently selected from halo, haloalkyl, alkyl, hydroxyl and —$OR^a$ or two adjacent $R^3$ taken together with the carbon atoms to which they are attached form an optionally substituted cyclyl;
each $R^a$ is independently selected from alkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted cycloalkyl;
each $R^d$ is independently selected from halo, haloalkyl, alkyl, nitro, cyano and —$OR^a$, or two $R^d$ taken together with the carbon atoms to which they are attached form an optionally substituted heterocyclyl;
n is 0, 1, or 2;
m is 1, 2 or 3;
h is 0, 1, 2; and
g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

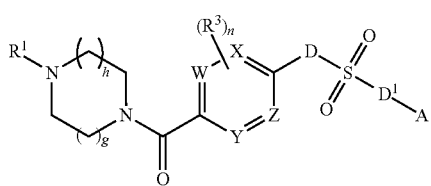

(I)

wherein:
W, X, Y and Z are each independently selected from CH or N;
D and $D^1$ are independently selected from a bond or $NR^c$;
A is optionally substituted aryl or optionally substituted heteroaryl;
$R^1$ is independently selected from alkyl, optionally substituted aryl, and optionally substituted heteroaryl;
each $R^3$ is independently selected from halo, haloalkyl, alkyl, and —$OR^a$;
each $R^a$ is independently selected from alkyl, haloalkyl and optionally substituted heteroaryl;
each $R^b$ is independently alkyl;
each $R^c$ is independently selected from hydrogen or alkyl;
n is 0, 1, or 2;
h is 0, 1, 2; and
g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound or pharmaceutically acceptable salt of formula (Ib) or a pharmaceutical composition comprising a compound or pharmaceutically acceptable salt of formula (Ib):

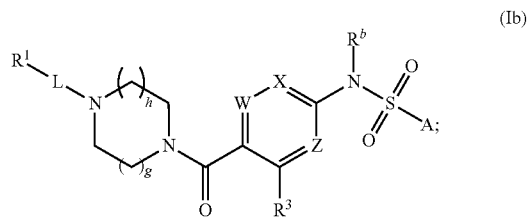

(Ib)

wherein A, L, $R^1$, $R^3$, $R^a$, $R^b$, $R^c$, $R^d$, W, X, Z, m, h and g are as defined above in formula (I) or any one of the embodiments or aspects described herein.

In some embodiments, X, W and Z are CH. In some embodiments, one of X, W and Z is N and the other two of X, W and Z are CH.

In another embodiment, provided is a pharmaceutical composition comprising a compound or pharmaceutically acceptable salt of formula (Ic) or a pharmaceutical composition comprising a compound or pharmaceutically acceptable salt of formula (Ic):

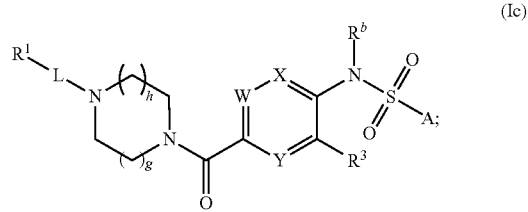

(Ic)

wherein A, L, $R^1$, $R^3$, $R^a$, $R^b$, $R^c$, $R^d$, W, X, Y, m, h and g are as defined above in formula (I) or any one of the embodiments or aspects described herein.

In some embodiments, X, Y and W are CH. In some embodiments, one of X, Y and W is N and the other two of X, Y and W are CH.

In another embodiment, provided is a compound or pharmaceutically acceptable salt of formula (Id) or a pharmaceutical composition comprising a compound or pharmaceutically acceptable salt of formula (Id):

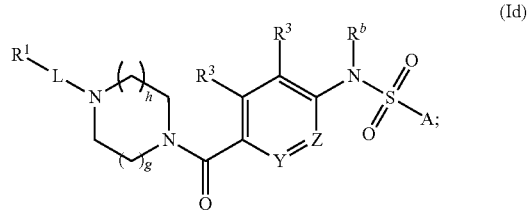

(Id)

wherein A, L, $R^1$, $R^3$, $R^a$, $R^b$, $R^c$, $R^d$, Y, Z, m, h and g are as defined above in formula (I) or any one of the embodiments or aspects described herein.

In some embodiments, Y and Z are CH. In some embodiments, one of Y and Z is N and one of Y and Z is CH.

In another embodiment, provided is a compound or pharmaceutically acceptable salt of formula (Ie) or a pharmaceutical composition comprising a compound or pharmaceutically acceptable salt of formula (Ie):

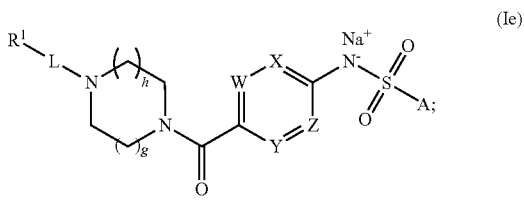

(Ie)

wherein A, L, $R^1$, $R^3$, $R^a$, $R^b$, $R^c$, $R^d$, W, X, Y, Z, m, h and g are as defined above in formula (I) or any one of the embodiments or aspects described herein.

In certain embodiments, exemplary compounds of Formula I include the compounds described in FIG. 1 and in the Examples.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2, 3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt) or mutated PKR (e.g., R510Q, R532W, OR T384W). Exemplary compounds are shown in FIG. 1. As shown in FIG. 1, A refers to a compound that has a % activation at 1 μM of from 1 to 100. B refers to an a compound that has a % activation at 1 μM of from 101 to 500. C refers a compound that has a % activation at 1 μM of >500.

In FIG. 1, a compound described herein may also have an AC50 of wild type PKR, PKR R532W, PKR T384W, PKR G332S, PKR G364D, PKR G37E and/or PKR R479H. AA refers to an AC50 less than 100 nM, BB refers to an AC50 from 101 nM to 500 nM and CC refers to an AC50 greater than 500 nM.

Other exemplary compounds can be found in International Patent Application No. PCT/US2010/040486 (e.g., in FIG. 1), published as WO 2011/002817 which is incorporated herein by reference in its entirety.

The compounds described herein can be made using a variety of synthetic techniques.

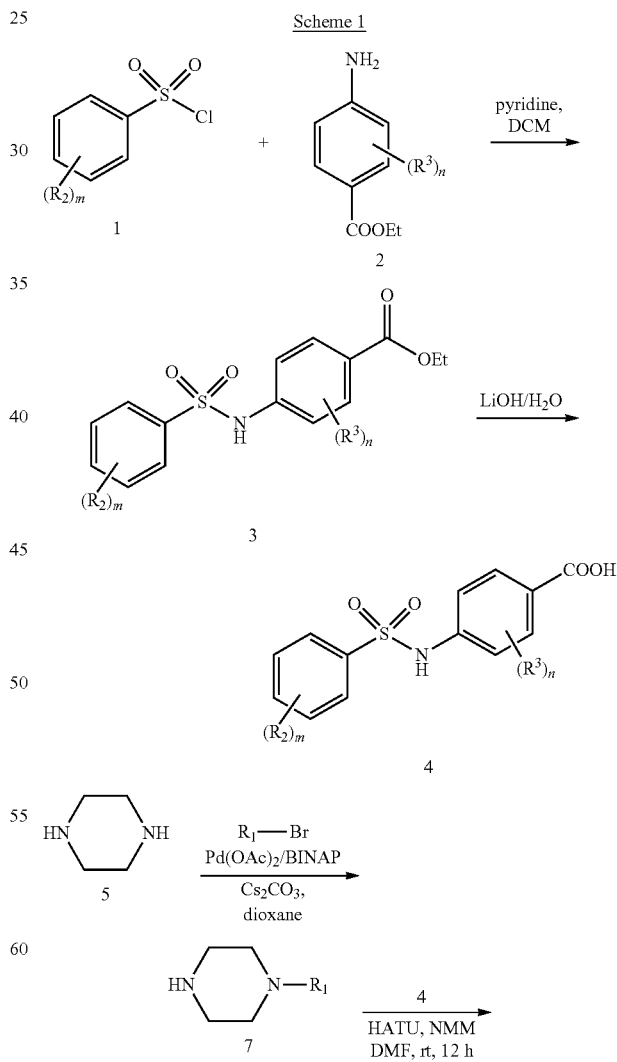

Scheme 1

-continued

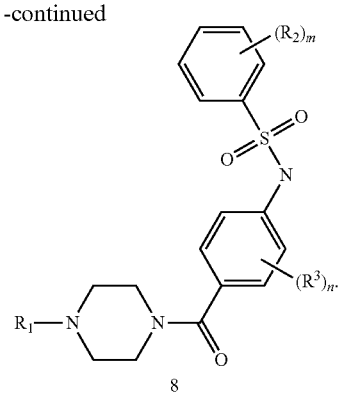

R¹, R², R³, m and n = as defined herin

Scheme 1 above is an exemplary scheme that depicts a representative synthesis of certain compounds described herein. Sulfonyl chloride 1 is reacted with amine 2 under standard coupling conditions to produce ester 3. Hydrolysis of 3 using lithium hydroxide generates carboxylic acid 4. Piperazine (5) is with the appropriate bromide under standard palladium coupling conditions to provide 7. Carboxylic acid 4 is then treated with piperazine derivative 7 to produce final compound 8.

The compounds described herein can be made using procedures disclosed in International Patent Application No. PCT/US2010/040486, published as WO 2011/002817 which is incorporated herein by reference in its entirety.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —CH₂—, —CH₂CH₂—, and —CH₂CH₂CH₂—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl- radical; the term dialkylaminoalkyl refers to a (alkyl)$_2$N-alkyl- radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to a monocyclic, bicyclic, or tricyclic aromatic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

The terms "heterocyclyl" or "heterocyclic group" refer to 3- to 14-membered non-aromatic ring structures (e.g., 3- to 14-membered rings, more preferably 3- to 7-membered rings), whose ring structures include one to four heteroatoms independently selected from O, N and S. The heterocyclyl or heterocyclic groups can contain fused or spiro rings. Heterocycles can also be polycycles, with each group having, e.g., 5-7 ring members. The term "heterocyclyl" or "heterocyclic group" includes saturated and partially saturated heterocyclyl structures. The term "heteroaryl" refers to a 5-14 membered (i.e., a 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from O, N, and S (e.g., 1-3, 1-6, or 1-9 ring heteroatoms of N, O, or S if monocyclic, bicyclic, or tricyclic, respectively). Any substitutable ring atom can be substituted (e.g., by one or more substituents). Heterocyclyl and heteroaryl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic or heteroaryl ring can be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "heterocyclylalkyl", as used herein, refers to an alkyl group substituted with a heterocycle group.

The term "cycloalkenyl" refers to partially unsaturated, nonaromatic, monocyclic, bicyclic, or tricyclic hydrocarbon groups having 5 to 12 carbons, preferably 5 to 8 carbons. The unsaturated carbon may optionally be the point of attachment of the cycloalkenyl substituent. Any substitutable ring atom can be substituted (e.g., by one or more substituents). The cycloalkenyl groups can contain fused or spiro rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, and S (e.g., 1-3, 1-6, or 1-9 ring heteroatoms of N, O, or S if monocyclic, bicyclic, or tricyclic, respectively). The unsaturated carbon or the heteroatom may optionally be the point of attachment of the heterocycloalkenyl substituent. Any substitutable ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The terms "hetaralkyl" and "heteroaralkyl", as used herein, refers to an alkyl group substituted with a heteroaryl group. The ring heteroatoms of the compounds provided herein include N—O, S(O), and S(O)$_2$.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any substitutable atom of that group. Any substitutable atom can be substituted. Unless otherwise specified, such substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as CF$_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as OCF$_3$), halo, hydroxy, carboxy, carboxylate, cyano, nitro, amino, alkyl amino, SO$_3$H, sulfate, phosphate, methylenedioxy (—O—CH$_2$—O— wherein oxygens are attached to vicinal atoms), ethylenedioxy, oxo (not a substituent on heteroaryl), thioxo (e.g., C=S) (not a substituent on heteroaryl), imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "activator" as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain activator compounds useful as PKR wild type and/or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (I-a), (II) or in FIG. 1).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

Example 1. PKR Mutant Assay

Procedure:
  PKR or PKR mutant enzyme solution was diluted in assay buffer.
  2 μL of test compound was added into wells first, and then 180 μL reaction mix was added.
  Reactions mixture with test compound was assembled except for ADP, and plates were stored for 60 minutes at room temperature.
  20 uL ADP was added to start reaction at room temperature and reaction progress was measured as changes in absorbance at 340 nm wavelength at room temperature.

Test Compound Preparation:
  Test compound stock was made at 100× concentration in 100% DMSO (10 mM)

1 to 3 dilutions were made for 11 points (i.e. 50 µl of first concentration added to 100 µl 100% DMSO to yield 3.33 mM, 50 µl of this added to 100 µl DMSO to yield 1.11 mM, and so forth)

1 to 100 dilution into assay (2 µl in 200 µl) yielded starting concentration of 100 µM, decreasing 3 fold for 11 points.

Assay Buffer: 100 mM KCl, 50 mM Tris 7.5, 5 mM MgCl2, 1 mM DTT, 0.03% BSA

Reaction Mixture: PKR mutant enzyme: 80-400 ng/well; ADP: 0.22-1.65 mM; PEP: 0.1-0.5 mM; NADH: 180 uM; LDH: 0.5 units (Sigma #59023); DTT: 1 mM; BSA: 0.03%.

Representative compounds disclosed herein were tested to be an activator of wild type PKR, PKRR532W, PKRR479H, and PKRG332S with an AC50 less than 500 nM against each wild type/mutant enzyme.

Example 2. PKR WT Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.

Final concentration: PKR wt (100 ng/well), Tris pH 7.5 (50 mM), KCl (100 mM), MgCl$_2$ (5 mM), ADP (0.48 mM), PEP (0.15 mM), NADH (180 µM), LDH (0.5 units, Sigma 59023), DTT (1 mM) and BSA (0.03%).

Example 3. PKR R510Q Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.

Final concentration: PKR R510Q (40 ng/well), Tris pH 7.5 (50 mM), KCl (100 mM), MgCl2 (5 mM), ADP (0.2 mM), PEP (0.11 mM), NADH (180 µM), LDH (0.5 units, Sigma 59023), DTT (1 mM) and BSA (0.03%).

Example 4. PKR R532W Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.

Final concentration: PKR R532W (100 ng/well), Tris pH 7.5 (50 mM), KCl (100 mM), MgCl2 (5 mM), ADP (0.36 mM), PEP (0.1 mM), NADH (180 µM), LDH (0.5 units, Sigma 59023), DTT (1 mM) and BSA (0.03%).

Example 5. PKR T384W Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL enzyme solution was added. Assays were assembled except for ADP, and plates were stored for 60 minutes at RT. 20 µL ADP was added to start the assay and assay output was evaluated using OD340 at SpectraMax. The assay was run at room temperature.

Final concentration: PKR T384W soluble (300 ng/well), Tris pH 7.5 (50 mM), KCl (100 mM), MgCl2 (5 mM), ADP (0.08 mM), PEP (0.23 mM), NADH (180 µM), LDH (0.5 units, Sigma 59023), DTT (1 mM) and BSA (0.03%).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of activating pyruvate kinase R in a subject in need thereof, comprising administering to the subject a therapeutically effective amount of a compound of formula (I) or a pharmaceutically acceptable salt thereof, wherein:

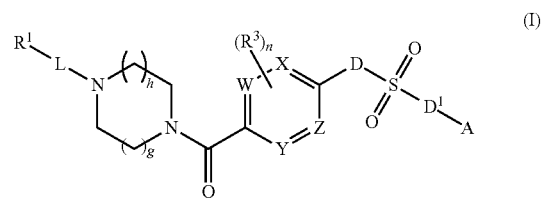

W, X, Y and Z are each independently selected from CH or N;

D and D$^1$ are each independently selected from a bond and NR$^b$;

A is optionally substituted aryl or optionally substituted heteroaryl;

L is a bond, —C(O)—, —(CR$^c$R$^c$)$_m$—, —OC(O)—, —(CR$^c$R$^c$)$_m$—OC(O)—, —(CR$^c$R$^c$)$_m$—C(O)—, —NR$^b$C(S)—, or —NR$^b$C(O)— (wherein the point of the attachment to R$^1$ is on the left-hand side);

R$^1$ is selected from alkyl, cycloalkyl, aryl, heteroaryl, and heterocyclyl; each of which is substituted with 0-5 occurrences of R$^d$;

each R$^3$ is independently selected from halo, haloalkyl, alkyl, hydroxyl and —OR$^a$, or two adjacent R$^3$ taken together with the carbon atoms to which they are attached form an optionally substituted heterocyclyl;

each R$^a$ is independently selected from alkyl, acyl, hydroxyalkyl and haloalkyl;

each R$^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^a R^b$ and —O$R^a$, or two $R^d$ taken together with the carbon atoms to which they are attached form an optionally substituted heterocyclyl;

n is 0, 1, or 2;

m is 1, 2 or 3; and his 1 and g is 2, or g is 1 and his 2.

2. The method of claim 1, wherein W, X, Y and Z are CH.

3. The method of claim 1, wherein D is $NR^b$ and $D^1$ is a bond.

4. The method of claim 1, wherein $R^b$ is H, methyl or ethyl.

5. The method of claim 1, wherein n is 0.

6. The method of claim 1, wherein n is 1 and $R^3$ is $CH_3$, $CH_2CH_3$, $OCH_3$, $OCH_2CH_3$, OH, F, Cl, or $CF_3$.

7. The method of claim 1, wherein L is a bond, —(CR$^c$R$^c$)$_m$—, —NR$^b$C(O)—, —(CR$^c$R$^c$)$_m$—C(O)—, —(CR$^c$R$^c$)$_m$—OC(O)—, —C(O)—, or —O(CO)—.

8. The method of claim 1, wherein the compound or a pharmaceutically acceptable salt thereof is selected from:

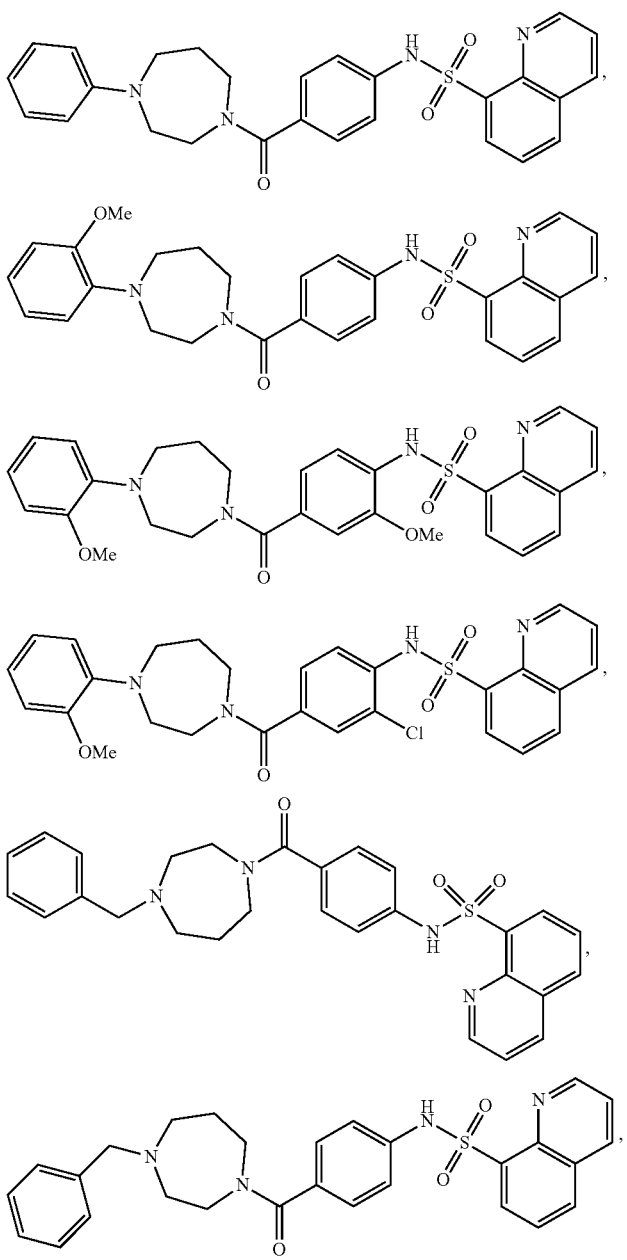

-continued
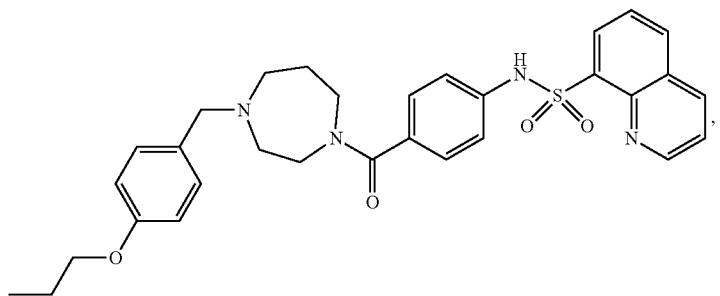
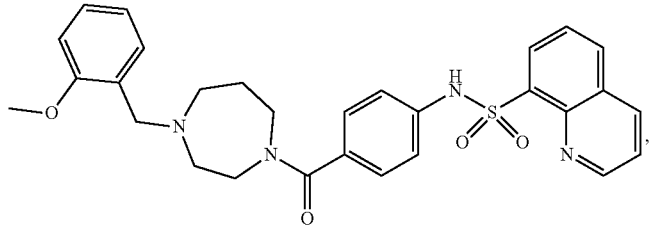
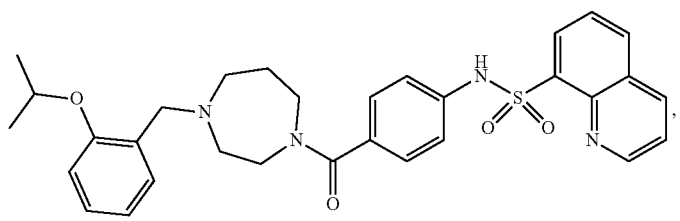
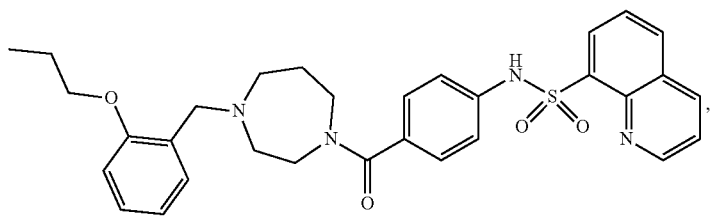
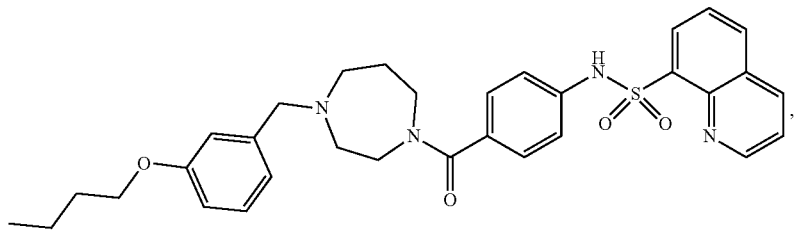
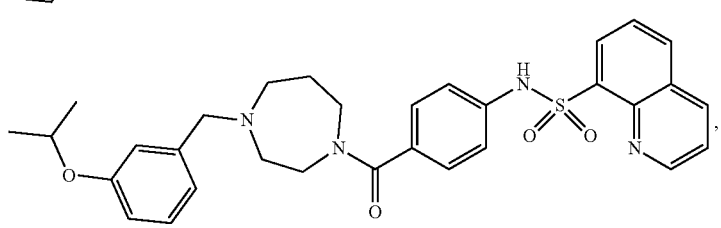
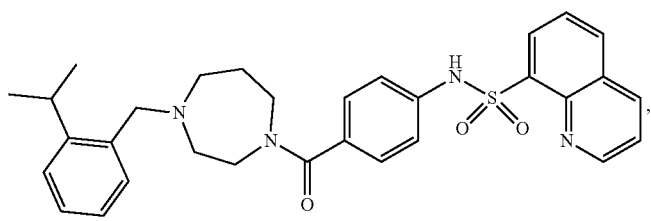

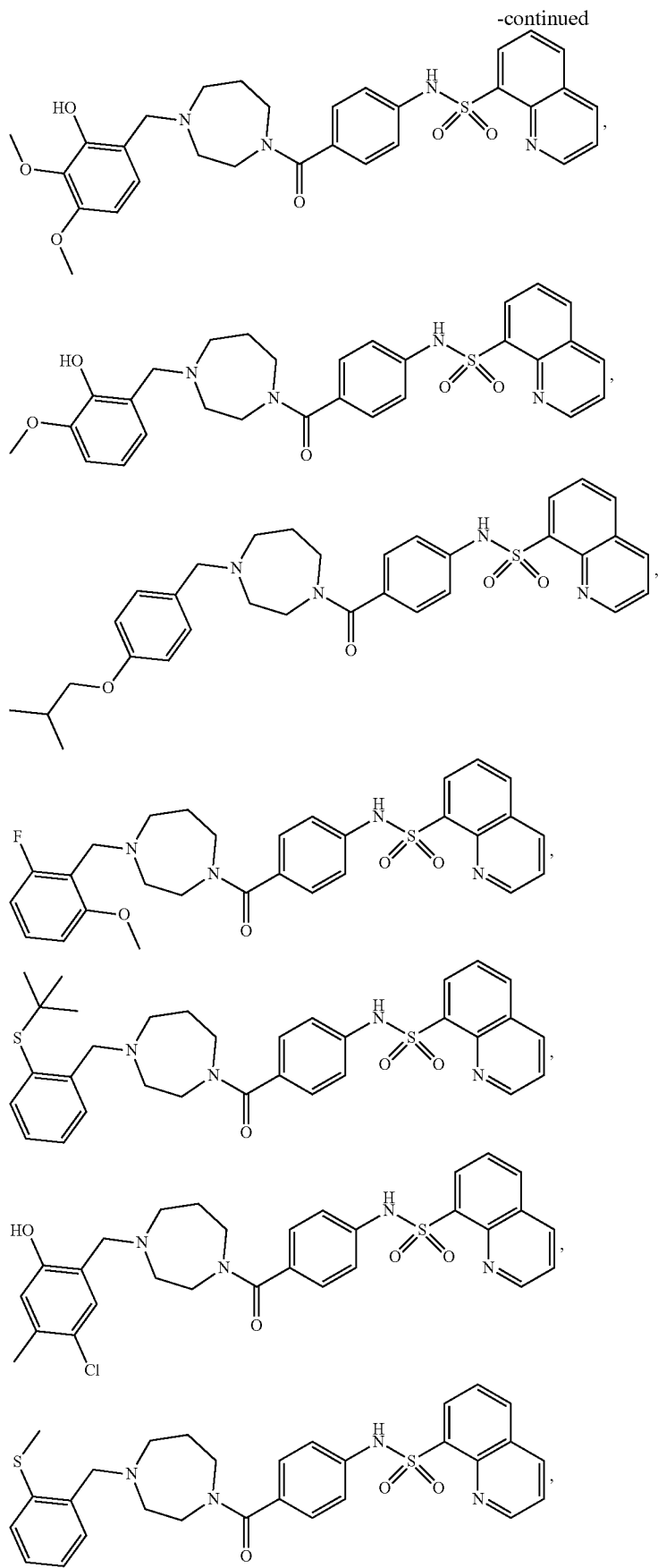

-continued
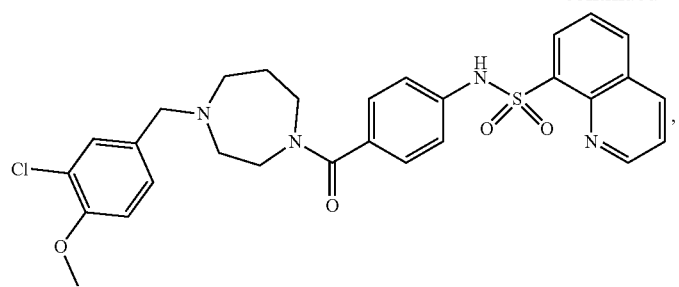
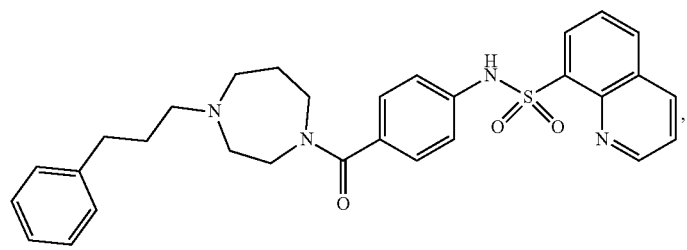
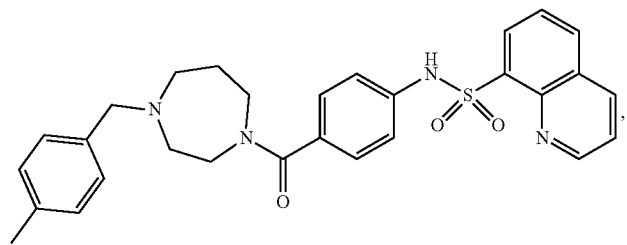
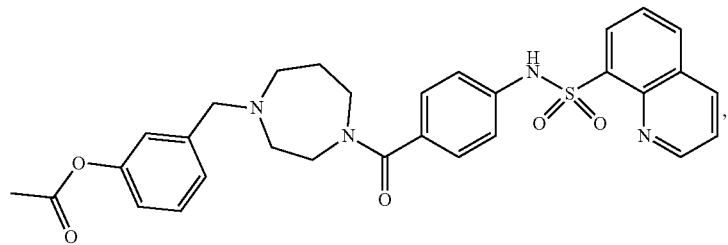
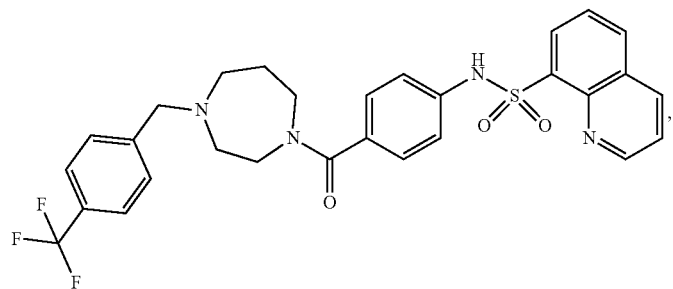
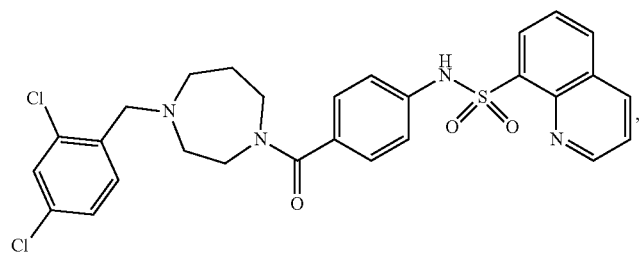

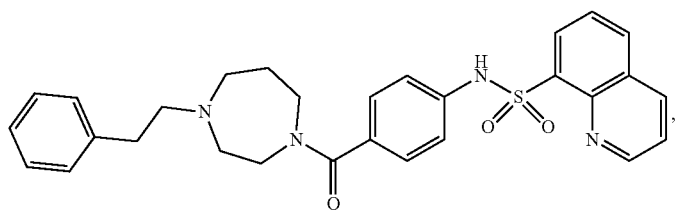
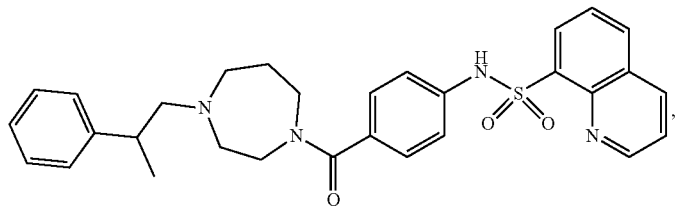
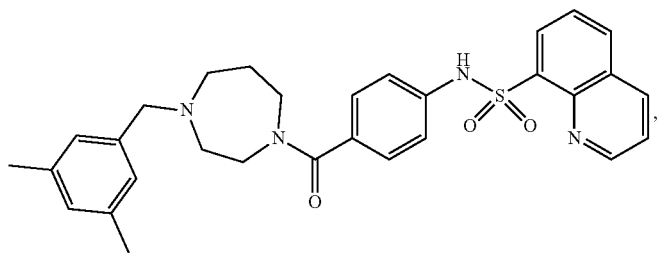
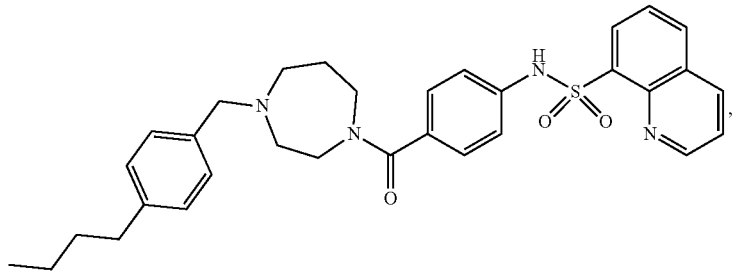
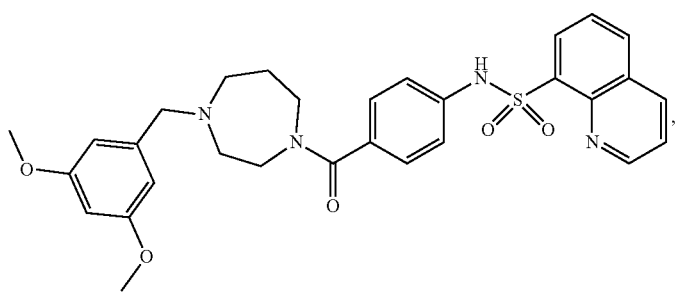
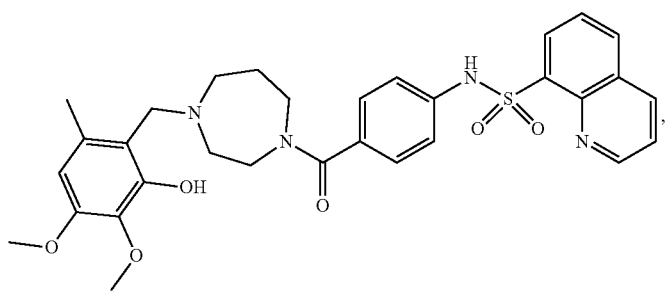

-continued
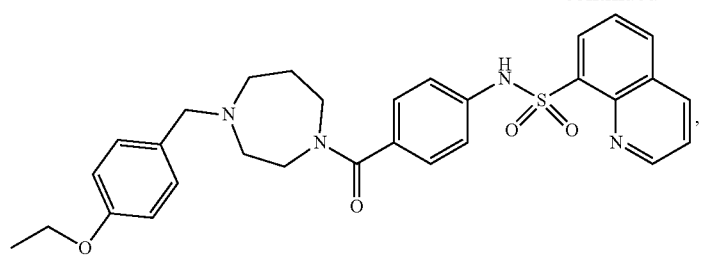
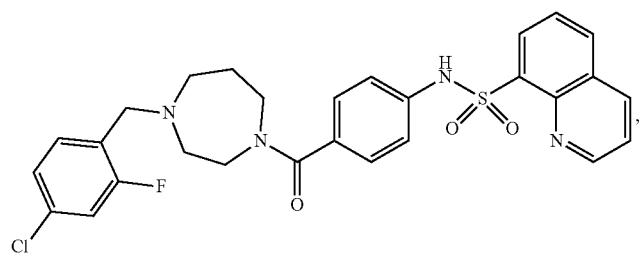
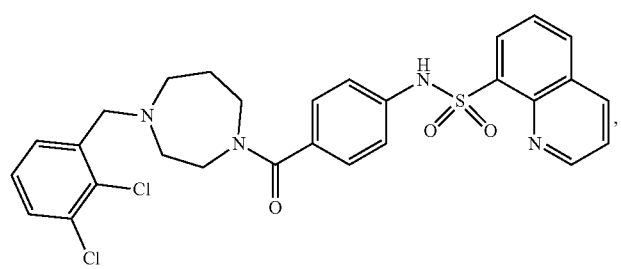
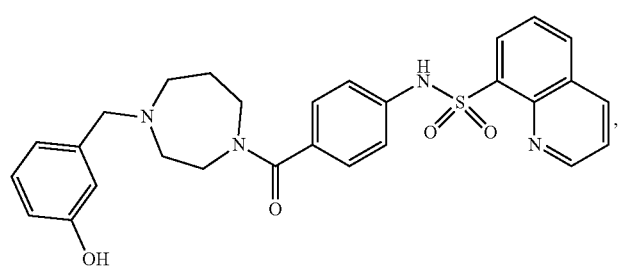
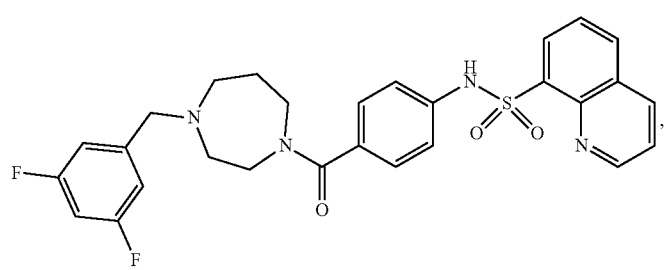
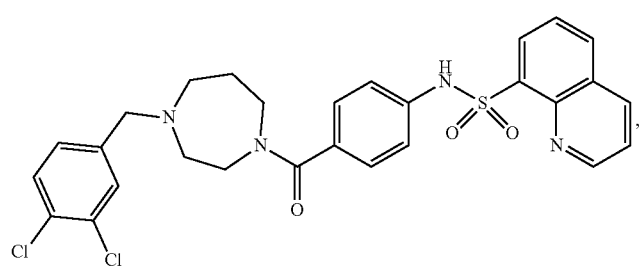

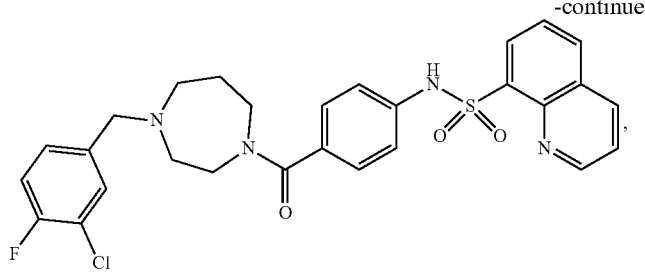
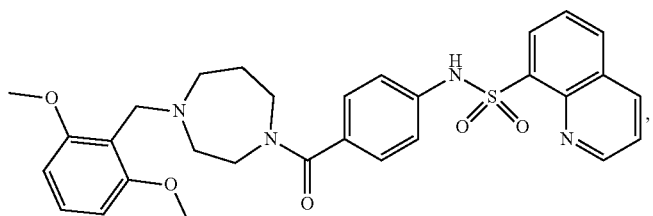
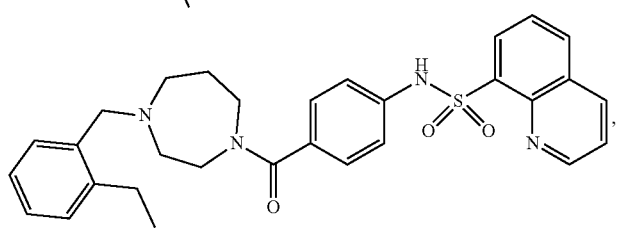
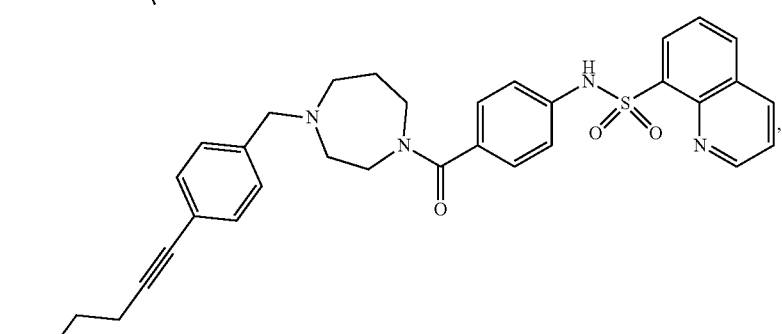
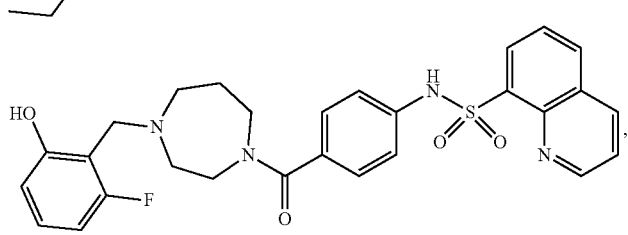
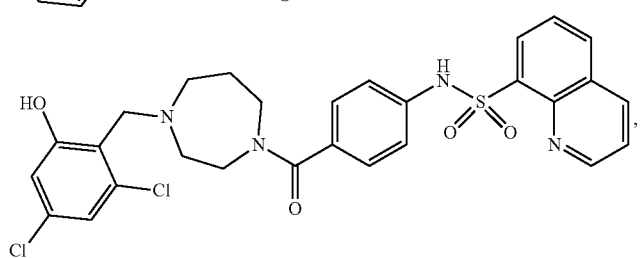
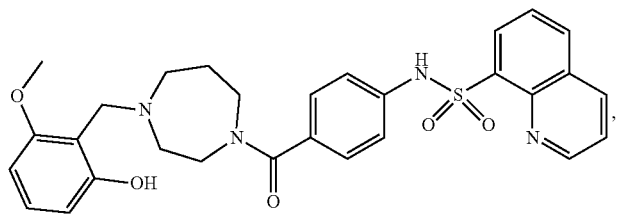

-continued
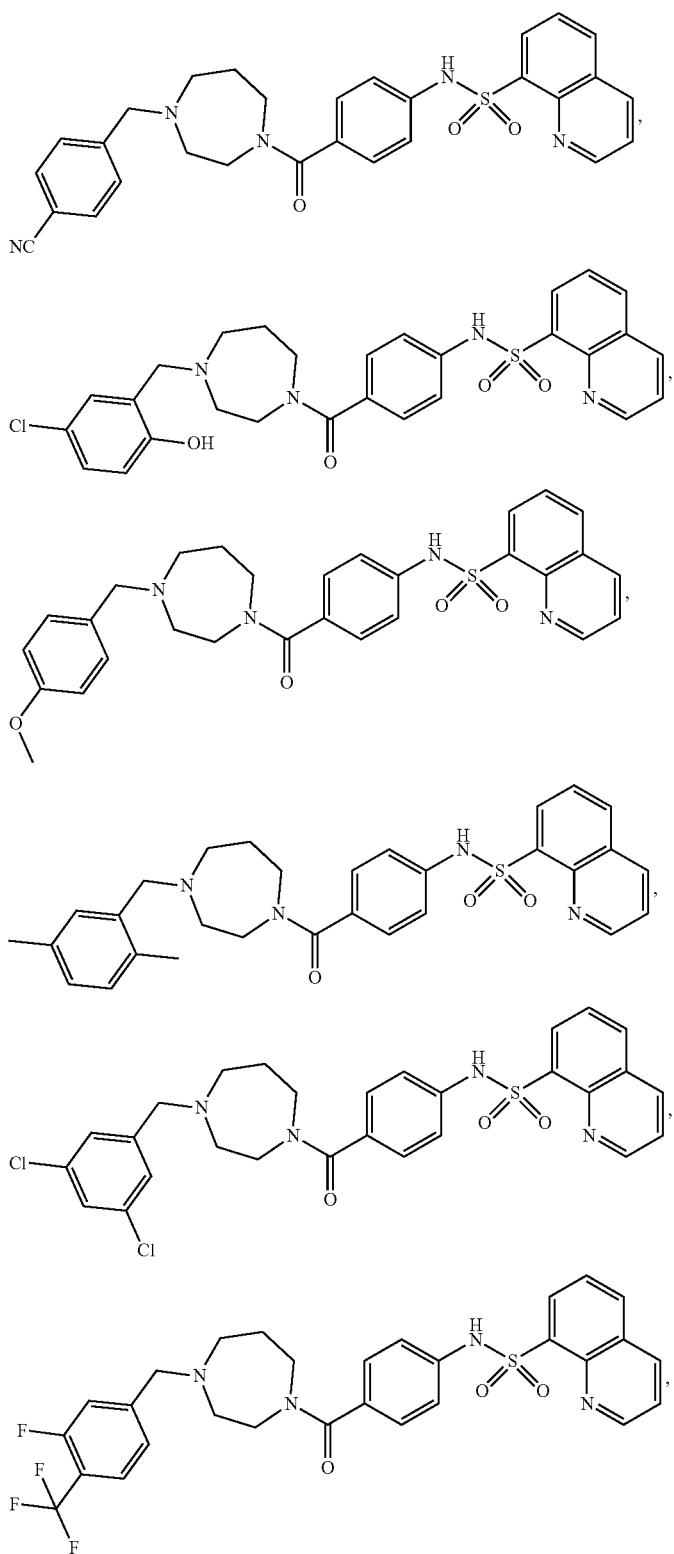

-continued
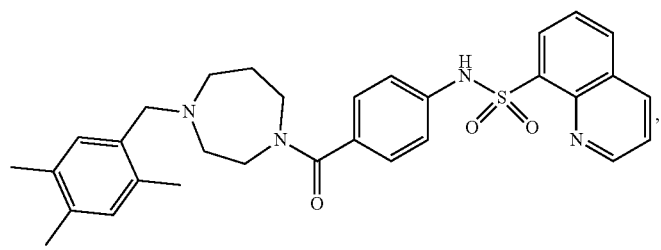
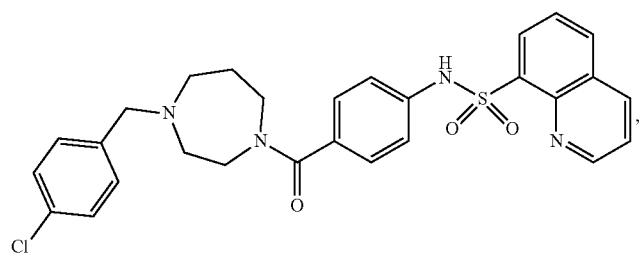
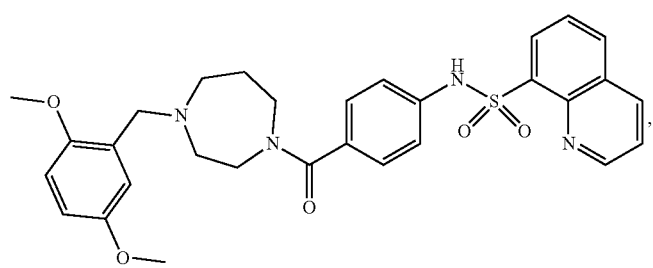
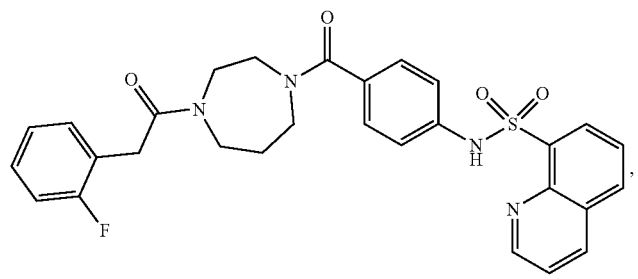
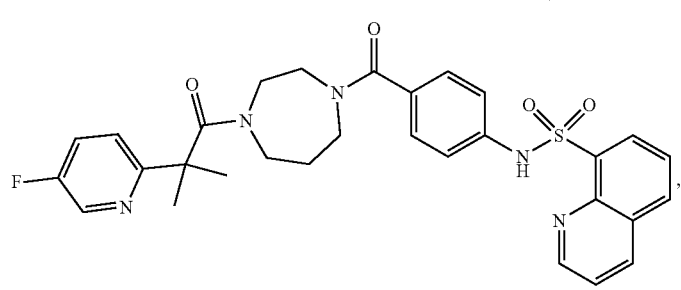
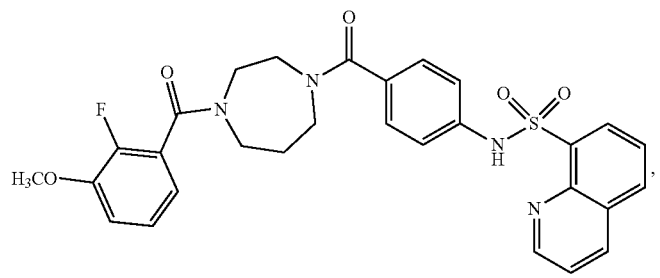

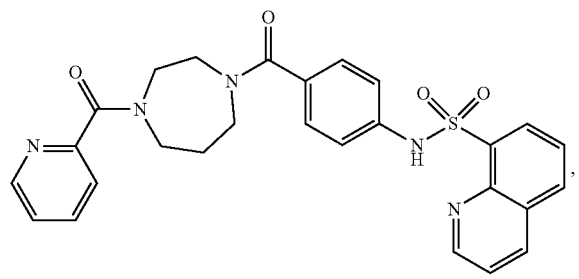
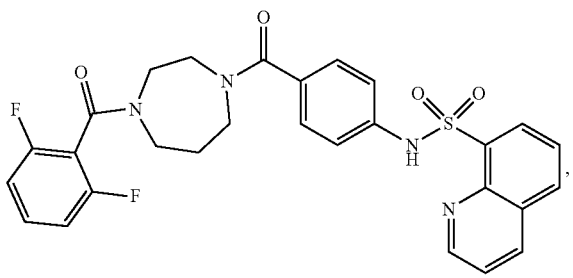
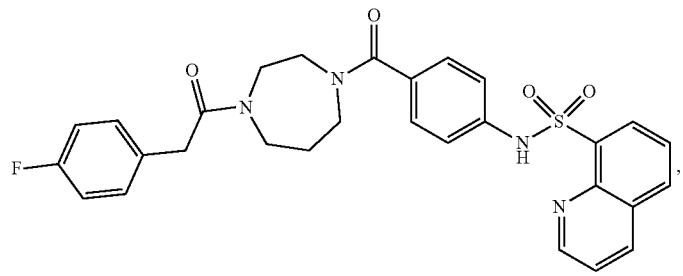
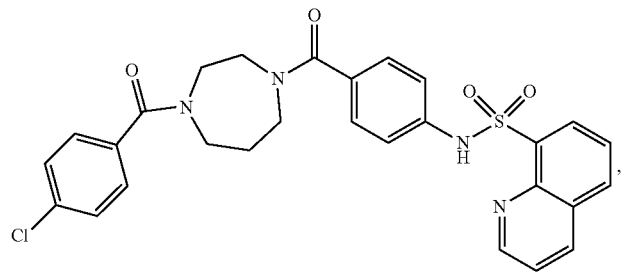
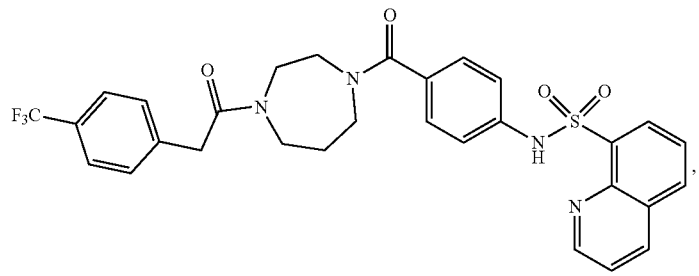
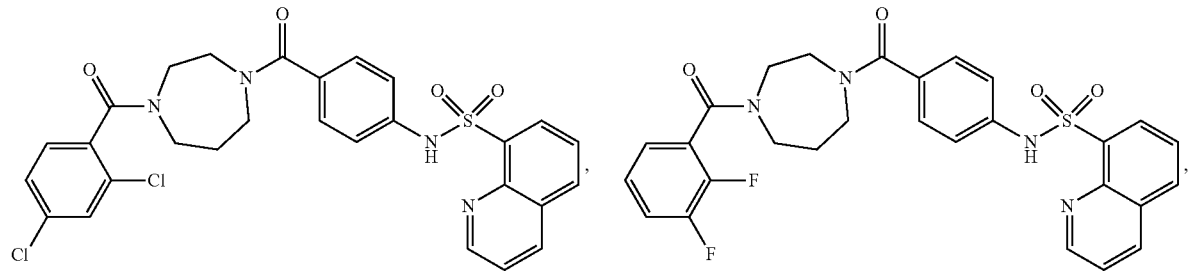
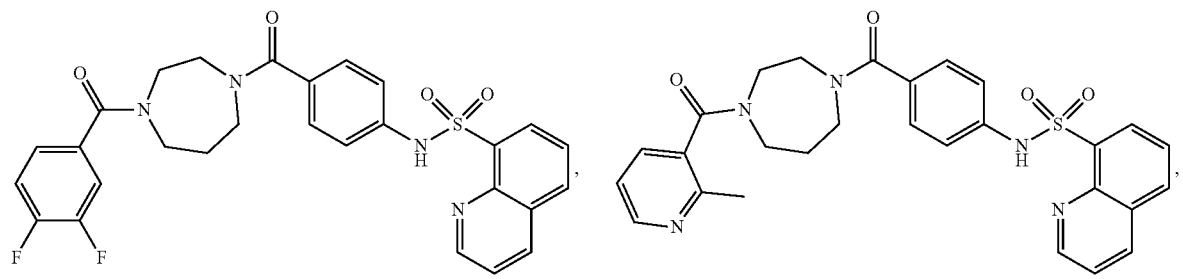

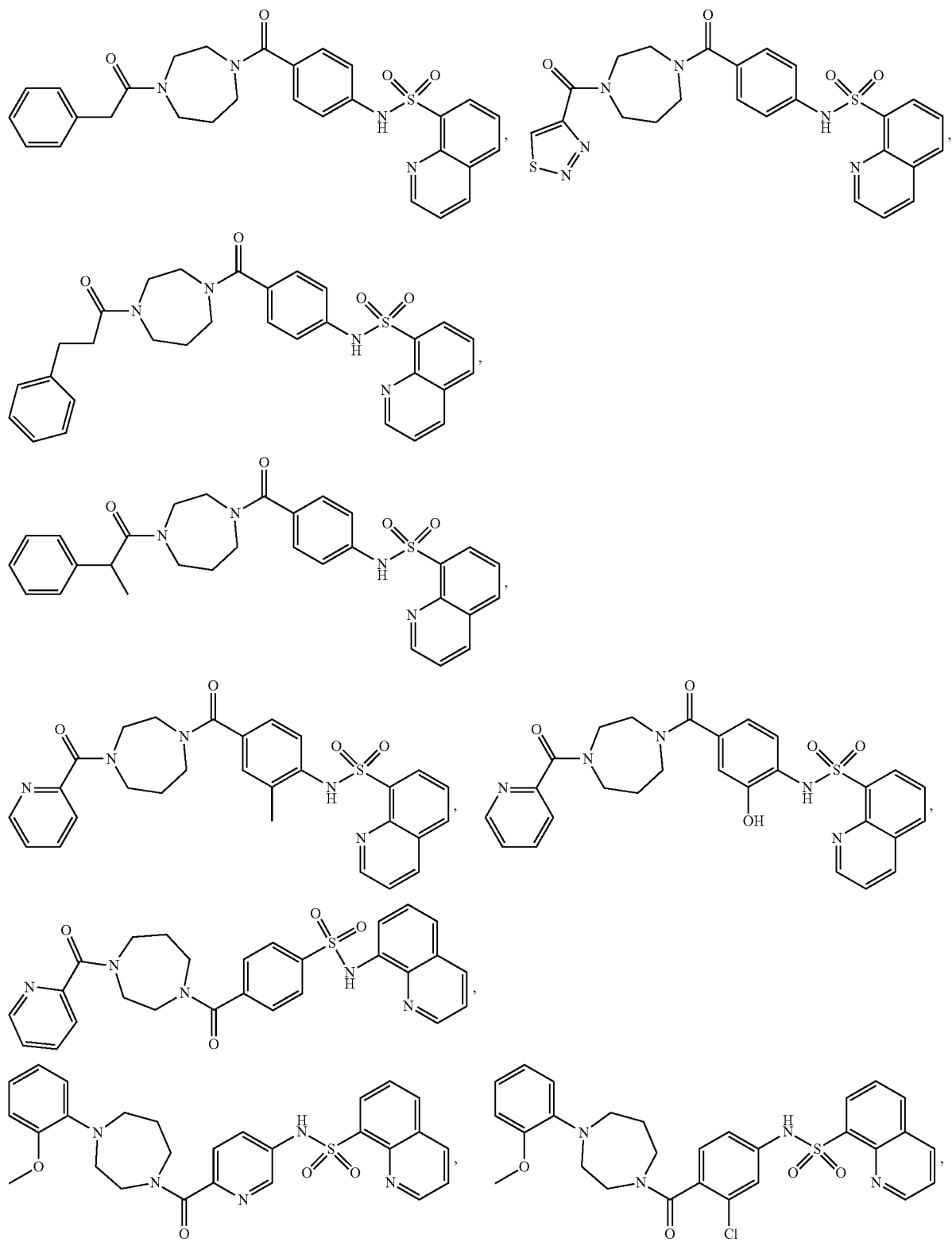

-continued
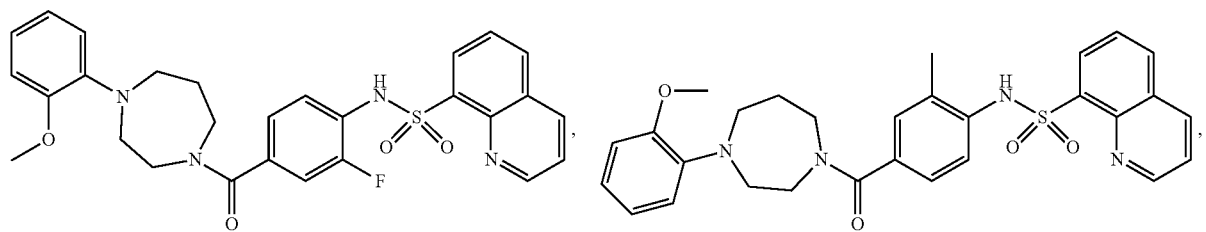
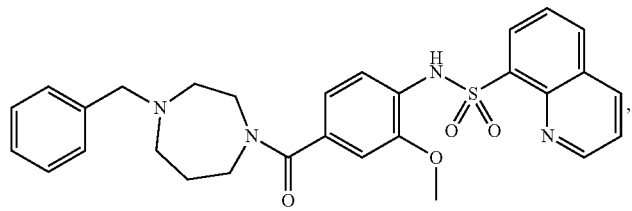
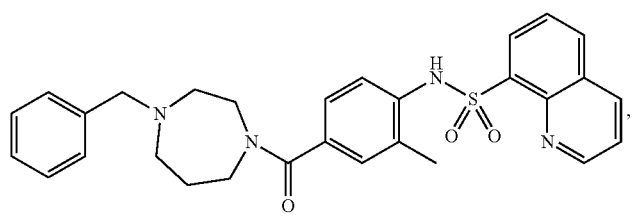
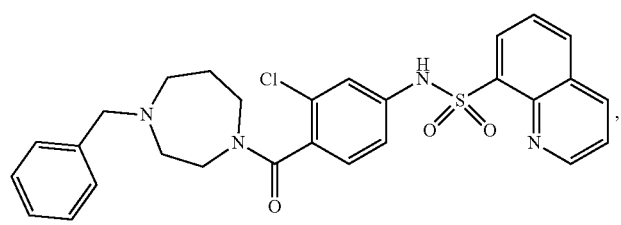
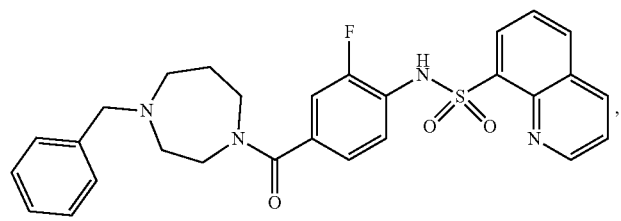
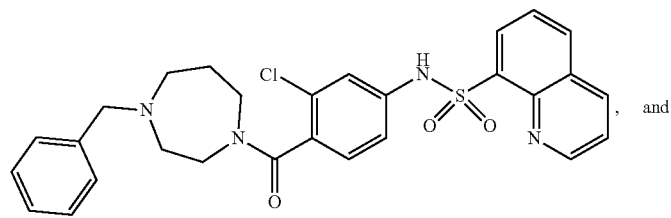, and
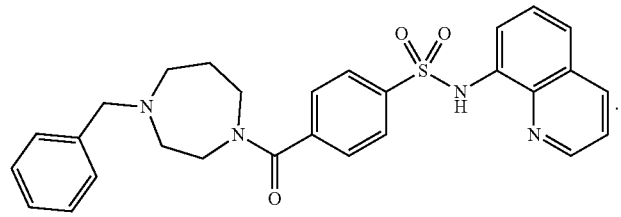

9. A method of activating a mutant pyruvate kinase R in a subject in need thereof, comprising administering to the subject a therapeutically effective amount of a compound of formula (I) or a pharmaceutically acceptable salt thereof, wherein:

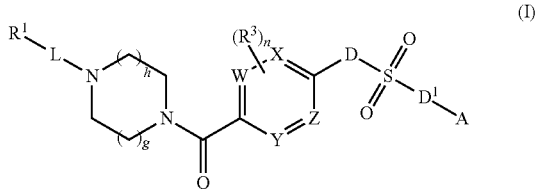

W, X, Y and Z are each independently selected from CH or N;
D and $D^1$ are each independently selected from a bond and $NR^b$;
A is optionally substituted aryl or optionally substituted heteroaryl;
L is a bond, —C(O)—, —(CR$^c$R$^c$)$_m$—, —OC(O)—, —(CR$^c$R$^c$)$_m$—OC(O)—, —(CR$^c$R$^c$)$_m$—C(O)—, —NR$^b$C(S)—, or —NR$^b$C(O)— (wherein the point of the attachment to $R^1$ is on the left-hand side);
$R^1$ is selected from alkyl, cycloalkyl, aryl, heteroaryl, and heterocyclyl; each of which is substituted with 0-5 occurrences of $R^d$;
each $R^3$ is independently selected from halo, haloalkyl, alkyl, hydroxyl and —OR$^a$, or two adjacent $R^3$ taken together with the carbon atoms to which they are attached form an optionally substituted heterocyclyl;
each $R^a$ is independently selected from alkyl, acyl, hydroxyalkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted cycloalkyl;
each $R^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two $R^d$ taken together with the carbon atoms to which they are attached form an optionally substituted heterocyclyl;
n is 0, 1, or 2;
m is 1, 2 or 3; and
his 1 and g is 2, or g is 1 and h is 2.

10. The method of claim 9, wherein W, X, Y and Z are CH.

11. The method of claim 9, wherein D is $NR^b$ and $D^1$ is a bond.

12. The method of claim 9, wherein $R^b$ is H, methyl or ethyl.

13. The method of claim 9, wherein n is 0.

14. The method of claim 9, wherein n is 1 and $R^3$ is CH$_3$, CH$_2$CH$_3$, OCH$_3$, OCH$_2$CH$_3$, OH, F, Cl, or CF$_3$.

15. The method of claim 9, wherein L is a bond, —(CR$^c$R$^c$)$_m$—, —NR$^b$C(O)—, —(CR$^c$R$^c$)$_m$—C(O)—, —(CR$^c$R$^c$)$_m$—OC(O)—, —C(O)—, or —O(CO)—.

16. The method of claim 9, wherein the compound or a pharmaceutically acceptable salt thereof is selected from:

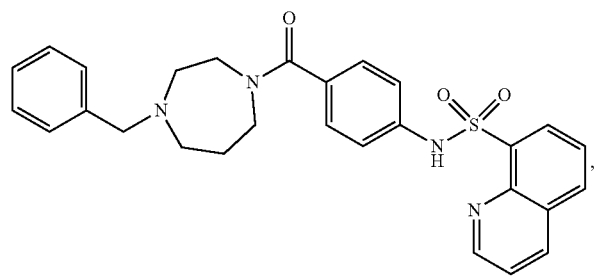
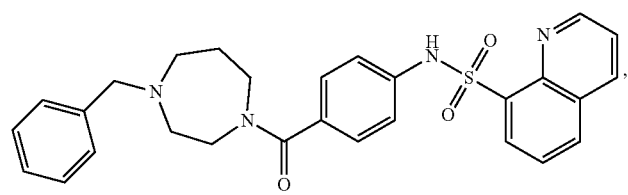
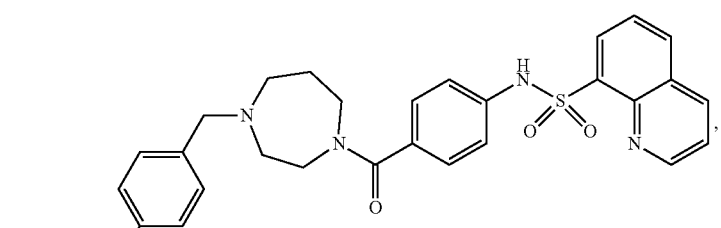
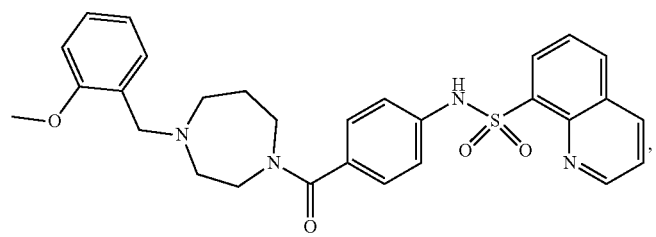
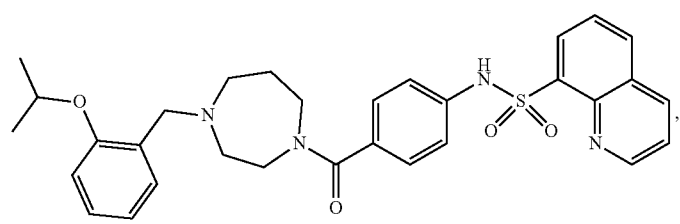
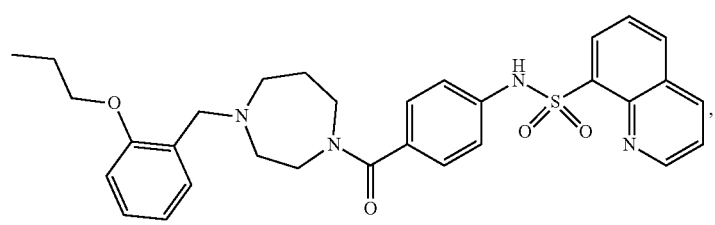
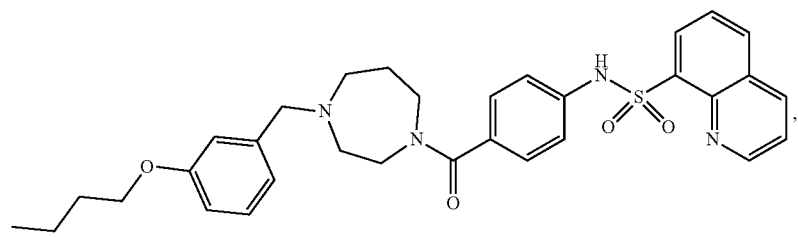

-continued
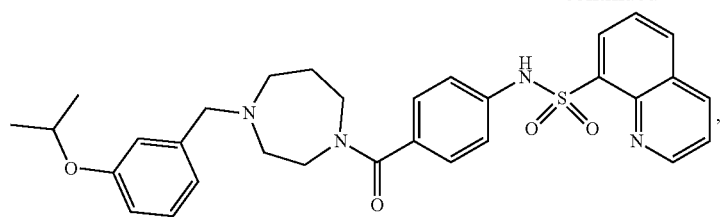
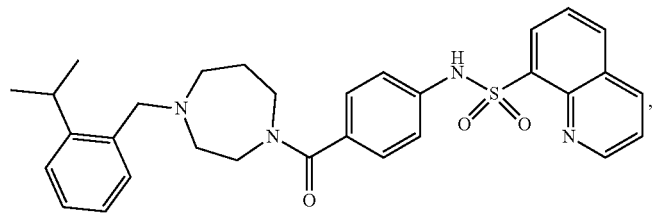
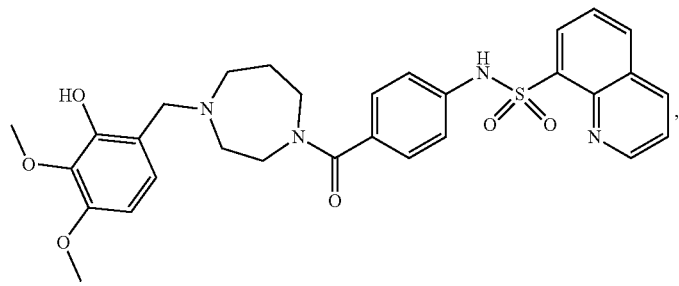
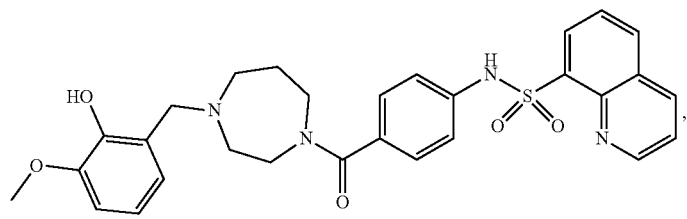
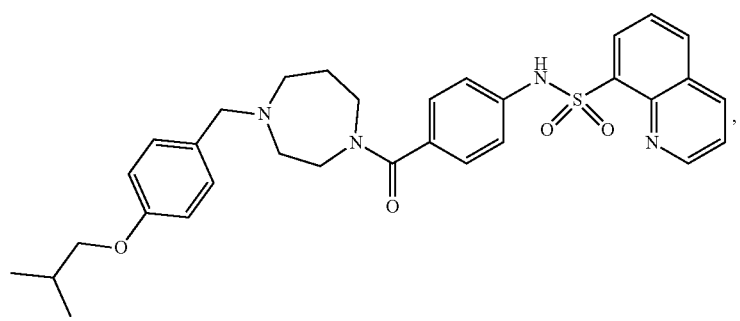
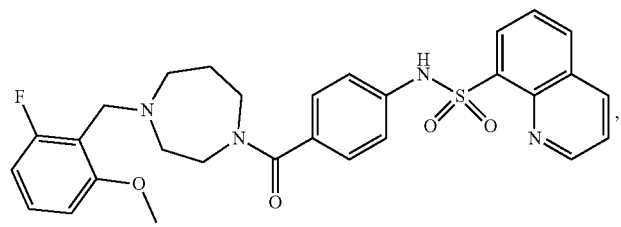
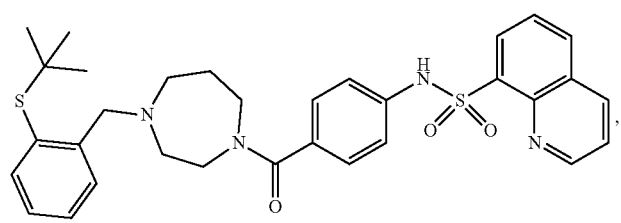

-continued
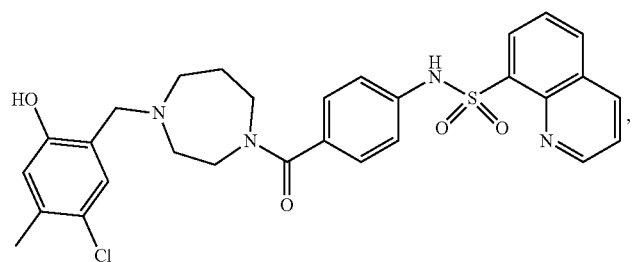
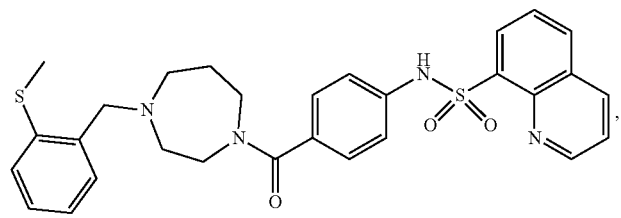
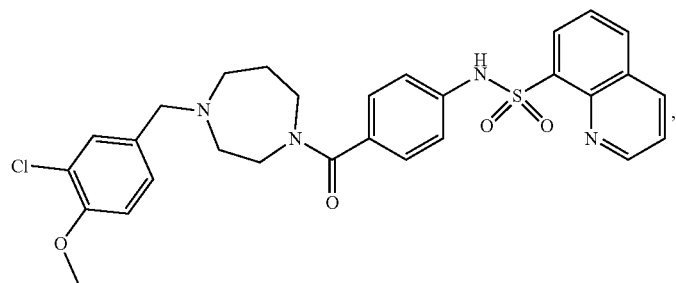
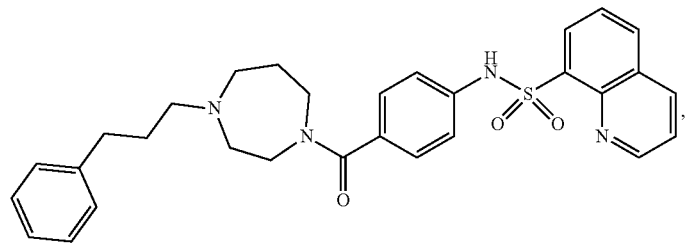
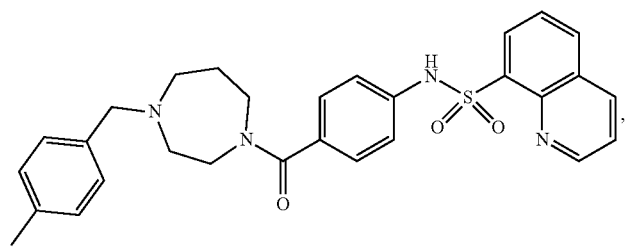
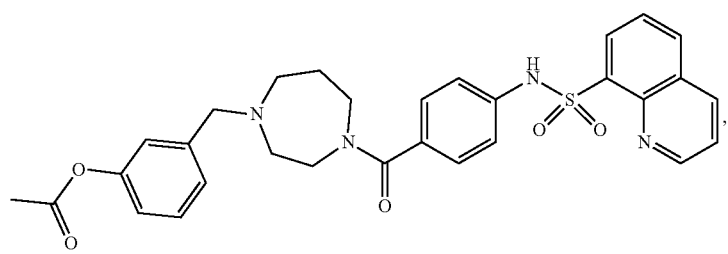

-continued
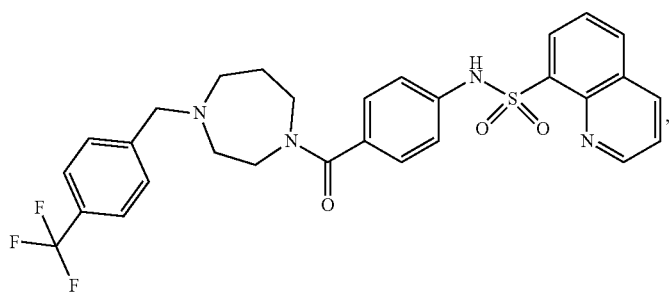
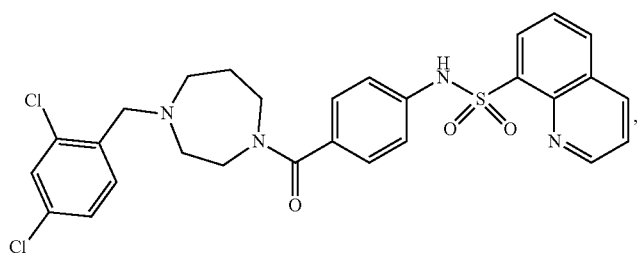
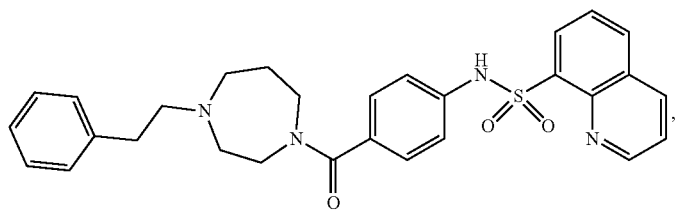
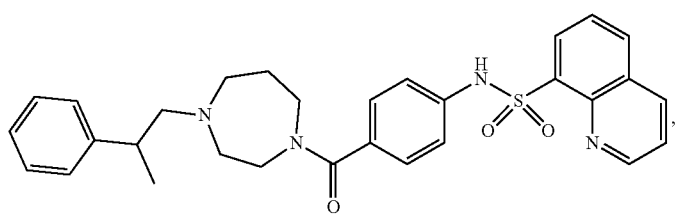
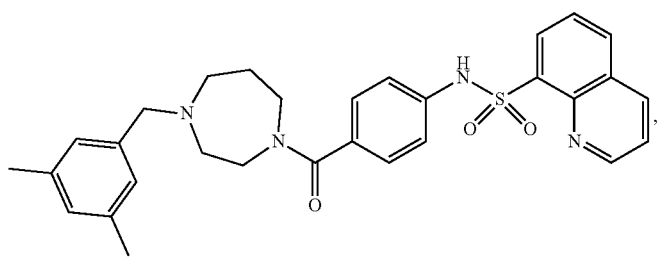
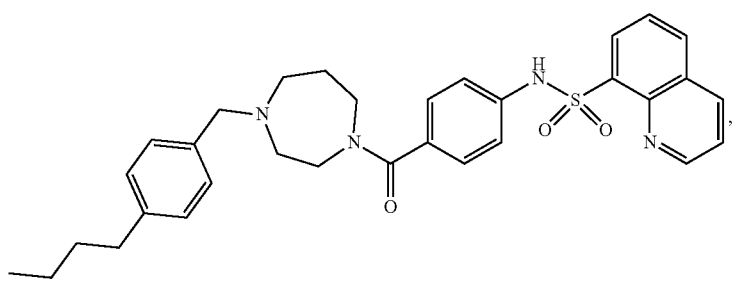

-continued
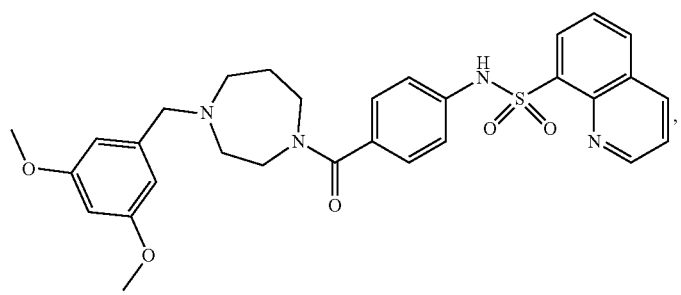
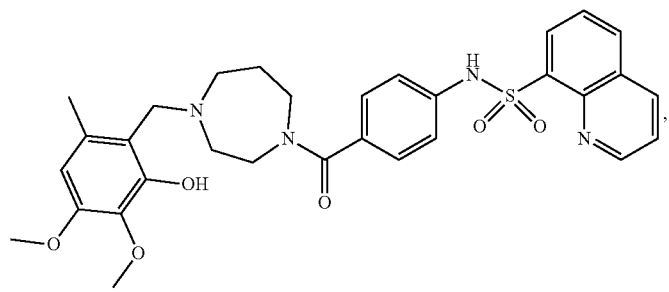
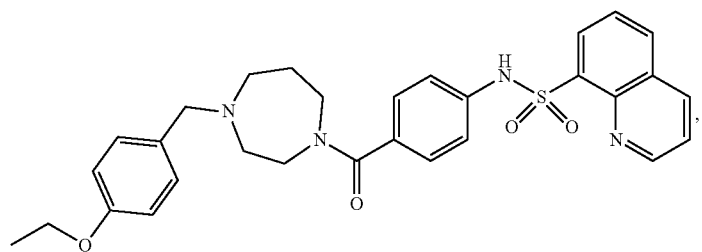
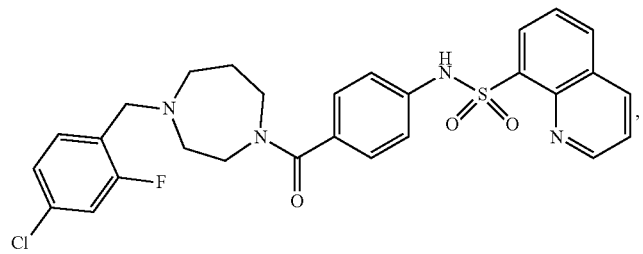
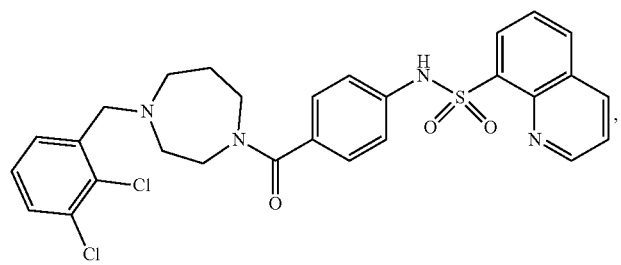
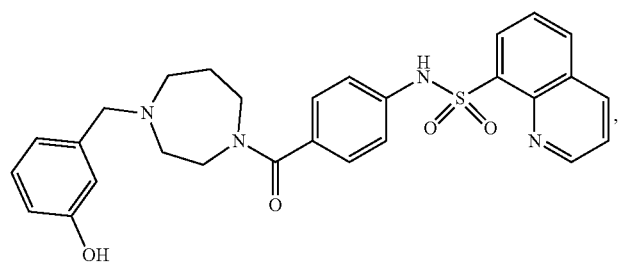

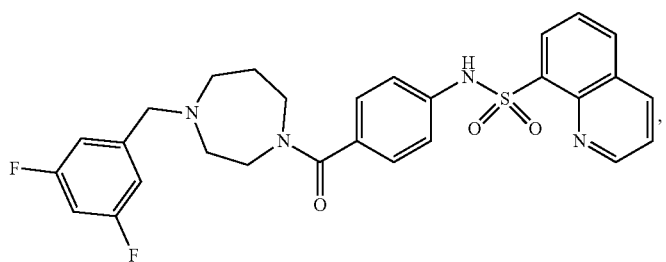
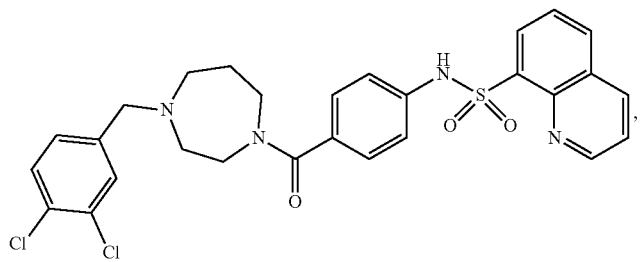
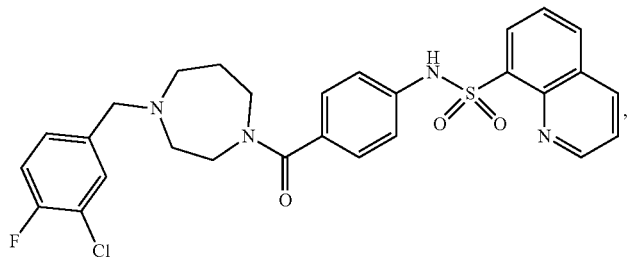
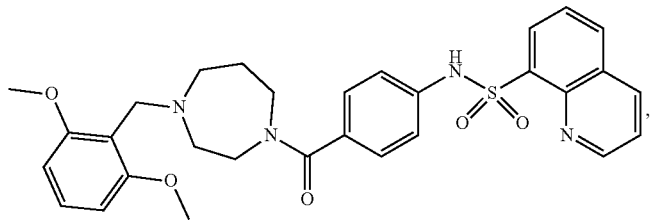
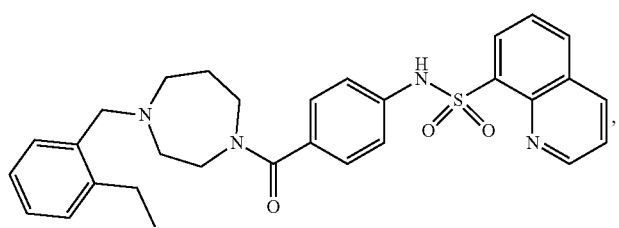
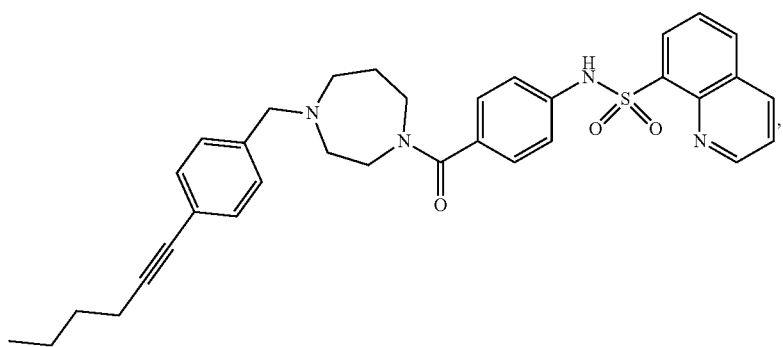

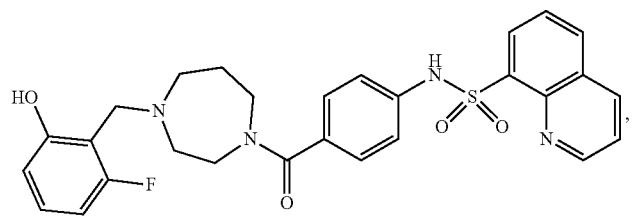
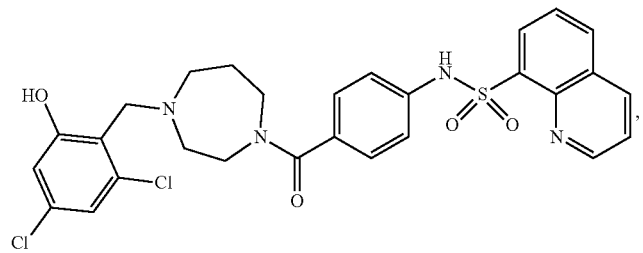
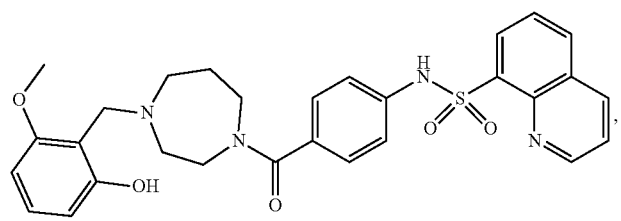
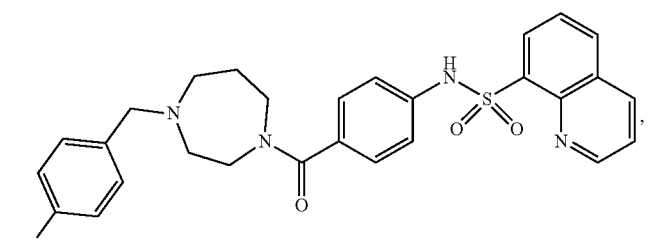
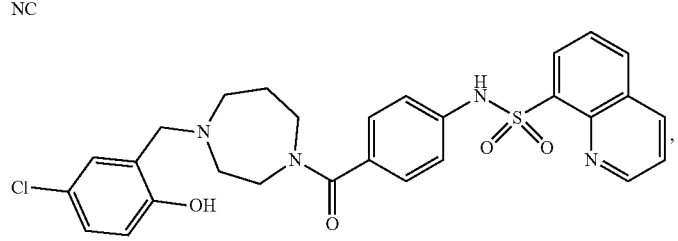
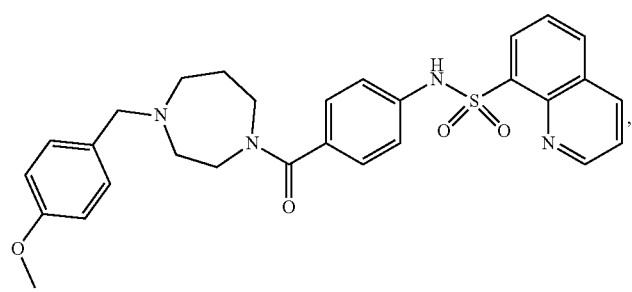
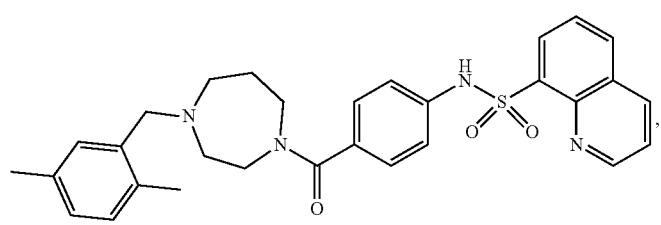

-continued
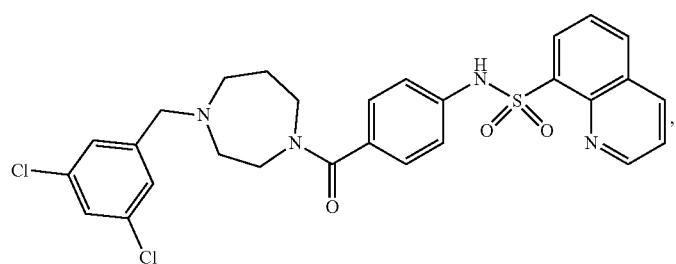
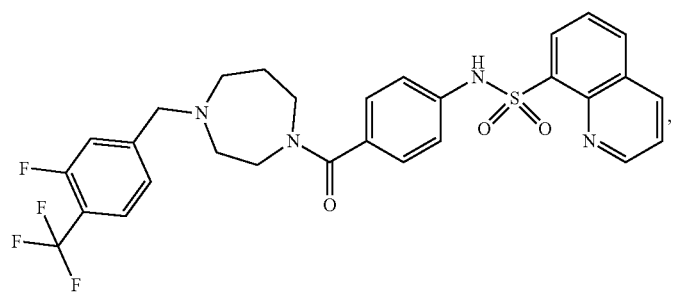
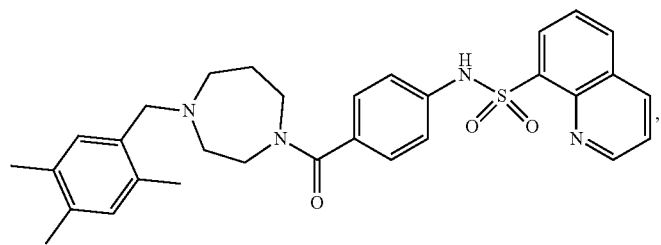
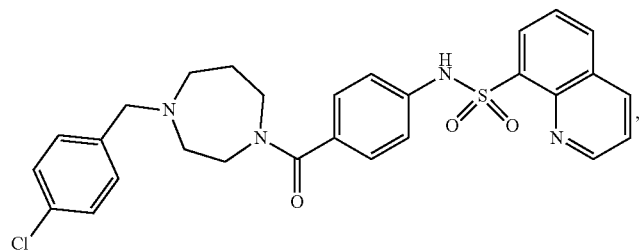
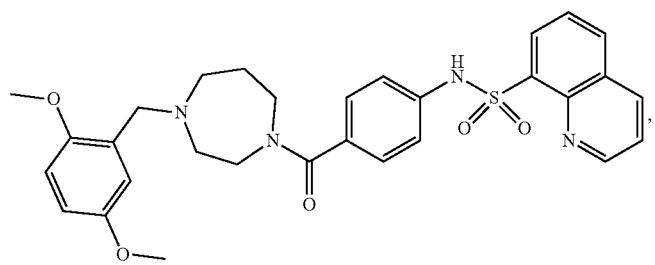
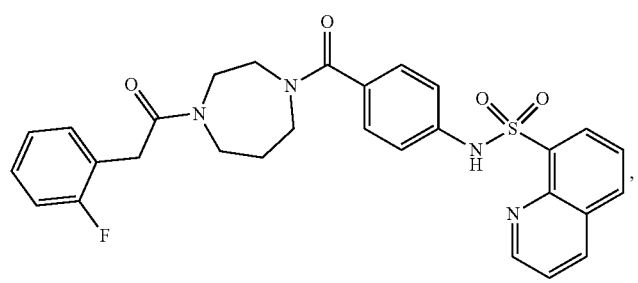

-continued
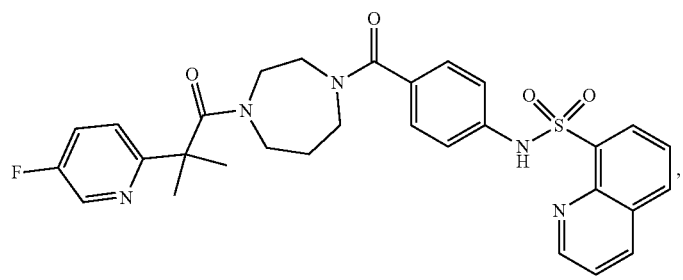
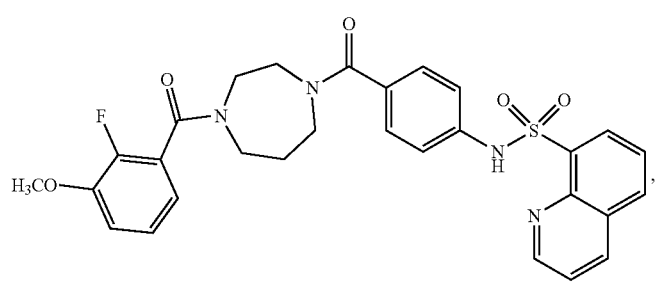
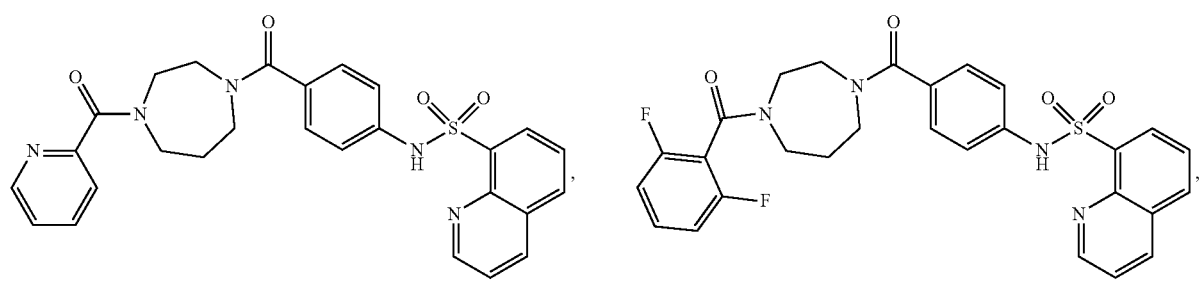
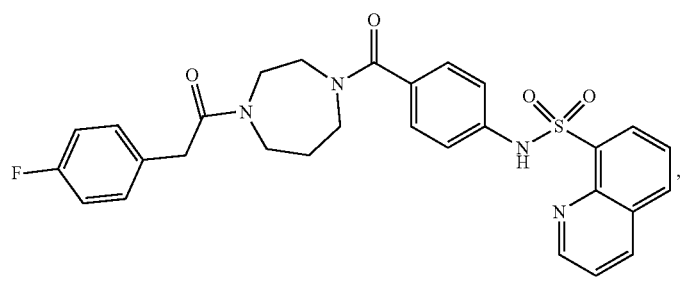
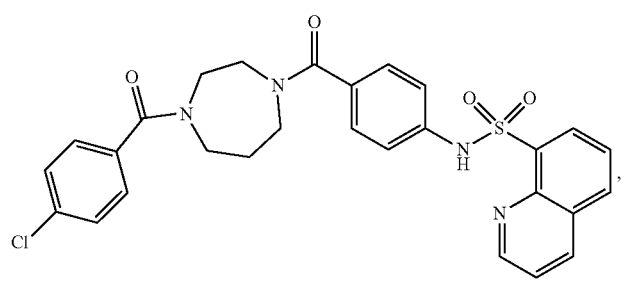

-continued
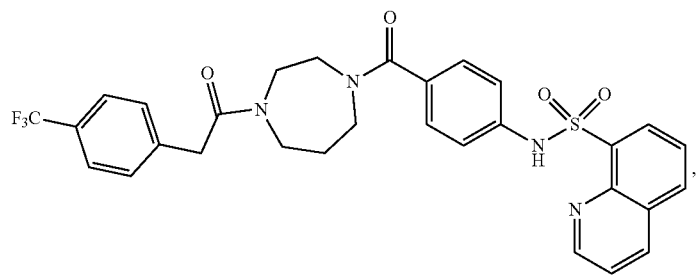
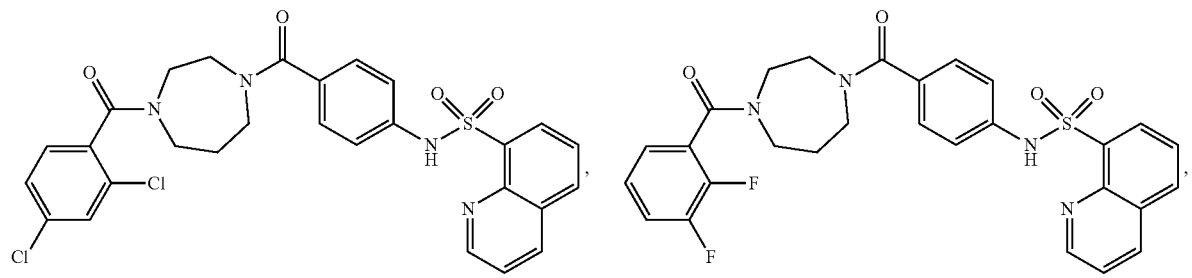
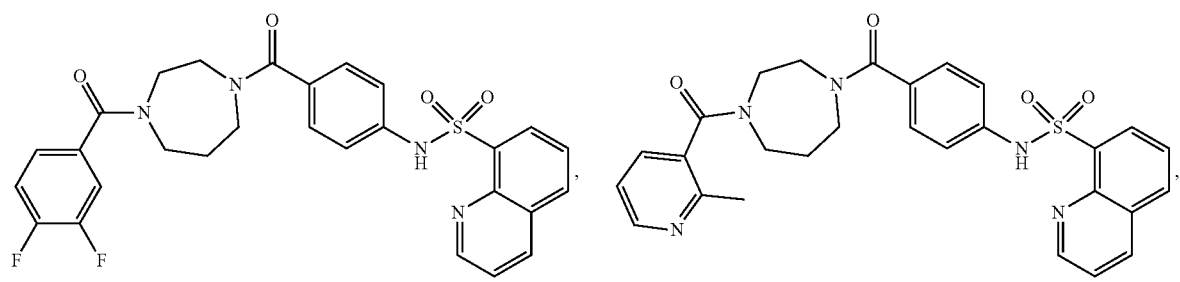
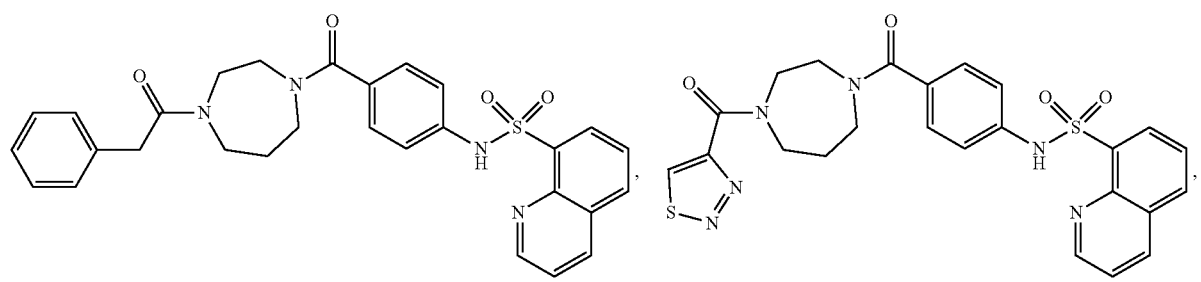
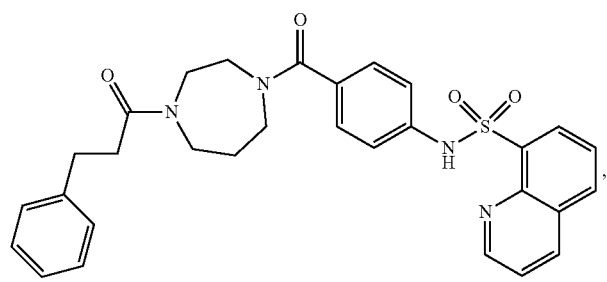
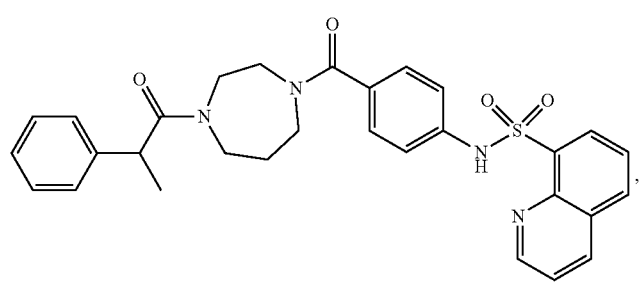

75 76
-continued
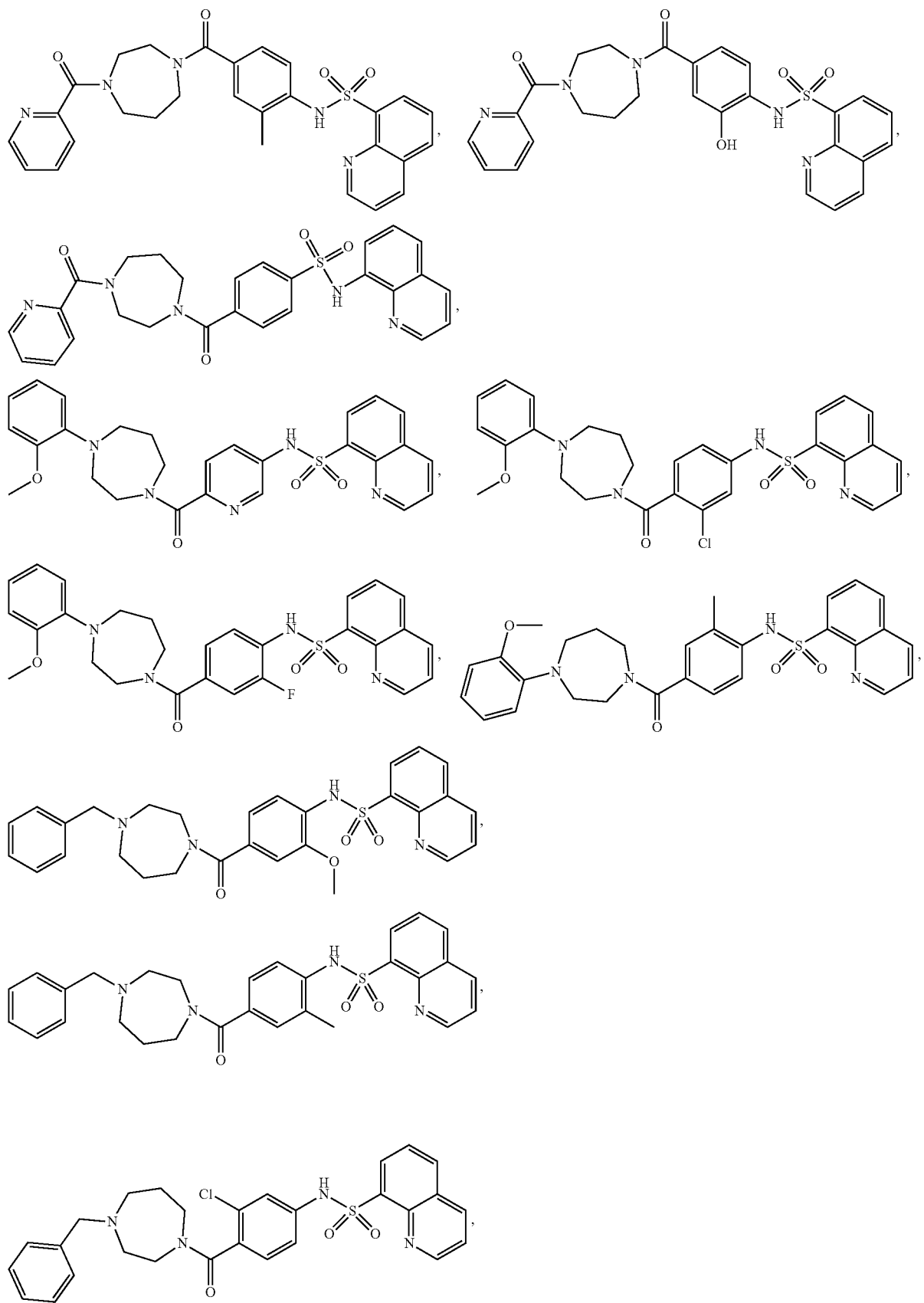

-continued
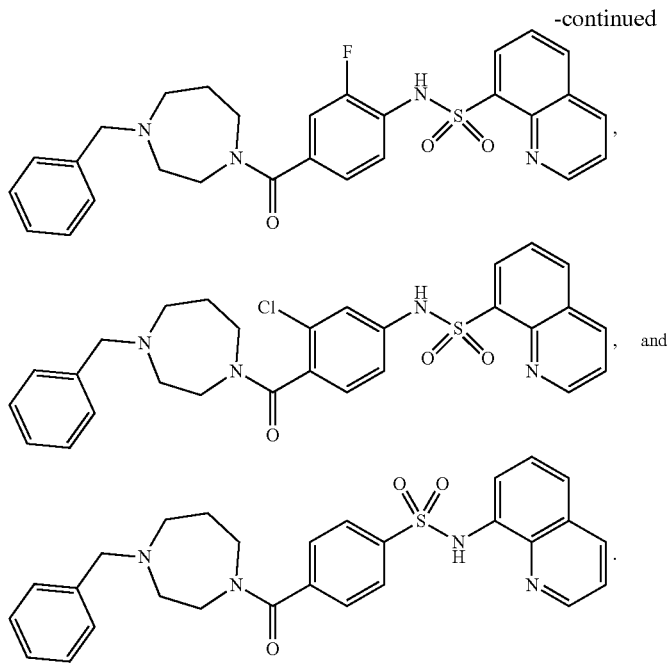
* * * * *